(12) United States Patent
Niculescu

(10) Patent No.: US 10,991,449 B2
(45) Date of Patent: Apr. 27, 2021

(54) PREDICTING SUICIDALITY USING A COMBINED GENOMIC AND CLINICAL RISK ASSESSMENT

(71) Applicants: Indiana University Research and Technology Corporation, Indianapolis, IN (US); United States Government as represented by the Department of Veterans Affairs, Washington, DC (US)

(72) Inventor: Alexander Bogdan Niculescu, Indianapolis, IN (US)

(73) Assignee: Indiana University Research and Technology Corporation, Indianapolis, IN (US)

(*) Notice: Subject to any disclaimer, the term of this patent is extended or adjusted under 35 U.S.C. 154(b) by 0 days.

(21) Appl. No.: 15/735,304

(22) PCT Filed: Jun. 10, 2016

(86) PCT No.: PCT/US2016/036985
§ 371 (c)(1),
(2) Date: Dec. 11, 2017

(87) PCT Pub. No.: WO2016/201299
PCT Pub. Date: Dec. 15, 2016

(65) Prior Publication Data
US 2018/0181701 A1 Jun. 28, 2018

Related U.S. Application Data

(60) Provisional application No. 62/278,707, filed on Jan. 14, 2016, provisional application No. 62/174,880, filed on Jun. 12, 2015.

(51) Int. Cl.
| | | |
|---|---|---|
| *A61K 38/00* | (2006.01) | |
| *C12Q 1/68* | (2018.01) | |
| *G01N 33/567* | (2006.01) | |
| *G16B 20/00* | (2019.01) | |
| *G16B 25/00* | (2019.01) | |
| *G01N 33/48* | (2006.01) | |
| *C12Q 1/6883* | (2018.01) | |
| *G16H 50/20* | (2018.01) | |
| *G16H 10/20* | (2018.01) | |
| *G16H 50/30* | (2018.01) | |
| *C12Q 1/6876* | (2018.01) | |
| *G01N 33/68* | (2006.01) | |

(52) U.S. Cl.
CPC .............. *G16B 20/00* (2019.02); *C12Q 1/68* (2013.01); *C12Q 1/6876* (2013.01); *C12Q 1/6883* (2013.01); *G01N 33/48* (2013.01); *G01N 33/6893* (2013.01); *G16B 25/00* (2019.02); *G16H 10/20* (2018.01); *G16H 50/20* (2018.01); *G16H 50/30* (2018.01); *C12Q 2600/118* (2013.01); *C12Q 2600/158* (2013.01); *G01N 2800/304* (2013.01); *G01N 2800/50* (2013.01); *Y02A 90/10* (2018.01)

(58) Field of Classification Search
CPC .............. G01N 33/48; G01N 800/304; G01N 2800/50; G16H 50/20; G16H 50/30; C12Q 2600/118; C12Q 2600/158
See application file for complete search history.

(56) References Cited

U.S. PATENT DOCUMENTS

| | | | |
|---|---|---|---|
| 8,401,801 | B2 | 3/2013 | Mrazek et al. |
| 8,688,385 | B2 | 4/2014 | Mrazek et al. |
| 10,196,693 | B2 | 2/2019 | Peterson et al. |
| 2005/0282911 | A1 | 12/2005 | Hakkarainen et al. |
| 2012/0041911 | A1 | 2/2012 | Pestian et al. |
| 2012/0269906 | A1 | 10/2012 | Sheehan et al. |
| 2013/0142776 | A1 | 6/2013 | Blumenfeld |
| 2013/0330429 | A1 | 12/2013 | Vuckovic |
| 2014/0235663 | A1 | 8/2014 | Yovell |
| 2014/0243211 | A1 | 8/2014 | Niculescu et al. |
| 2016/0153044 | A1 | 6/2016 | Kaminsky et al. |
| 2016/0215346 | A1 | 7/2016 | Niculescu |
| 2020/0312425 | A1 | 10/2020 | Niculescu |
| 2020/0318188 | A1 | 10/2020 | Niculescu |

FOREIGN PATENT DOCUMENTS

| | | |
|---|---|---|
| WO | 2015006645 A1 | 1/2015 |
| WO | 20161201299 A1 | 12/2016 |

OTHER PUBLICATIONS

Le-Niculescu et al., Molecular Psychiatry, 2013, 18:1249-64.*
Bertone-Johnson et al., Vitamin D and the Occurrence of Depression: Casual Associate or Circumstantial Evidence?; Nutr Ref. Aug. 2009, vol. 67, No. 8, pp. 481-492.
Brent et al., Pharmacogenomics of Suicidal events; Pharmacogenomics, 2010, vol. 11, No. 6, pp. 793-807.
Stopkova et al., Identification of PIK3C3 Promoter Variant Associated with Bipolar Disorder and Schizophrenia, Biol. Psychiatry, 2004, vol. 55, pp. 981-988.
Levey et al., Towards understanding and predicting suicidality in women: biomarkers and clinical risk assessment; Molecular Psychiatry, 2016, vol. 21, pp. 768-785.

(Continued)

*Primary Examiner* — Olga N Chernyshev
(74) *Attorney, Agent, or Firm* — Faegre Drinker Biddle & Reath LLP

(57) ABSTRACT

Biomarkers and methods for screening expression levels of the biomarkers for predicting suicidality (referred herein to suicidal ideation and actions, future hospitalizations and suicide completion) are disclosed. Also disclosed are quantitative questionnaires and mobile applications for assessing affective state and for assessing socio-demographic and psychological suicide risk factors, and their use to compute scores that can predict suicidality. Finally, an algorithm that combines biomarkers and computer apps for identifying subjects who are at risk for committing suicide is disclosed, as well as methods to mitigate and prevent suicidality based on the biomarkers and computer apps.

14 Claims, 40 Drawing Sheets

(56) References Cited

OTHER PUBLICATIONS

Tsai et al., Bcl-2 associated with positive symptoms of schizophrenic patients in an acute phase; Psychiatry Research; 2013, vol. 216, pp. 735-732.
Ayalew M. et al., "Convergent functional genomics of schizophrenia: from comprehensive understanding to genetic risk prediction," Molecular Psychiatry 17, 887-905, doi:10.1038/mp.2012.37 (2012).
Belzeaux et al. (2010) "Clinical variations modulate patterns of gene expression and define blood biomarkers in major depression" Journal of Psychiatric Research 44(16): 1205-1213.
Benedetti et al., Opposite effects of suicidality and lithium on gray matter volumes in bipolar depression. J Affect Disord 135, 139-147, doi:10.1016/.jad.2011.07.006 (2011).
Berngruber, T. W., S. Lion, et al., "Evolution of suicide as a defence strategy against pathogens in a spatially structured environment." Ecol Lett (2013).
Brucker et al., "Assessing Risk of Future Suicidality in Emergency Department Patients," Acad. Emerg. Med., (2019), 26(4):376-383.
Chen, G. G., L. M. Fiori, et al. "Evidence of altered polyamine concentrations in cerebral cortex of suicide completers." Neuropsychopharmacology 35(7): 1477-1484 (2010).
Duckworth C.A. et al., "CD24 is expressed in gastric parietal cells and regulates apoptosis and the response to Helicobacter felis infection in the murine stomach," American Journal of Physiology, Gastrointestinal and Liver Physiology 303, G915-926, doi:10.1152/ajpgi.00068.2012 (2012).
Dwivedi, Y., H. S. Rizavi, et al. "Modulation in activation and expression of phosphatase and tensin homolog on chromosome ten, Aktl, and 3-phosphoinositide-dependent kinase 1: further evidence demonstrating altered phosphoinositide 3-kinase signaling in post-mortem brain of suicide subjects" Biol Psychiatry 67(11): 1017-1025 (2010).
Falcone et al. (2010) "Serum S100B: A Potential Biomarker for Suicidality in Adolescents?" PLoS One 5(6): e11089.
Falcone et al. (2010) "Serum S1OOB: A Potential Biomarker for Suicidality in Adolescents?" PLoS One 5(6): e11089.
Fiori et al., Global gene expression profiling of the polyamine system in suicide completers. Int. J. Neuropsychopharmacol. 14, 595-605, doi:10.1017/S1461145710001574 (2011).
Fiori, L. M., H. Zouk, et al. (2011). "X chromosome and suicide." Mol Psychiatry 16(2): 216-226.
Fiori, L. M., N. Mechawar, et al. "Identification and characterization of spermidine/spermine N1-acetyltransferase promoter variants in suicide completers." Biol Psychiatry 66(5): 460-467 (2009).
Fiori. L. M. and G. Turecki "Epigenetic regulation of spermidinelspermine N acetyltransferase (SATI) in suicide." J Psychiatr Res 45(9): 1229-1235 (2011).
Fiori. L. M.. B. Wanner. et al. "Association of polyaminergic loci with anxiety, mood disorders, and attempted suicide." PLoS One 5(11): e15146 (2010).
Gaiteri C, Guilloux JP, Lewis DA, Sibille E. Altered gene synchrony suggests a combined hormone-mediated dysregulated state in major depression. PLoS One; 5(4): e9970.
Galfalvy, H., G. Zalsman, et al. (2013). "A pilot genome wide association and gene expression array study of suicide with and without major depression." World J Biol Psychiatry.
Guipponi, M., S. Deutsch, et al. (2008). "Genetic and epigenetic analysis of SSAT gene dysregulation in suicidal behavior." Am J Med Genet B Neuropsychiatr Genet 150B(6): 799-807.
Hakak Y, Walker JR, Li C, Wong WH, Davis KL, Buxbaum JD et al. Genome-wide expression analysis reveals dysregulation of myelination-related genes in chronic schizophrenia. Proc Natl Acad Sci U S A 2001; 98(8): 4746-4751.
International Preliminary Report on Patentability received for PCT Patent Application No. PCT/US2016/036985, dated Dec. 21, 2017, 12 pages.
International Preliminary Report on Patentability received for PCT Patent Application No. PCT/US2018/032540, dated Nov. 21, 2019, 9 pages.
International Search Report and Written Opinion received for PCT Patent Application No. PCT/US2016/036985, dated Sep. 9, 2016, 12 pages.
International Search Report and Written Opinion received for PCT Patent Application No. PCT/US2018/032540, dated Sep. 14, 2018, 11 pages.
Karege F, Perroud N, Burkhardt S, Fernandez R, Ballmann E, La Harpe R et al. Alterations in phosphatidylinositol 3-kinase activity and PTEN phosphatase in the prefrontal cortex of depressed suicide victims. Neuropsychobiology 2011; 63(4): 224-231.
Karege F. et al., Alteration in kinase activity but not in protein levels of protein kinase B and glycogen synthase kinase-3beta in ventral prefrontal cortex of depressed suicide victims. Biol Psychiatry 61, 240-245, doi:10.1016/j.biopsych.2006.04.036 (2007).
Kelleher, I., F. Lynch, et al. (2012). "Psychotic Symptoms in Adolescence Index Risk for Suicidal Behavior: Findings From 2 Population-Based Case-Control Clinical Interview Studies." Arch Gen Psychiatry: 1-7.
Kim, S., K. H. Choi, et al. (2007). "Suicide candidate genes associated with bipolar disorder and schizophrenia: an exploratory gene expression profiling analysis of post-mortem prefrontal cortex." BMC Genomics 8: 413.
Klempan, T. A., A. Sequeira, et al. (2009). "Altered expression of genes involved in ATP biosynthesis and GABAergic neurotransmission in the ventral prefrontal cortex of suicides with and without major depression." Mol Psychiatry 14(2): 175-189.
Klempan, T. A., D. Rujescu, et al. (2008). "Profiling brain expression of the spermidine/spermine N1-acetyltransferase 1 (SAT1) gene in suicide." Am J Med Genet B Neuropsychiatr Genet 150B(7): 934-943.
Kurian S.M. et al., "Identification of blood biomarkers for psychosis using convergent functional genomics," Molecular Psychiatry 16, 37-58, doi:10.1038/mp.2009.117 (2011).
Lalovic, A., T. Klempan, et al. (2010). "Altered expression of lipid metabolism and immune response genes in the frontal cortex of suicide completers." J Affect Disord 120(1-3): 24-31.
Le-Niculescu H. et al., "Discovery and validation of blood biomarkers for suicidality", Molecular Psychiatry (2013), pp. 1-16.
Le-Niculescu H. et al., "Identifying blood biomarkers for mood disorders using convergent functional genomics," Molecular Psychiatry 14, 156-174, doi:10.1111/ele.12064 (2009).
Le-Niculescu H. et al., "Phenomic, convergent functional genomic, and biomarker studies in a stress-reactive genetic animal model of bipolar disorder and co-morbid alcoholism," American Journal of Medical Genetics, Part B, Neuropsychiatric genetics: the official publication of the International Society of Psychiatric Genetics 147B, 134-166, doi:10.1002/ajmg.b.30707 (2008).
Le-Niculescu, H., N. J. Case, et al. (2011). "Convergent functional genomic studies of omega-3 fatty acids in stress reactivity, bipolar disorder and alcoholism." Translational Psychiatry 1: e4.
Le-Niculescu, H., S. D. Patel, et al. (2009). "Convergent functional genomics of genome-wide association data for bipolar disorder: comprehensive identification of candidate genes, pathways and mechanisms." American journal of medical genetics. Part B, Neuropsychiatric genetics : the official publication of the International Society of Psychiatric Genetics 150B(2): 155-181.
Le-Niculescu, H., S. D. Patel, et at. (2010). "Convergent integration of animal model and human studies of bipolar disorder (manic-depressive illness)." Curr Opin Pharmacol 10(5): 594-600.
Le-Niculescu, H., Y. Balaraman, et al. (2007). "Towards understanding the schizophrenia code: an expanded convergent functional genomics approach." American journal of medical genetics. Part B, Neuropsychiatric genetics : the official publication of the International Society of Psychiatric Genetics 144B(2): 129-158.
Lewis M.D. et al., "Suicide deaths of active-duty US military and omega-3 fatty-acid status: a case-control comparison," J Clin Psychiatry 72, 1585-1590, doi:10.4088/JCP.11m06879 (2011).
Lowthert et al., Increased ratio of anti-apoptotic to pro-apoptotic Bcl2 gene-family members in lithium-responders one month after treatment initiation. Biology of Mood & Anxiety Disorders 2, 15, doi:10.1186/2045-5380-2-15 (2012).

(56) References Cited

OTHER PUBLICATIONS

Malkesman et al. Targeting the BH3-interacting domain death agonist to develop mechanistically unique antidepressants. Mol. Psychiatry 17, 770-780, doi:10.1038/mp.2011.77 (2012).
Margoob et al. (2004) "Serum Cholesterol Level and Suicidal Attempts—Kashmir Scenario" JK—Practitioner 11 (3):171-177.
Menke, A., K. Domschke, et al. (2012). "Genome-wide association study of antidepressant treatment-emergent suicidal ideation." Neuropsychopharmacology 37(3): 797-807.
Miller BH, Zeier Z, Xi L, Lanz TA, Deng S, Strathmann Jet al. MicroRNA-132 dysregulation in schizophrenia has implications for both neurodevelopment and adult brain function. Proc Natl Acad Sci US A 2012; 109(8): 3125-3130.
Min et al., Altered levels of growth-related and novel gene transcripts in reproductive and other tissues of female mice overexpressing spermidien/spermine N1-actyltransferase (SSAT). J. Biol. Chem. 277, 3647-3657, doi:10.1074/jbc.M100751200 (2002).
Mudge et al., Genomic Convergence Analysis of Schizophrenia: mRNA Sequencing Reveals Altered Synaptic Vesicular Transport in Post-Mortem Cerebellum, PLoS One, (2008) 11(3):e3625.
Mudge J, Miller NA, Khrebtukova I, Lindquist IE, May GD, Huntley JJ et al. Genomic convergence analysis of schizophrenia: mRNA sequencing reveals altered synaptic vesicular transport in post-mortem cerebellum. PLoS One 2008; 3(11): e3625.
Niculescu AB et al., Genetic testing may improve suicide risk prediction, Mol Psychiatry Sep. 2017, https://www.jwatch.org/na44861/2017/09/06/genetic-testing-may-improve-suicide-risk-prediction.
Niculescu et al., "Dissecting Suicidality Using a Combined Genomic and Clinical Approach," Neuropsychopharmacology, (2017), 42:360-378.
Niculescu et al., "Effects of p21Cip11/Waf1 at Both the G1/S and the G2/M Cell Cycle Transitions: pRb Is a Critical Determinant in Blocking DNA Replication and in Preventing Endoreduplication," Molecular and cellular biology, (1998), 18(1):629-643.
Niculescu et al., Psychiatric blood biomarkers: avoiding jumping to premature negative or positive conclusions, Mol. Psychiatry, (2015), 20(3):286-288.
Niculescu et al., "Understanding and predicting suicidality using a combined genomic and clinical risk assessment approach," Molecular Psychiatry, (2015), 20:1266-1285.
Niculescu et al., Precision medicine for suicidality: from universality to subtypes and personalization, Molecular Psychiatry, (2017), 22:1250-1273.
Niculescu, A. B. and H. Le-Niculescu (2010). "Convergent Functional Genomics: what we have learned and can learn about genes, pathways, and mechanisms." Neuropsychopharmacology 35(1): 355-356.
Niculescu, A. B., 3rd, D.S. Segal, et al. (2000). "Identifying a series of candidate genes for mania and psychosis: a convergent functional genomics approach." Physiological genomics 4(1): 83-91.
Niculescu, et al., PhenoChipping of psychotic disorders: a novel approach for deconstructing and quantitating psychiatric phenotypes. American Journal of Medical Genetics. Part B, Neuropsychiatric genetics: the official publication of the International Society of Psychiatric Genetics 141B, 653-662, doi:10.1002/ajmg.b.30404 (2006).
Nock, M. K., G. Borges, et al. (2008). "Suicide and suicidal behavior." Epidemiol Rev 30: 133-154.
Ogden, C. A., M. E. Rich, et at. (2004). "Candidate genes, pathways and mechanisms for bipolar (manic-depressive) and related disorders: an expanded convergent functional genomics approach." Molecular psychiatry 9(11): 1007-1029.
Oquendo et al., "Toward a Biosignature for Suicide," Am. J. Psychiatry, (2014) 171(12):1259-1277.
Oquendo, M.A., D. Currier, et al. (2010). "Increased risk for suicidal behavior in comorbid bipolar disorder and alcohol use disorders: results from the National Epidemiologic Survey on Alcohol and Related Conditions (NESARC)." The Journal of clinical psychiatry 71(7): 902-909.
Owens, Predictors of suicidal behavior found in blood, Nature, doi:10.1038/nature.2013.13570; Aug. 20, 2013. Available at http://www.nature.com/news/predictors-of-suicidal-behaviour-found-in-blood-1.13570.
Pandey, G. N., H. S. Rizavi, et al. (2012). "Proinflammatory cytokines in the prefrontal cortex of teenage suicide victims." J Psychiatr Res 46(1): 57-63.
Pandey, G. N., Y. Dwivedi, et al. (2003). "Altered expression and phosphorylation of myristoylated alanine-rich C kinase substrate (MARCKS) in postmortem brain of suicide victims with or without depression." J Psychiatr Res 37(5): 421-432.
Patel S.D. et al., "Coming to grips with complex disorders: genetic risk prediction in bipolar disorder using panels of genes identified through convergence functional genomics," American Journal of Medical Genetics Part b, Neuropsychiatric genetics: the official publication of the International Society of Psychiatric genetics 153B, 850-877, doi:10.1pp2/ajmg.b.31087 (2010).
Pietila et al., Activation of polyamine catabolism profoundly alters tissue polyamine pools and affects hair growth and female fertility in transgenic mice overexpressing spermidine/spermine N1-acetyltransferase. J. Biol. Chem. 272, 18746-18751 (1997).
Sequeira A. et al., Gene expression changes in the prefrontal cortex, anterior cingulate cortex and nucleus accumbens of mood disorders subjects that committed suicide, PioS one 7, e35367, doi:10,1371/journal.pone.0035367 (2012).
Sequeira, A., F. Mamdani, et al. (2009). "Global brain gene expression analysis links glutamatergic and GABAergic alterations to suicide and major depression." PLoS One 4(8): e6585 (2010).
Sequeira, A., T. Klempan, et al. (2007). "Patterns of gene expression in the limbic system of suicides with and without major depression." Mol Psychiatry 12(7): 640-655.
Sequeira. A., F. G. Gwadry, et al. (2006). "Implication of SSAT by gene expression and genetic variation in suicide and major depression." Arch Gen Psychiatry 63(1): 35-48.
Sublette M. et al., "Omega-3 polyunsaturated essential fatty acid status as a predictor of future suicide risk," Am J Psychiatry 163, 1100-1102, doi:10.1176/appi.ajp.163.6.110 (2006).
Supplementary European search report dated Jan. 21, 2019 for EP Application No. 16808423.

* cited by examiner

Suicidal Ideation (SI)
from Hamilton Rating Scale for Depression (HAMD).
No SI-score of 0; High SI-score of 2 or above

Suicide
0 = Absent
1 = Feels life is not worth living
2 = Wishes he were dead or any thoughts of possible death to self
3 = Suicidal ideas or gesture
4 = Attempts at suicide (any serious attempt rates 4)

FIG. 1A

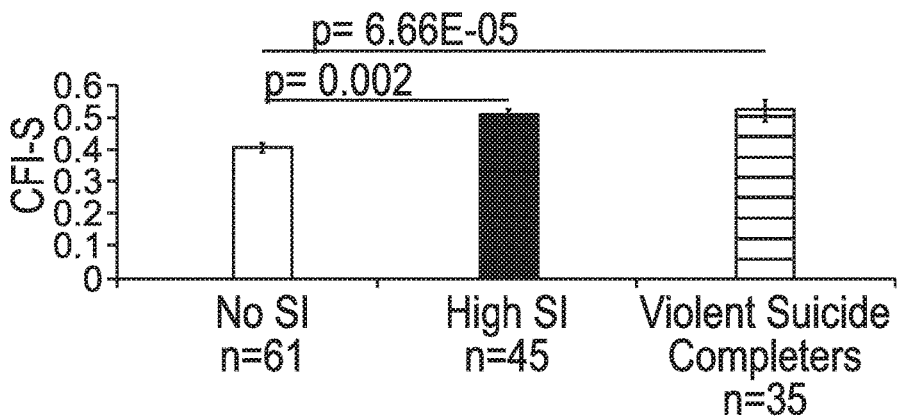
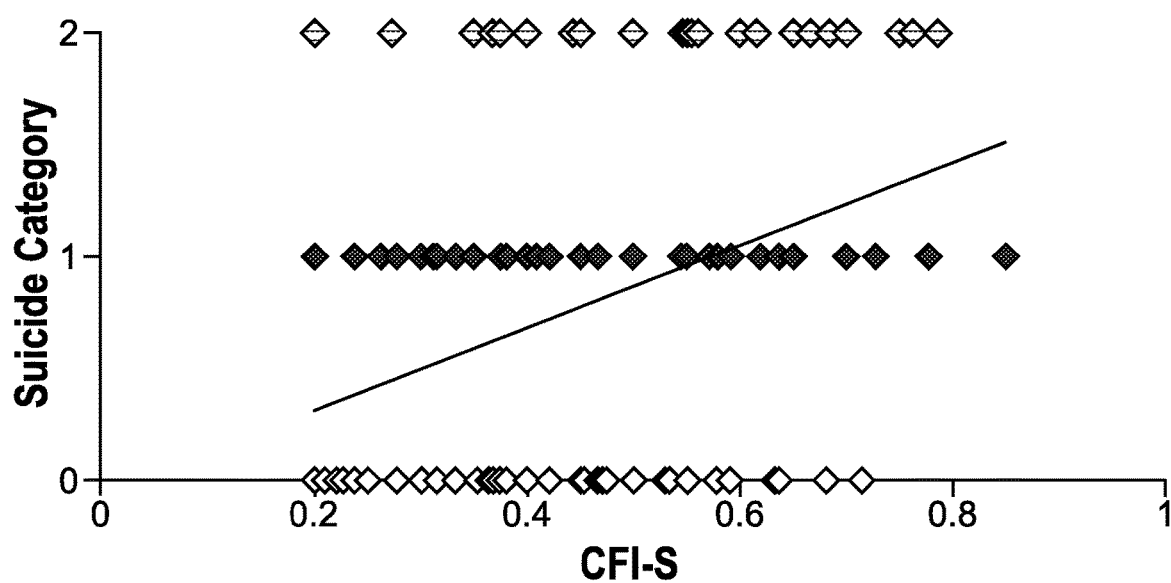
FIG. 3A

Validation of items

| CFI-S Item | Description | P-Value (One-Way ANOVA) No SI vs High SI vs Completers | Stepwise | T-Test (two tailed) High SI vs Completers |
|---|---|---|---|---|
| 18 | Lack of coping skills (cracks under pressure) | 3.35E-11 | Y | 2.42E-05 |
| 10 | Dissatisfaction with present life | 2.77E-06 | Y | 0.06804 |
| 11 | Lack of hope for the future | 3.28E-05 | Y | 7.28E-05 |
| 12 | Current substance abuse | 0.000125 | Y | 0.01273 |
| 7 | Acute stress: losses, grief | 0.000945 | Y | 0.07253 |
| 16 | Chronic stress: lack of positive relationships, social isolation | 0.0149 | Y | 0.2897 |
| 15 | Acute stress: rejection | 0.03 | Y | 0.02242 |
| 17 | History of excessive extroversion and impulsive behaviors (including rage, anger, physical fights, seeking revenge) | 0.0607 | Y | 0.2097 |
| 6 | Acute/severe medical illness, pain | 0.0892 | Y | 0.1113 |
| 19 | Lack of children | 0.365 | Y | 0.2479 |
| 22 | Gender: Male | No females | No females | No females |
| 4 | Personally knowing somebody who committed suicide | No data for completers | No data for completers | No data for completers |
| 1 | Psychiatric illness diagnosed and treated | 5.06E-15 | N | 6.02E-06 |
| 13 | Past history of suicidal acts/gestures | 2.40E-05 | N | 4.46E-05 |
| 21 | Age: Older >60 or Younger <25 | 8.89E-05 | N | 0.000267 |

FIG. 3B

| 5 | History of abuse: physical, sexual, emotional, neglect | 0.0165 | N | 0.004361 |
|---|---|---|---|---|
| 20 | History of command hallucinations of self-directed violence | 0.0397 | N | 0.009659 |
| 3 | Family history of suicide in blood relatives | 0.0797 | N | 0.0242 |
| 2 | With poor treatment compliance | 0.147 | N | 0.07321 |
| 14 | Lack of religious beliefs | 0.117 | N | 0.06151 |
| 9 | History of excessive introversion, conscientiousness | 0.303 | N | 0.2439 |
| 8 | Chronic stress: perceived uselessness, not feeling needed, burden to extended kin | 0.42 | N | 0.2097 |

FIG. 3C

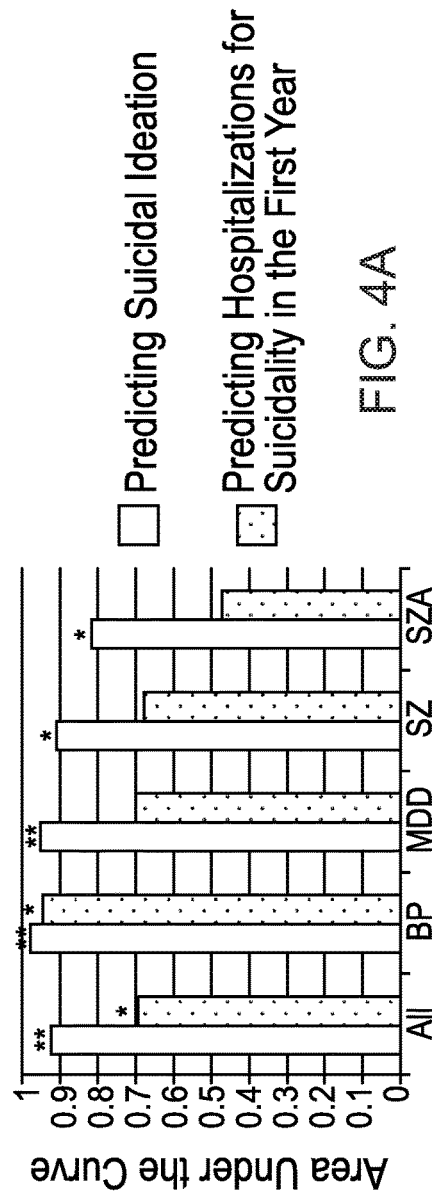

FIG. 4A

| | Subjects Total/ High SI | High SI prediction ROC AUC ROC p-value | ANOVA (No SI vs. Intermediate SI vs. High SI) | Correlation R P-value | Subjects Total/ First year hospitalized for suicidality/All future hospitalized due to suicidality | Predictions First year hospitalized for suicidality ROC AUC ROC p-value | T-test First year hospitalized for suicidality | Correlation R P-value First Year hospitalized for suicidality | Correlation R P-value All future hospitalized due to suicidality |
|---|---|---|---|---|---|---|---|---|---|
| All | 108/23 | 0.919 8.12E-15 | 6.25E-22 | 0.60019 3.26E-23 | 157/18/35 | 0.695 0.0124 | 0.0235 | 0.2093 0.0043 | 0.1911 0.0083 |
| BP | 29/7 | 0.975 1.19E-06 | 2.46E-13 | 0.81626 3.33E-16 | 50/7/9 | 0.943 0.002 | 0.002 | 0.3692 0.0042 | 0.2324 0.0522 |
| MDD | 25/8 | 0.949 2.96E-07 | NA | 0.62052 9.87E-07 | 23/3/3 | 0.700 0.155 | 0.169 | 0.2118 0.1660 | 0.1759 0.2111 |
| SZ | 26/2 | 0.908 1.46E-03 | 0.00065 | 0.48837 5.81E-05 | 44/5/8 | 0.676 0.173 | 0.287 | 0.1669 0.1517 | 0.1762 0.1385 |
| SZA | 28/6 | 0.814 1.78E-03 | 0.00271 | 0.4274 5.68E-04 | 40/3/15 | 0.480 0.552 | 0.528 | -0.0082 0.5209 | 0.1643 0.1433 |

FIG. 4B

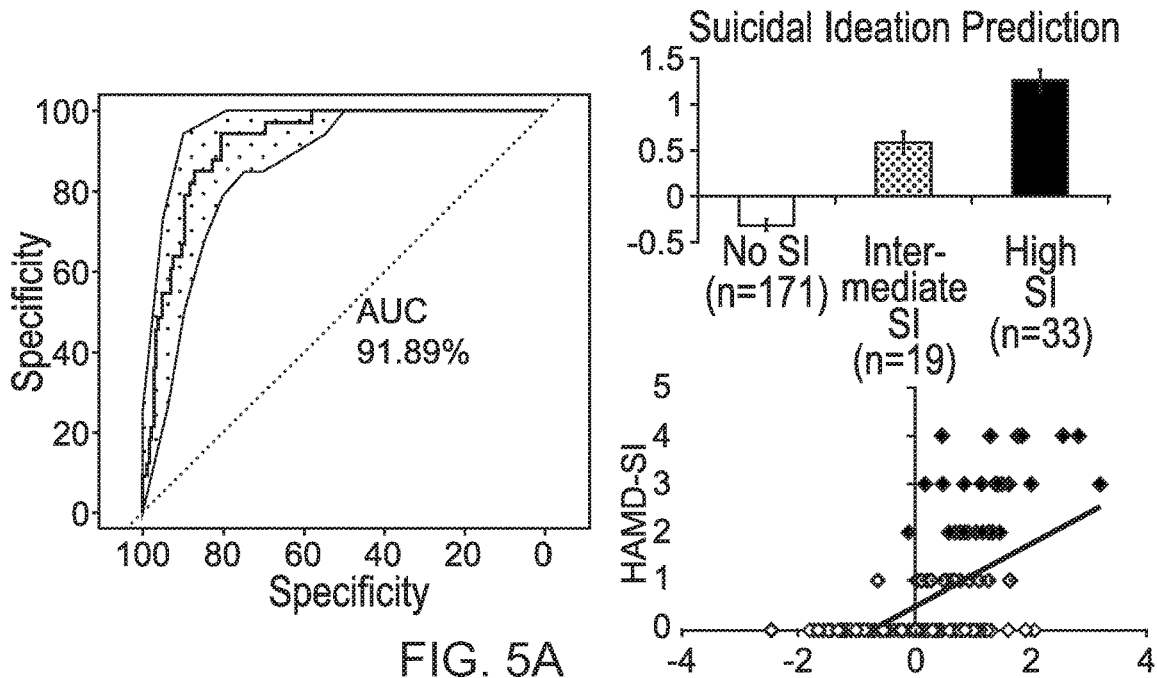
FIG. 5A
| Predictor | Dx | Type | ROC AUC | ROC p-value | ANOVA | Correlation R | Correlation p-value |
|---|---|---|---|---|---|---|---|
| UP-Suicide | All | S | 0.91898 | 8.12E-15 | 6.25E-22 | 0.6001871 | 3.26e-23 |
FIG. 5B
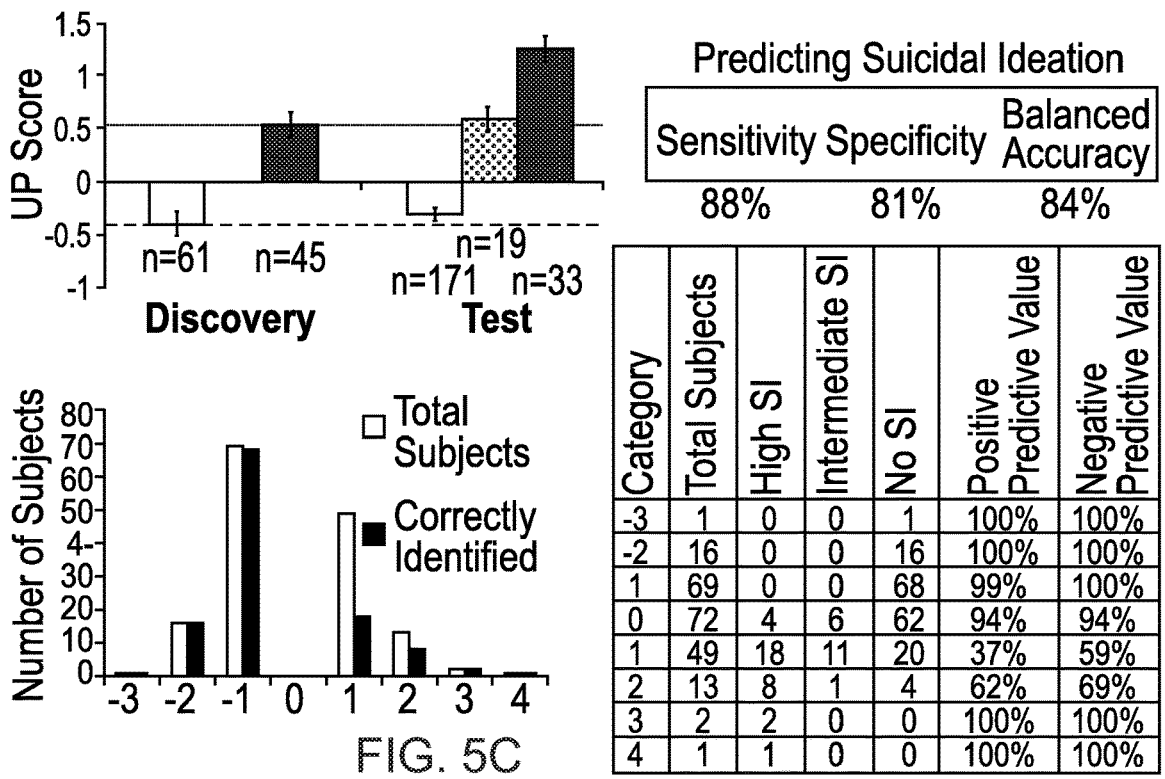
FIG. 5C

FIG. 6A

Simplifed Affective State Scale (SASS)
For each item, mark the scale with a vertical line where you think you are at this moment in time, compared to lowest and highest you ever remember being:

<u>Mood Subscale</u>

1) Mood

How good is your mood right now?

Lowest                                                                                           Highest

2) Motivation to do things

How is your motivation, your drive, your determination to do things right now?

Lowest                                                                                           Highest

3) Movement activity

How high is your physical energy and the amount of moving about that you feel like doing right now?

Lowest                                                                                           Highest

4) Thinking activity

How high is your mental energy and thinking activity going on in your mind right now?

Lowest                                                                                           Highest

FIG. 6B

5) Self-esteem

How good do you feel about yourself and your accomplishments right now?

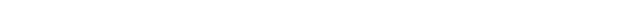
Lowest　　　　　　　　　　　　　　　　　　　　　　Highest

6) Interest in pleasurable activities

How high is your interest to do things that are fun and enjoyable right now?

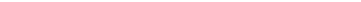
Lowest　　　　　　　　　　　　　　　　　　　　　　Highest

7) Appetite

How high is your appetite and desire for food right now?

[------------------------------------------------------------]
Lowest　　　　　　　　　　　　　　　　　　　　　　Highest Anxiety Subscale

1) Anxiety

How anxious are you right now?

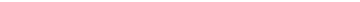
Lowest　　　　　　　　　　　　　　　　　　　　　　Highest

2) Uncertainty

How uncertain about things do you feel right now?

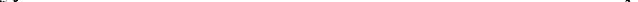
Lowest　　　　　　　　　　　　　　　　　　　　　　Highest

3) Fear

How frightened about things do you feel right now?

FIG. 6C
Lowest                                              Highest
4) Anger
How angry about things do you feel right now?
Lowest                                              Highest
Comments (optional):
Describe events or actions that you think are influencing how you feel now. Describe any additional feelings you might have at this moment in time:

|  |  | Ingenuity Pathways | | | KEGG Pathways | | | GeneGO Pathways | | |
|---|---|---|---|---|---|---|---|---|---|---|
|  |  | Top Canonical Pathways | P-Value | Ratio | Pathway Name | Enrichment Score | Enrichment p-value | Process Networks | Ratio | p-value |
| Non-Validated in Compl eters Stepwi se (n=208 genes) | 1 | G-Protein Coupled Receptor Signaling | 2.28 E-08 | 5.7% 15/264 | Pathogenic Escherichia coli infection | 7.19808 | 0.000748 | Cytoskeleton_ Regulation of cytoskeleton rearrangement | 16/ 183 | 5.75E-07 |
|  | 2 | cAMP-mediated signaling | 1.51 E-07 | 5.8% 13/223 | Amoebiasis | 5.51218 | 0.004037 | Development_ Neurogenesis_Ax onal guidance | 17/ 230 | 2.65E-06 |
|  | 3 | CREB Signaling in Neurons | 6.20 E-06 | 5.6% 10/179 | Dorso-ventral axis formation | 4.7856 | 0.006349 | Development_ Hedgehog signaling | 17/ 254 | 1.01E-05 |
|  | 4 | Cardiac Hypertrophy Signaling | 1.02 E-05 | 4.7% 11/232 | Melanogenesis | 4.31121 | 0.013417 | Reproduction_ Progesterone signaling | 14/ 214 | 8.25E-05 |
|  | 5 | Synaptic Long Term Potentiation | 2.26 E-05 | 6.3% 8/127 | Influenza A | 4.23564 | 0.014471 | Cardiac development_ Wnt_beta-catenin, Notch, VEGF, IP3 and integrin signaling | 11/ 150 | 0.000 1819 |
|  |  | Top Canonical Pathways | P-Value | Ratio | Pathway Name | Enrichment Score | Enrichment p-value | Process Networks | Ratio | p-value |
| Validat | 1 | B Cell Receptor Signaling | 1.01 | 7.2 % 13/ | Focal adhesion | 10.5307 | 2.67E-05 | Signal transduction_ | 19/ 177 | 8.10E-10 |

FIG. 8B

| | | | | | | | | WNT signaling | | |
|---|---|---|---|---|---|---|---|---|---|---|
| ed in Completers Stepwi se (n=204 genes) | 2 | Ovarian Cancer Signaling | 3.31 E-08 | 8.3 % 11/133 | Colorectal cancer | 10.3054 | 3.35E-05 | Cell cycle_ G1-S Growth factor regulation | 18/ 195 | 2.62E-08 |
| | 3 | Glucocorticoid Receptor Signaling | 3.97 E-08 | 5.3 % 15/281 | GABAergic synapse | 8.60276 | 0.000184 | Reproduction_ Gonadotropin regulation | 18/ 199 | 3.60E-06 |
| | 4 | Colorectal Cancer Metastasis Signaling | 4.00 E-08 | 5.8 % 14/241 | mTOR signaling pathway | 8.47678 | 0.000208 | Reproduction_ GnRH signaling pathway | 16/ 166 | 9.05E-06 |
| | 5 | G12/13 Signaling | 1.12 E-07 | 8.5 % 10/118 | Chagas disease (American trypanosomiasis) | 7.66796 | 0.000468 | Neurophysiological process_ Transmission of nerve impulse | 18/ 212 | 9.58E-06 |

FIG. 8C

| | | Ingenuity | | | GeneGO | | |
|---|---|---|---|---|---|---|---|
| | | Diseases and Disorders | P-Value | # Molecules | Diseases | pValue | Ratio |
| Non-Validated in Complete rs Stepwise (n=208 genes) | 1 | Neurological disease | 5.43E-04 - 8.63E-13 | 78 | Psychiatry and Psychology | 1.6E-30 | 85/1919 |
| | 2 | Psychological Disorders | 1.77E-04 - 2.04E-12 | 62 | Mental Disorders | 2.82E-30 | 78/1614 |
| | 3 | Skeletal and Muscular Disorders | 1.98E-04 - 5.33E-10 | 60 | Schizophrenia | 3.6E-22 | 51/914 |
| | 4 | Organismal Injury and Abnormalities | 6.69E-04 - 1.81E-09 | 184 | Schizophrenia and Disorders with Psychotic Features | 4.37E-22 | 51/918 |
| | 5 | Cancer | 6.32E-04 - 2.59E-09 | 182 | Central Nervous System Diseases | 5.41E-22 | 94/3069 |
| | | Diseases and Disorders | P-Value | # Molecules | Diseases | pValue | Ratio |
| Validated in Complete rs Stepwise (n=294 genes) | 1 | Organismal Injury and Abnormalitie | ≤ 2.11E-04 - 1.23E-13 | 178 | Psychiatry and Psychology | 1.77E-23 | 76/1919 |
| | 2 | Cancer | 2.20E-04 - 5.41E-13 | 176 | Mental Disorders | 1.23E-21 | 67/1614 |
| | 3 | Neurological Disease | 1.31E-04 - 1.07E-12 | 81 | Mood Disorders | 4.02E-21 | 47/797 |
| | 4 | Psychological Disorders | 1.31E-04 - 1.07E-12 | 63 | Depressive Disorder, Major | 1.06E-18 | 37/546 |
| | 5 | Tumor Morphology | 1.87E-04 - 1.83E-12 | 38 | Depressive Disorder | 2.44E-18 | 37/560 |

FIG. 9

| Gene Symbol/ Affymetrix Probeset ID | Males | | | | |
|---|---|---|---|---|---|
| | Top Biomarkers All diagnoses | Top Biomarkers Bipolar disorder (BP) | Top Biomarkers Depression (MDD) | Top Biomarkers Schizoaffective disorder (SZA) | Top Biomarkers Schizophrenia (SZ) |
| Top Discovery AP Increased | DTNA 211493_x_at | DTNA 211493_x_at | PHF20 210500_at | USP48 232621_at | RP11-389C8.2 1556314_a_at |
| Top Discovery AP Decreased | KIF2C 211519_s_at | HS3ST3B1 1561908_a_at | EIF1B-AS1 1557212_at | NPRL3 210672_s_at | CYB561 210816_s_at |
| Top Discovery DE Increased | CADM1 237259_at | CADM1 237259_at | TLN1 232763_at | TSPYL1, 1560648_s_at | LOC100128288 1559045_at |
| Top Discovery DE Decreased | CLIP4 219944_at | Unknown gene 231262_at | NUCKS1 229353_s_at | TMSB15B, 1556964_s_at MCM8, 231827_at | CCDC163P 1559003_a_at |
| Top Prioritization AP Increased | SLC4A4 210739_x_at | KSR1 213769_at | DLK1 209560_s_at | IL6 205207_at | C1orf61 205103_at |
| Top Prioritization AP Decreased | SKA2 225686_at | CD44 216056_at | BBIP1 232910_at | TNS1 218863_s_at | SKA2 225686_at |
| Top Prioritization DE Increased | SAT1 210592_s_at | DAPP1 219290_x_at | BDNF 229353_s_at | TNF 207113_s_at | BDNF 206382_s_at |
| Top Prioritization DE Decreased | SKA2 225686_at | OPRM1 207989_at | SKA2 225686_at | S100B 1561521_at | HTR2A 211616_s_at |
| Top Validation AP Increased | IL6 205207_at | SPTBN1 215918_s_at | IL10 207433_at | JUN 201466_s_at | SLC5A3 1553313_s_at |
| Top Validation AP Decreased | MBP 225408_at | AKT1S1 224982_at | EIF1BAS1 1557212_at | BATF2 228439_at | ATP6V0E1 236527_at |
| Top Validation DE Increased | JUN 201464_x_at | SAT1 213988_s_at | GATM 1566861_at | JUN 201464_x_at | JUN 201464_x_at |
| Top Validation DE Decreased | KLHDC3 214383_x_at | C20orf27 218081_at | PRPF40A 226687_at | ANXA11 228727_at | LOC100131662 236973_at |

Suicidal Ideation (SI)
from Hamilton Rating Scale for Depression (HAMD).
No SI-score of 0; High SI-score of 2 or above

Suicide
0 = Absent
1 = Feels life is not worth living
2 = Wishes he were dead or any thoughts of possible death to self
3 = Suicidal ideas or gesture
4 = Attempts at suicide (any serious attempt rates 4)

| 14 | Lack of religious beliefs | Y | 0.0175 |
|---|---|---|---|
| 13 | Past history of suicidal acts/gestures | Y | 0.0253 |
| 15 | Acute stress: Rejection (within last 3 months) | Y | 0.0294 |
| 20 | History of command hallucinations of self-directed violence | Y | 0.0453 |
| 10 | Dissatisfaction with life at this moment in time | Y | 0.0583 |
| 8 | Chronic stress: perceived uselessness, not feeeling needed, burden to extended kin | Y | 0.0635 |
| 4 | Personally knowing somebody who committed suicide | Y | 0.0733 |
| 7 | Acute stress: losses, grief (within last 3 months) | Y | 0.0748 |
| 3 | Family history of suicide in blood relatives | Y | 0.1422 |
| 21 | Age:Older >60 or Younger <25 | Y | 0.2374 |
| 2 | With poor treatment compliance | Y | 0.2477 |
| 6 | Acute/severe medical illness, including acute pain ("I just can't stand this pain anymore.") (within last 3 months) | Y | 0.2714 |
| 5 | History of abuse: physical, sexual, emotional, neglect | Y | 0.3348 |
| 9 | History of excessive introversion, conscientiousness (including planned suicide attempts) | Y | 0.3388 |
| 18 | Lack of coping skills when faced with stress (cracks under pressure) | Y | 0.3723 |
| 19 | Lack of children. If has children, not in touch/not helping take care of them | N | 0.0714 |
| 1 | Psychiatric illness diagnosed and treated | All have dx | All have dx |
| 11 | Lack of hope for the future | No difference | 1 |
| 22 | Gender: Male | All females | All females |

FIG. 12B

| 10 | Dissatisfaction with life at this moment in time | Y | 2.12E-08 |
|---|---|---|---|
| 18 | Lack of coping skills when faced with stress (cracks under pressure) | Y | 2.93E-07 |
| 9 | History of excessive introversion, conscientiousness (including planned suicide attempts) | Y | 1.73E-06 |
| 7 | Acute stress: losses, grief (within last 3 months) | Y | 0.0005 |
| 20 | History of command hallucinations of self-directed violence | Y | 0.0006 |
| 15 | Acute stress: Rejection (within last 3 months) | Y | 0.0012 |
| 3 | Family history of suicide in blood relatives | Y | 0.0012 |
| 2 | With poor treatment compliance | Y | 0.0013 |
| 8 | Chronic stress: perceived uselessness, not feeeling needed, burden to extended kin | Y | 0.0014 |
| 11 | Lack of hope for the future | Y | 0.0063 |
| 17 | History of excessive extroversion and impulsive behaviors (including rage, anger, physical fights, seeking revenge) | Y | 0.0095 |
| 4 | Personally knowing somebody who committed suicide | Y | 0.0216 |
| 12 | Current substance abuse | Y | 0.0216 |
| 19 | Lack of children. If has children, not in touch/not helping take care of them. | Y | 0.0447 |
| 6 | Acute/severe medical illness, including acute pain ("I just can't stand this pain anymore.") (within last 3 months) | Y | 0.0568 |
| 5 | History of abuse: physical, sexual, emotional, neglect | Y | 0.752 |
| 21 | Age: Older >60 or Younger <25 | Y | 0.0775 |
| 14 | Lack of religious beliefs | Y | 0.0896 |
| 1 | Psychiatric illness diagnosed and treated | All have dx | All have dx |
| 22 | Gender: Male | All males | All males |

FIG. 12D

| | Partici-pants | Diagnosis | Ethnicity | Age (All Visits) Mean | T-test for age | |
|---|---|---|---|---|---|---|
| Discovery Cohort (Within-Participant Changes in Suicidal Ideation) | 12 | BP =4<br>MDD=4<br>SZA=3<br>SZ=1 | EA=9<br>AA=2<br>Asian=1 | All=44.39 (11.65)<br>No SI=44.56<br>High SI=44.15 | T-test for age between No SI and High SI 0.926 | |
| Independent Validation Cohort for Gene Expression (Suicide Completers) | 6 | BP=1<br>MDD=3<br>PTSD=1<br>Non-Psychiatric=1 | EA=5<br>AA=1 | 43.5 (14.24) | | T-test for age with Discovery Cohort P=0.890 |
| Independent Testing Cohort For State Predictions (Suicidal Ideation) | 33 | All<br>BP=17<br>MDD=7<br>SZA=7<br>SZ=2<br>No SI<br>BP=13<br>MDD=4<br>SZA=6<br>SZ=2<br>Intermediate SI<br>BP=3<br>SZA=1<br>High SI<br>BP=3<br>MDD=3<br>SZA=1 | EA=26<br>AA=5<br>Asian=1<br>Mixed=1 | All=44.05 (8.81)<br>No SI =43.98<br>High SI =41.28 | T-test for age between No SI and High SI 0.553 | T-test for age with Discovery Cohort P=0.887 |
| Combined Discovery and Testing Cohort For State (Suicidal Ideation) Used for CFI-S analysis (Figure 3) | 45 | All<br>BP=21<br>MDD=11<br>SZA=10<br>SZ=3<br>No SI<br>BP=17<br>MDD=8<br>SZA=9<br>SZ=3<br>Intermediate SI<br>BP=3<br>SZA=1 | EA=35<br>AA=7<br>Asian=2<br>Mixed=1 | All=44.15 (9.68)<br>No SI=44.12<br>High SI =43.15 | T-test for age between No SI and High SI 0.727 | |

FIG. 14A

| | | High SI<br>BP=7<br>MDD=7<br>SZA=4<br>SZ=1 | | | | |
|---|---|---|---|---|---|---|
| Testing Cohort for Trait Predictions (Future Hospitalizations for Suicidality) | 24 | All<br>BP=10<br>MDD=9<br>SZA=3<br>SZ=2<br>No Hosp for SI<br>BP=8<br>MDD=8<br>SZA=1<br>SZ=2<br>Hosp for SI<br>BP=2<br>MDD=1<br>SZA=2<br>SZ=0 | EA=19<br>AA=4<br>Mixed=1 | All=46.51<br>(6.66)<br>No Hosp for SI<br>=47.2<br>Hosp for SI<br>=43.4 | T-test for age between No Hosp for SI and Hosp for SI<br>0.0430 | T-test for age with Discovery Cohort<br>p=0.354 |

| | | Marker | Participants with Suicidality/ Participants Total | ROC AUC/ p-value | Pearson's Correlation R/p-value | Student's t-test p-value |
|---|---|---|---|---|---|---|
| Suicidal Ideation Cohort n=33 Participants | Best Blood Biomarkers Predictors | Out of Validated Biomarkers (Bonferroni) (49 genes, 50 probesets) | | | | |
| | | EPB41L5 | 7 \| 33 | 0.68/0.06 | 0.22/0.03 | 0.09 |
| | | HAVCR2 | 7 \| 33 | 0.62/0.15 | 0.17/0.07 | 0.18 |
| | | ARHGAP15 | 7 \| 33 | 0.55/0.34 | 0.12/0.15 | 0.22 |
| | | PIK3C3 | 7 \| 33 | 0.65/0.1 | -0.21/0.037 | 0.08368 |
| | | GTF3C2 | 7 \| 33 | 0.64/0.115 | -0.11/0.179 | 0.07208 |
| | | ALDH3A2 | 7 \| 33 | 0.62/0.142 | -0.21/0.036 | 0.1421 |
| | | Out of Top Discovery and Prioritization Biomarkers (Non Bonferroni Validated, 65 genes) | | | | |
| | | DPCD | 7 \| 33 | 0.67/0.07 | 0.21/0.04 | 0.12 |
| | | GTF3C3 | 7 \| 33 | 0.67/0.07 | 0.23/0.02 | 0.11 |
| | | ASPH | 7 \| 33 | 0.65/0.1 | 0.07/0.27 | 0.13 |
| | | ACTR3 | 7 \| 33 | 0.62/0.15 | -0.19/0.05 | 0.13 |
| | | NUDT6 | 7 \| 33 | 0.62/0.15 | -0.07/0.27 | 0.19 |
| | | LRRC8B | 7 \| 33 | 0.60/0.19 | -0.15/0.11 | 0.13 |
| | | Panels of Validated Biomarkers (Increased, Decreased, Combined) | | | | |
| | | BioM-18 | 7 \| 33 | 0.37/0.87 | 0.032/0.39 | 0.59 |

| | | Marker | BioM-32 | 7 | 33 | 0.43/0.72 | -0.0031/0.49 | 0.68 | |
|---|---|---|---|---|---|---|---|---|---|
| | | | BioM-50 | 7 | 33 | 0.5/0.515 | 0.02/0.429 | 0.465 | |
| | Clinical measures | | Anxiety | 7 | 33 | 0.72/0.029 | 0.26/0.011 | 0.0083 | |
| | | | Mood | 7 | 33 | 0.78/0.0078 | -0.37/0.0006 | 0.002 | |
| | | | SASS | 7 | 33 | 0.81/0.0035 | 0.38/0.0005 | 5.04E-05 | |
| | | | CFI-S | 7 | 29 | 0.84/0.002 | 0.39/0.0013 | 0.003 | |
| | | | CFI-S+SASS | 7 | 29 | 0.87/0.00088 | 0.48/0.0001 | 0.00027 | |
| | Combined | | UP-Suicide | 7 | 29 | 0.82/0.003 | 0.43/0.0003 | 0.001467 | |

| | | Marker | Participants Hospitalized for Suicidality/ Participants Hospitalized Total | | ROC AUC/ p-value | Pearson's Correlation R/p-value | Student's t-test p-value | Cox Regression Hazard Ratio | Cox Regression p-value |
|---|---|---|---|---|---|---|---|---|---|
| Future Hospitalizations for Suicidality n=24 Participants | Best Blood Biomarkers Predictors | Out of Validated Biomarkers (Bonferroni) (49 genes, 50 probesets) | | | | | | | |
| | | HTRA1 | 5 | 24 | 0.84/0.01 | 0.62/0.00058 | 0.02 | 4.55 | 0.01 |
| | | PER1 | 4 | 24 | 0.84/0.018 | 0.39/0.029 | 0.1314 | 1.535 | 0.1615 |
| | | PDXDC1 | 5 | 24 | 0.81/0.018 | 0.64/0.0004 | 0.04187 | 2.4436 | 0.01503 |
| | | PIK3C3 | 3 | 24 | 0.9/0.011 | -0.25/0.115 | 0.02583 | 5.995 | 0.12 |
| | | BCL2 | 4 | 24 | 0.89/0.007 | -0.35/0.047 | 0.05385 | 3.0848 | 0.01 |
| | | MOB3B | 4 | 24 | 0.85/0.015 | -0.34/0.053 | 0.000462 | 9.572 | 0.09 |
| | | Out of Top Discovery and Prioritization Biomarkers (Non Bonferroni Validated, 65 genes) | | | | | | | |

|  |  |  |  |  |  |  |  |
|---|---|---|---|---|---|---|---|
|  | KLHL28 | 5\|24 | 0.91/0.002 | 0.50/0.007 | 0.003 | 7.36 | 0.04 |
|  | UIMC1 | 5\|24 | 0.86/0.006 | 0.40/0.08 | 0.04 | 2.26 | 0.03 |
|  | SNX27 | 4\|24 | 0.85/0.02 | 0.73/2.5E-05 | 0.05 | 4.27 | 0.01 |
|  | CSNK1A1 | 4\|24 | 0.96/0.0007 | -0.27/0.10 | 0.0007 | 620.5 | 0.02 |
|  | LARP4 | 4\|24 | 0.9/0.005 | -0.3/0.08 | 6.30E-05 | 37.01 | 0.11 |
|  | ZNF548 | 5\|24 | 0.83/0.012 | -0.31/0.07 | 0.008 | 15.94 | 0.02 |
|  | Panels of Validated Biomarkers (Increased, Decreased, Combined) | | | | | | |
|  | BioM-18 | 4\|24 | 0.88/0.0088 | 0.46/0.011 | 0.033 | 27.6 | 0.021 |
|  | BioM-32 | 4\|24 | 0.71/11 | -0.34/0.053 | 0.16 | 10.57 | 0.23 |
|  | BioM-50 | 5\|24 | 0.94/0.002 | 0.54/0.003 | 0.005813 | 89.459 | 0.02 |
| Clinical measures | Anxiety | 4\|24 | 0.86/0.01 | 0.44/0.01 | 0.0039 | 14.4 | *0.061* |
|  | Mood | 3\|24 | 0.68/0.18 | -0.22/0.16 | 0.22 | 33.4 | 0.1 |
|  | SASS | 4\|24 | 0.83/0.02 | 0.39/0.03 | 0.034 | 3.72 | *0.066* |
|  | CFI-S | 3\|24 | 0.5/0.52 | 0.24/0.12 | 0.38 | 1.17 | 0.79 |
|  | CFI-S+SASS | 4\|24 | 0.74/0.08 | 0.40/0.03 | 0.083 | 4.68 | 0.06 |
| Combined | UP-Suicide | 5\|24 | 0.78/0.032 | 0.51/0.006 | 0.03691 | 9.6068 | 0.01 |

FIG. 16C

| | | | |
|---|---|---|---|
| 16 | Chronic stress: lack of positive relationships, social isolation | Y | 3.562E-15 |
| 10 | Dissatisfaction with present | Y | 6.20479E-14 |
| 18 | Lack of coping skills (cracks under pressure) | Y | 2.82E-10 |
| 8 | Chronic stress: perceived uselessness, not feeeling needed, burden to extended kin | Y | 5.41467E-06 |
| 20 | History of command hallucinations of self-directed violence | Y | 1.11225-05 |
| 9 | History of excessive introversion, conscientiousness | Y | 1.44517E-05 |
| 15 | Acute stress: Rejection | Y | 1.49128E-05 |
| 12 | Current substance abuse | Y | 1.71401E-05 |
| 7 | Acute stress: losses, grief | Y | 1.90447E-05 |
| 11 | Lack of hope for the future | Y | 5.29E-04 |
| 17 | History of excessive extroversion and impulsive behaviors (including rage, anger, physical fights, seeking revenge) | Y | 0.000540744 |
| 14 | Lack of religious beliefs | Y | 0.000754729 |
| 3 | Family history of suicide in blood relatives | Y | 0.001501435 |
| 6 | Acute/severe medical illness, pain | Y | 0.001551877 |
| 2 | With poor treatment compliance | | 0.001716147 |
| 4 | Personally knowing somebody who committed suicide | Y | 0.010376266 |
| 5 | History of abuse: physical, sexual, emotional, neglect | Y | 0.084287799 |
| 19 | Lack of children | Y | 0.393277178 |
| 21 | Age: Older >60 or Younger <25 | N | 0.111733842 |
| 22 | Gender: Male | N | 0.992968285 |
| 1 | Psychiatric illness diagnosed and treated | All have dx | All have dx |

FIG. 17B

| 15 | Acute stress: Rejection | Y | 3.60E-05 |
|---|---|---|---|
| 3 | Family history of suicide in blood relatives | Y | 1.85E-04 |
| 7 | Acute stress: losses, grief | Y | 1.31E-03 |
| 11 | Lack of hope for the future | Y | 4.46E-03 |
| 16 | Chronic stress: lack of positive relationships, social isolation | Y | 4.64E-03 |
| 18 | Lack of coping skills (cracks under pressure) | Y | 9.38E-03 |
| 10 | Dissatisfaction with present life | Y | 0.013 |
| 6 | Acute/severe medical illness, pain | Y | 0.0155 |
| 8 | Chronic stress: perceived uselessness, not feeeling needed, burden to extended kin | Y | 0.0185 |
| 4 | Personally knowing somebody who committed suicide | Y | 0.0463409 |
| 22 | Gender: Male | Y | 0.0514736 |
| 5 | History of abuse: physical, sexual, emotional, neglect | Y | 0.0904092 |
| 12 | Current substance abuse | Y | 0.100109 |
| 14 | Lack of religious beliefs | Y | 0.2170824 |
| 21 | Age: Older >60 or Younger <25 | Y | 0.2578034 |
| 2 | With poor treatment compliance | | 0.2851157 |
| 9 | History of excessive introversion, conscientiousness | Y | 0.4891344 |
| 19 | Lack of children | N | 0.2289837 |
| 17 | History of excessive extroversion and impulsive behaviors (including rage, anger, physical fights, seeking revenge) | N | 0.303751 |
| 1 | Psychiatric illness diagnosed and treated | All have dx | All have dx |

FIG. 18B

PREDICTING SUICIDALITY USING A COMBINED GENOMIC AND CLINICAL RISK ASSESSMENT

CROSS REFERENCE TO RELATED APPLICATIONS

This application is a national phase application of PCT/US2016/036985, filed Jun. 10, 2016, which claims priority to U.S. Provisional Application No. 62/278,707 filed Jan. 14, 2016 and U.S. Provisional Application No. 62/174,880 filed on Jun. 12, 2015, each of which are hereby incorporated by reference in their entireties.

STATEMENT OF GOVERNMENT SUPPORT

This invention was made with government support under OD007363 awarded by National Institutes of Health. The Government has certain rights in the invention.

BACKGROUND OF THE DISCLOSURE

The present disclosure relates generally to biomarkers and their use for predicting a subject's risk of suicidality (e.g., suicide ideation and actions, future hospitalization due to suicidality, and suicide completion). More particularly, the present disclosure relates to gene expression biomarkers, and to methods of screening for biomarkers, for identifying subjects who are at risk of committing suicide, as well as for preventing and treating subjects for suicidality. The present disclosure further relates to quantitative clinical information assessments through questionnaires and mobile applications (referred to herein as "apps") for assessing affective state (mood and anxiety), for assessing socio-demographic and psychological suicide risk factors, and for identifying subjects who are at risk of committing suicide. Finally, the present disclosure relates to an algorithm for combining biomarkers and apps for identifying subjects who are at risk for committing suicide.

Suicide is a leading cause of death in psychiatric patients, and in society at large. Particularly, suicide accounts for one million deaths worldwide each year. Worldwide, one person dies every 40 seconds through suicide, a potentially preventable cause of death. Further, although women have a lower rate of suicide completion as compared to men, due in part to the less-violent methods used, women have a higher rate of suicide attempts. A limiting step in the ability to intervene is the lack of objective, reliable predictors. One cannot just ask individuals if they are suicidal, as the desire to not be stopped or future impulsive changes of mind may make their self-report of feelings, thoughts and plans unreliable.

There are currently no objective tools to asses and track changes in suicidal risk without asking the subjects directly. Such tools, however, could prove substantially advantageous as the subjects at risk often choose not to share their suicidal ideation or intent with others, for fear of stigma, hospitalization, or that their plans will be thwarted. The ability to asses and track changes in suicidal risk without asking a subject directly would further allow for intervening prior to suicide attempt and suicide completion by the subject.

Conventionally, a convergence of methods assessing the subject's internal subjective feelings and thoughts, along with external, more objective, ratings of actions and behaviors, are used de facto in clinical practice, albeit not in a formalized and systematic way. Accordingly, there exists a need to develop more quantitative and objective ways for predicting and tracking suicidal states. More particularly, it would be advantageous if objective tools and screening methods could be developed for determining expression levels of biomarkers to allow for determining suicidal risk and other psychotic depressed mood states, as well as monitoring a subject's response to treatments for lessening suicidal risk. The ability to asses and track changes in suicidal risk without asking a subject directly would further allow for intervening prior to suicide attempt and suicide completion by the subject.

BRIEF DESCRIPTION OF THE DISCLOSURE

The present disclosure is generally related to predicting state (suicidal ideation) and trait—future psychiatric hospitalizations for suicidality. The methods described herein increase the predictive accuracy for specifically identifying subjects who are at risk for committing suicide and for predicting future hospitalization due to suicidality. In one particular aspect, the methods described herein increase the predictive accuracy for specifically identifying subjects who are at risk for committing suicide and for predicting future hospitalization due to suicidality.

In one aspect, the present disclosure is directed to a method for predicting suicidality in a subject. The method comprises: obtaining an expression level of a blood biomarker in a sample obtained from the subject; obtaining a reference expression level of a blood biomarker; and identifying a difference between the expression level of the blood biomarker in a sample obtained from the subject and the reference expression level of a blood biomarker, wherein the difference in the expression level of the blood biomarker in the sample obtained from the subject and the reference expression level of the blood biomarker indicates a risk for suicide.

In another aspect, the present disclosure is directed to a method for mitigating suicidality in a subject in need thereof. The method comprises: obtaining an expression level of a blood biomarker in a sample obtained from the subject; obtaining a reference expression level of the blood biomarker; identifying a difference in the expression level of the blood biomarker in the sample and the reference expression level of the blood biomarker; and administering a treatment, wherein the treatment reduces the difference between the expression level of the blood biomarker in the sample and the reference expression level of the blood biomarker to mitigate suicidality in the subject.

In another aspect, the present disclosure is directed to a computer-implemented method for assessing mood, anxiety, and combinations thereof in the subject using a computer-implemented method for assessing mood, anxiety, and combinations thereof, the method implemented using a first computer device coupled to a memory device, the method comprising: receiving mood information, anxiety information, and combinations thereof into the first computer device; storing, by the first computer device, the mood information, anxiety information, and combinations thereof in the memory device; presenting, by the first computer device, in visual form the mood information, anxiety information, and combinations thereof to a second computer device; receiving a request from the second computer device for access to the mood information, anxiety information, and combinations thereof; and transmitting, by the first computer device, the mood information, anxiety information, and combinations thereof to the second computer device to assess mood, anxiety, and combinations thereof in the subject.

In another aspect, the present disclosure is directed to a computer-implemented method for assessing socio-demographic/psychological suicidal risk factors in the subject using a computer-implemented method for assessing socio-demographic/psychological suicidal risk factors in the subject, the method implemented using a first computer device coupled to a memory device, the method comprising: receiving socio-demographic/psychological suicidal risk factor information into the first computer device; storing, by the first computer device, the socio-demographic/psychological suicidal risk factor information in the memory device; presenting, by the first computer device, in visual form the socio-demographic/psychological suicidal risk factor information to a second computer device; receiving a request from the second computer device for access to socio-demographic/psychological suicidal risk factor information; and transmitting, by the first computer device, the socio-demographic/psychological suicidal risk factor information to the second computer device to assess the socio-demographic/psychological suicidal risk factors in the subject.

In one aspect, the present disclosure is directed to a method for predicting suicidality in a subject. The method comprises: identifying a difference in the expression level of a blood biomarker in a sample obtained from a subject and a reference expression level of the blood biomarker by obtaining the expression level of the blood biomarker in a sample obtained from a subject; obtaining a reference expression level of a blood biomarker; analyzing the blood biomarker in the sample obtained from the subject and the reference expression level of the blood biomarker to detect the difference between the blood biomarker in the sample and the reference expression level of the blood biomarker; assessing mood, anxiety, and combinations thereof in the subject, using a first computer device coupled to a memory device, wherein the first computer device receives mood information, anxiety information, and combinations thereof into the first computer device; storing, by the first computer device, the mood information, anxiety information, and combinations thereof in the memory device; computing, by the first computer device, of the mood information, anxiety information, and combinations thereof, a score that can be used to predict suicidality; presenting, by the first computer device, in visual form the mood information, anxiety information, and combinations thereof to a second computer device; receiving a request from the second computer device for access to the mood information, anxiety information, and combinations thereof; and transmitting, by the first computer device, the mood information, anxiety information, and combinations thereof to the second computer device to assess mood, anxiety, and combinations thereof in the subject; assessing socio-demographic/psychological suicidal risk factors in the subject using the first computer device coupled to a memory device, wherein the first computer device receives socio-demographic/psychological suicidal risk factor information into the first computer device; storing, by the first computer device, the socio-demographic/psychological suicidal risk factor information in the memory device; computing, by the first computer device, of the socio-demographic/psychological suicidal risk factor information, a score that can be used to predict suicidality; presenting, by the first computer device, in visual form the socio-demographic/psychological suicidal risk factor information to the second computer device; receiving a request from the second computer device for access to socio-demographic/psychological suicidal risk factor information; and transmitting, by the first computer device, the socio-demographic/psychological suicidal risk factor information to the second computer device to assess the socio-demographic/psychological suicidal risk factors in the subject; and predicting suicidality in the subject by the combination of the difference between the expression level of the biomarker in the subject and the reference expression level of the blood biomarker; the assessment of mood, anxiety, and combinations thereof; and the assessment of socio-demographic/psychological suicidal risk factor information.

BRIEF DESCRIPTION OF THE DRAWINGS

The disclosure will be better understood, and features, aspects and advantages other than those set forth above will become apparent when consideration is given to the following detailed description thereof. Such detailed description makes reference to the following drawings, wherein:

FIGS. 1A-1C depict the Discovery cohort of Example 1: longitudinal within subject analysis. Phchp ### is the study ID for each participant. V #denotes visit number (1, 2, 3, 4, 5, or 6). FIG. 1A depicts suicidal ideation (SI) scoring. FIG. 1B depicts subjects and visits. FIG. 1C depicts PhenoChipping: two-way unsupervised hierarchical clustering of all participant visits in the discovery cohort vs. 18 quantitative phenotypes measuring affective state and suicidality. SASS—Simplified Affective State Scale. A—Anxiety items (Anxiety, Uncertainty, Fear, Anger, Average). M—Mood items (Mood, Motivation, Movement, Thinking, Self-esteem, Interest, Appetite, Average). STAI-STATE is State Trait Anxiety Inventory, State Subscale. YMRS is Young Mania Rating Scale.

FIG. 2A depicts Discovery—number of probe sets carried forward from the AP and DE analyses, with an internal score of 1 and above. Underline-increased in expression in High SI, bold-decreased in expression in High SI. FIG. 2B depicts Prioritization—CFG integration of multiple lines of evidence to prioritize suicide-relevant genes from the discovery step. FIGS. 2C-2D depicts Validation—Top CFG genes validated in the cohort of suicide completers, with a total score of 4 and above. All the genes shown were significantly changed in ANOVA from No SI to High SI to Suicide Completers. *survived Bonferroni correction. SAT1 (x3) had three different probe sets with the same total score of 8.

FIGS. 3A-3D depict the Convergent Functional Information for Suicide (CFI-S) Scale as analyzed in Example 1. FIG. 3A depicts Validation of scale. CFI-S levels in the Discovery Cohort and Suicide Completers. FIGS. 3B & 3C depicts Validation of items. CFI-S was developed independently of any data from this Example by compiling known socio-demographic and clinical risk factors for suicide. It is composed of 22 items that assess the influence of mental health factors, as well as of life satisfaction, physical health, environmental stress, addictions, cultural factors known to influence suicidal behavior, and two demographic factors, age and gender. These 22 items are shown here validated in the discovery cohort and suicide completers in a manner similar to that for biomarkers. Additionally, a student's t-test was used to evaluate items that were increased in suicide completers when compared to living participants with high suicidal ideation. FIG. 3D depicts CFI-S predictions for suicidal ideation in the independent test cohort and predicting future hospitalizations due to suicidality.

FIGS. 4A & 4B depict the testing of Universal Predictor for Suicide (UP-Suicide). UP-Suicide is a combination of the best genomic data (top increased and decreased biomarkers from discovery and prioritization by CFG, and validation in suicide completers), and phenomic data (CFI-S and SASS). The graph in FIG. 4A depicts Area Under the Curve (AUC) for the UP-Suicide predicting suicidal ideation and hospitalizations within the first year in all participants, as well as separately in bipolar (BP), major depressive disorder (MDD), schizophrenia (SZ), and schizoaffective (SZA) participants. Two asterisks indicate the comparison survived Bonferroni correction for multiple comparisons. A single asterisk indicates nominal significance of $p<0.05$. Bold outline indicates that the UP-Suicide was synergistic to its components, i.e. performed better than the gene expression or phenomic markers individually. The table in FIG. 4B summarizes descriptive statistics for all participants together, as well as separately in BP, MDD, SZ, and SZA. Bold indicates the measure survived Bonferroni correction for 200 comparisons (20 genomic and phenomic markers/combinations× 2 testing cohorts for SI and future hospitalizations in the first year×5 diagnostic categories—all, BP, MDD, SZA, SZ). Pearson correlation data in the suicidal ideation test cohort is shown for HAMD-SI vs. UP-Suicide, as well as Pearson correlation data in the hospitalization test cohort for frequency of hospitalizations for suicidality in the first year, and for frequency of hospitalizations for suicidality in all future available follow-up intervals (that varies among subjects, from 1 year to 8.5 years).

FIGS. 5A-5C depict prediction of Suicidal Ideation by UP-Suicide. The graph in FIG. 5A (top left) depicts Receiver operating curve identifying participants with suicidal ideation against participants with No SI or intermediate SI. The graph in FIG. 5A (top right) depicts suicidal ideation prediction. The Y axis contains the average UP-suicide scores with standard error for no SI, intermediate SI, and high SI. The graph in FIG. 5A (bottom right) is a Scatter plot depicting HAMD-SI score on the Y-axis and UP-Suicide score on the X axis with linear trendline. The table in FIG. 5B summarizes the descriptive statistics. ANOVA was performed between groups with no SI, intermediate SI, and high SI. FIG. 5C depicts the number of subjects correctly identified in the test cohort by categories based on thresholds in the discovery cohort. Category 1 means within 1 standard deviation above the average of High SI subjects in the discovery cohort, Category 2 means between 1 and 2 standard deviations above, and so on. Category −1 means within 1 standard deviation below the average of the No SI subjects in the discovery cohort, Category −2 means between 1 and 2 standard deviations below, and so on.

FIGS. 6A-6C depicts the Simplified Affective State Scale (SASS) questionnaire for measuring mood and anxiety.

Figure 7A:
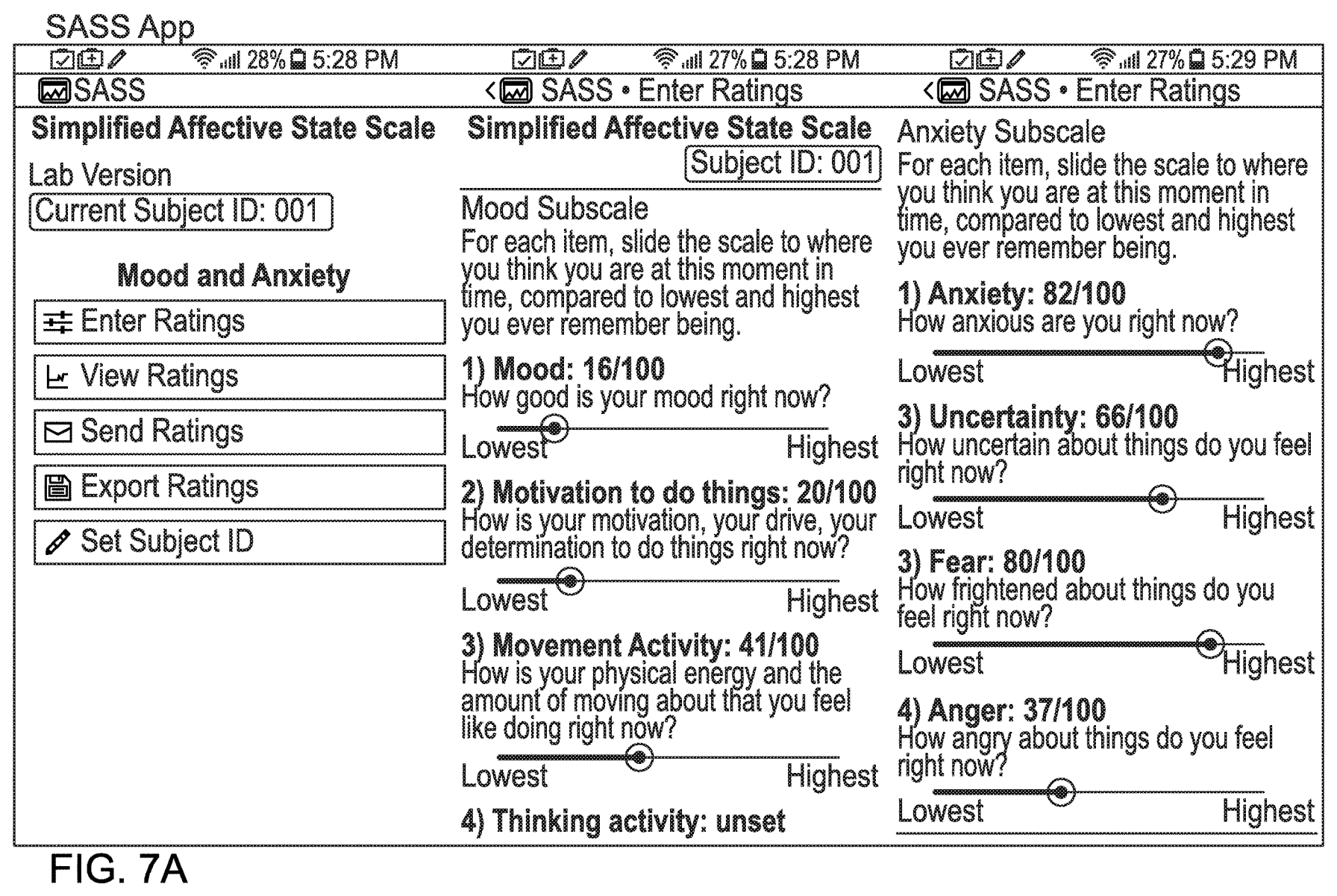
Figure 7B:
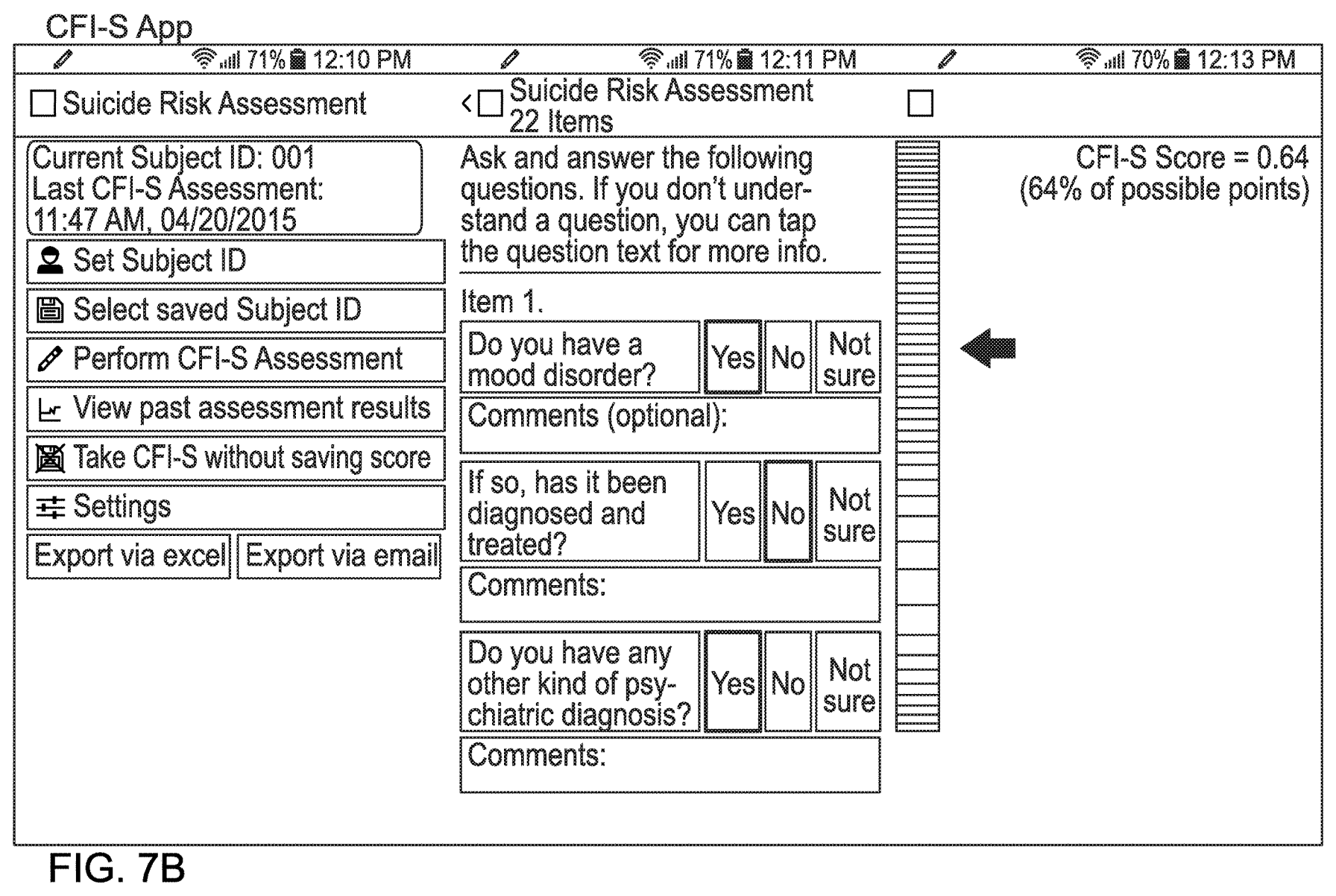

FIGS. 7A & 7B depict a screen image of the SASS mobile app (FIG. 7A) and CFI-S mobile app (FIG. 7B).

FIGS. 8A-8D summarize biological pathways and diseases as analyzed in Example 1.

FIG. 9 is a table summarizing the top biomarkers for all diagnoses, the top biomarkers for bipolar disorder, the top biomarkers for depression, the top biomarkers for schizoaffective disorder, and the top biomarkers for schizophrenia as analyzed in Example 1.

FIG. 10A depicts suicidal ideation (SI) scoring. FIG. 10B depicts participants and visits. FIG. 10C depicts PhenoChipping: two-way unsupervised hierarchical clustering of all participant visits in the discovery cohort vs. 18 quantitative phenotypes measuring affective state and suicidality. SASS—Simplified Affective State Scale. A—Anxiety items (Anxiety, Uncertainty, Fear, Anger, Average). M—Mood items—Mood, Motivation, Movement, Thinking, Self-esteem, Interest, Appetite, Average). STAI-STATE is State Trait Anxiety Inventory, State Subscale. YMRS is Young Mania Rating Scale.

FIG. 11A depicts Discovery—number of probesets carried forward from the AP and DE analyses, with an internal score of 1 and above. Underline-increased in expression in High SI, bold-decreased in expression in High SI. FIG. 11B depicts the Prioritization—CFG integration of multiple lines of evidence to prioritize suicide—relevant genes from the discovery step. FIG. 11C depicts Validation—Top CFG genes, with a total score of 4 and above, validated in the cohort of suicide completers. All the genes shown were significantly changed and survived Bonferroni correction in ANOVA from No SI to High SI to Suicide Completers. Some genes with (x n) after the symbol had multiple different probesets with the same total score.

FIGS. 12A-12D depict Convergent Functional Information for Suicide (CFI-S) Scale as analyzed in Example 2. CFI-S was developed independently of any data from this Example, by compiling known socio-demographic and clinical risk factors for suicide. It is composed of 22 items that assess the influence of mental health factors, as well as of life satisfaction, physical health, environmental stress, addictions, cultural factors known to influence suicidal behavior, and two demographic factors, age and gender. FIG. 12A depicts testing of scale in females. Prediction of high suicidal ideation in females in a larger cohort that combines the discovery and test cohorts used for biomarker work. The table depicts individual items and their ability to differentiate between No SI and High SI. FIG. 12B depicts testing of the scale in males, in a larger cohort that combines the discovery and test cohorts used for the biomarker work in Example 1. The table depicts individual items and their ability to differentiate between No SI and High SI.

FIG. 13A (Top left) depicts receiver operating curve identifying participants with suicidal ideation against participants with No SI or intermediate SI; (Top right): Y axis contains the average UP-Suicide scores with standard error of mean for no SI, intermediate SI, and high SI; (Bottom right): Scatter plot depicting HAMD-SI score on the Y-axis and UP-Suicide score on the X axis with linear trend line; and (Bottom Table) summarizes descriptive statistics. FIG. 13B (Top left) depicts receiver operating curve identifying participants with future hospitalizations due to suicidality against participants without future hospitalizations due to suicidality; (Top right): Y axis contains the average UP-Suicide scores with standard error of mean for no future hospitalizations due to suicidality and participants with future hospitalizations due to suicidality; (Bottom right): Scatter plot depicting frequency of future hospitalizations due to suicidality on the Y-axis and UP-Suicide score on the X axis with linear trend line; and (Bottom Table) summarizes descriptive statistics.

FIG. 14 is a table depicting the cohorts used in Example 2.

FIG. 15 is a table depicting biological pathways and diseases as analyzed in Example 2.

FIGS. 16A-16C is a table depicting UP-suicide predictions as analyzed in Example 2. UP-Suicide is composed of 50 validated biomarkers (18 increased in expression, 32 decreased in expression), along with clinical measures app scores (CFI-S, SASS). SASS is composed of Mood scale and Anxiety scale.

FIGS. 17A-17B depicts convergent functional information for suicide (CFI-S) App testing across genders. Prediction of high suicidal ideation in men and women in a larger cohort that combines the cohorts used in Examples 1 and 2 by gender. CFI-S was developed independently of any data from this disclosure, by compiling known socio-demographic and clinical risk factors for suicide. It is composed of 22 items that assess the influence of mental health factors, as well as of life satisfaction, physical health, environmental stress, addictions, cultural factors known to influence suicidal behavior, and two demographic factors, age and gender. The table depicts individual items and their ability to differentiate between No Suicidal Ideation and High Suicidal Ideation. These items provide clinical predictors and targets for psycho-therapeutic intervention.

FIGS. 18A-18B depicts convergent functional information for future hospitalization for suicide (CFI-S) App testing across genders. Particularly, prediction of future hospitalizations for suicidality in men and women in a larger cohort that combines the cohorts used in our studies by gender.

Figure 1B:
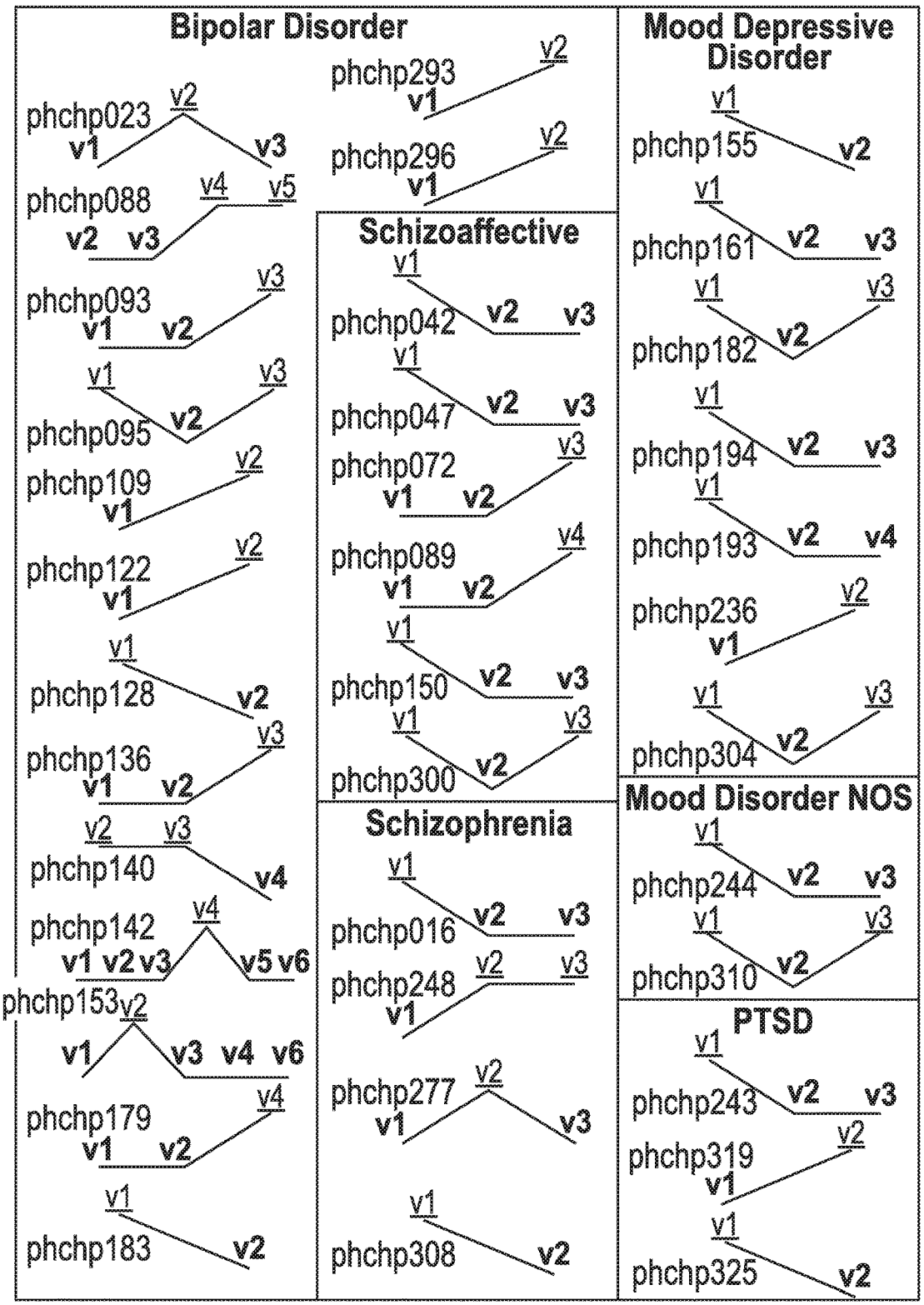

While the disclosure is susceptible to various modifications and alternative forms, specific embodiments thereof have been shown by way of example in the drawings and are herein described below in detail. It should be understood, however, that the description of specific embodiments is not intended to limit the disclosure to cover all modifications, equivalents and alternatives falling within the spirit and scope of the disclosure as defined by the appended claims.

DETAILED DESCRIPTION

Unless defined otherwise, all technical and scientific terms used herein have the same meaning as commonly understood by one of ordinary skill in the art to which the disclosure belongs. Although any methods and materials similar to or equivalent to those described herein can be used in the practice or testing of the present disclosure, the preferred methods and materials are described below.

New data for discovery, prioritization, validation and testing of next generation broader-spectrum blood biomarkers for suicidal ideation and behavior, across psychiatric diagnoses are disclosed. Also disclosed are two clinical information questionnaires in the form of apps, one for affective state (Simplified Affective Scale, SASS) and one for suicide risk factors (Convergent Functional Information for Suicide, CFI-S), that are useful in predicting suicidality. Both of these instruments do not directly ask about suicidal ideation. Also disclosed is a comprehensive universal predictor for suicide (UP-Suicide), composed of the combination of top biomarkers (from discovery, prioritization and validation), along with CFI-S, and SASS, which predicts in independent test cohorts suicidal ideation and future psychiatric hospitalizations for suicidality.

As disclosed herein, "patient psychiatric information" may include mood information, anxiety information, and other psychiatric symptom information and combinations thereof.

As used herein, "predicting suicidality in a subject" is used herein to indicate in advance that a subject will attempt suicide and/or complete suicide.

As known by those skilled in the art, "suicidal ideation" refers to thoughts, feelings, intent, external actions and behaviors about completing suicide. Suicidal ideation can vary from fleeting thoughts to unsuccessful attempts. In some embodiments, the reference expression level of a biomarker can be obtained for a subject who has no suicidal ideation at the time the sample is obtained from the subject, but who later exhibits suicide ideation. As used herein, "suicidality" includes both suicide ideation and suicidal acts.

As used herein, "a reference expression level of a biomarker" refers to the expression level of a biomarker established for a subject with no suicidal ideation, expression level of a biomarker in a normal/healthy subject with no suicidal ideation as determined by one skilled in the art using established methods as described herein, and/or a known expression level of a biomarker obtained from literature. The reference expression level of the biomarker can further refer to the expression level of the biomarker established for a high suicide risk subject, including a population of high suicide risk subjects. The reference expression level of the biomarker can also refer to the expression level of the biomarker established for a low suicide risk subject, including a population of low suicide risk subjects. The reference expression level of the biomarker can also refer to the expression level of the biomarker established for any combination of subjects such as a subject with no suicidal ideation, expression level of the biomarker in a normal/healthy subject with no suicidal ideation, expression level of the biomarker for a subject who has no suicidal ideation at the time the sample is obtained from the subject, but who later exhibits suicide ideation, expression level of the biomarker as established for a high suicide risk subject, including a population of high suicide risk subjects, and expression level of the biomarker can also refer to the expression level of the biomarker established for a low suicide risk subject, including a population of low suicide risk subjects. The reference expression level of the biomarker can also refer to the expression level of the biomarker obtained from the subject to which the method is applied. As such, the change within a subject from visit to visit can indicate an increased or decreased risk for suicide. For example, a plurality of expression levels of a biomarker can be obtained from a plurality of samples obtained from the same subject and used to identify differences between the plurality of expression levels in each sample. Thus, in some embodiments, two or more samples obtained from the same subject can provide an expression level(s) of a blood biomarker and a reference expression level(s) of the blood biomarker.

As used herein, "expression level of a biomarker" refers to the process by which a gene product is synthesized from a gene encoding the biomarker as known by those skilled in the art. The gene product can be, for example, RNA (ribonucleic acid) and protein. Expression level can be quantitatively measured by methods known by those skilled in the art such as, for example, northern blotting, amplification, polymerase chain reaction, microarray analysis, tag-based technologies (e.g., serial analysis of gene expression and next generation sequencing such as whole transcriptome shotgun sequencing or RNA-Seq), Western blotting, enzyme linked immunosorbent assay (ELISA), and combinations thereof.

As used herein, a "difference" in the expression level of the biomarker refers to an increase or a decrease in the expression of a blood biomarker when analyzed against a reference expression level of the biomarker. In some embodiments, the "difference" refers to an increase or a decrease by about 1.2-fold or greater in the expression level of the biomarker as identified between a sample obtained from the subject and the reference expression level of the biomarker. In one embodiment, the difference in expression level is an increase or decrease by about 1.2 fold. As used herein "a risk for suicide" can refer to an increased (greater) risk that a subject will attempt to commit suicide and/or complete suicide For example, depending on the biomarker(s) selected, the difference in the expression level of the biomarker(s) can indicate an increased (greater) risk that a subject will attempt to commit suicide and/or complete suicide. Conversely, depending on the biomarker(s) selected, the difference in the expression level of the biomarker(s) can indicate a decreased (lower) risk that a subject will attempt to commit suicide and/or complete suicide.

In accordance with the present disclosure, biomarkers useful for objectively predicting, mitigating, and/or preventing suicidality in subjects have been discovered. In one aspect, the present disclosure is directed to a method for predicting suicidality in a subject. The method includes obtaining a reference expression level of a blood biomarker; and determining an expression level of the blood biomarker in a sample obtained from the subject. A change in the expression level of the blood biomarker in the sample obtained from the subject as compared to the reference expression level indicates suicidality. In some embodiments, the methods further include obtaining clinical risk factor information and clinical scale data such as for anxiety, mood and/or psychosis from the subject in addition to obtaining blood biomarker expression level in a sample obtained from the subject.

In one embodiment, the expression level of the blood biomarker in the sample obtained from the subject is increased as compared to the reference expression level of the biomarker. It has been found that an increase in the expression level of particular blood biomarkers in the sample obtained from the subject as compared to the reference expression level of the biomarker indicates a risk for suicide. Suitable biomarkers that indicate a risk for suicide when the expression level increases can be, for example, one or more biomarkers as listed in Table 1 and combinations thereof.

TABLE 1

Top Candidate Biomarker Genes - increase in expression

| Gene Name | Gene Symbol |
|---|---|
| interleukin 6 (interferon, beta 2) | IL6 |
| spermidine/spermine N1-acetyltransferase 1 | SAT1 |
| solute carrier family 4 (sodium bicarbonate cotransporter), member 4 | SLC4A4 |
| monoamine oxidase B | MAOB |
| Glutamate Receptor, Ionotropic, Kainate 2 | GRIK2 |
| Rho GTPase activating protein 26 | ARHGAP26 |
| B-cell CLL/lymphoma 2 | BCL2 |
| cadherin 4, type 1, R-cadherin (retinal) | CDH4 |
| chemokine (C—X—C motif) ligand 11 | CXCL11 |
| EMI domain containing 1 | EMID1 |
| family with sequence similarity 49, member B | FAM49B |
| GRB2-Associated Binding Protein 1 | GAB1 |
| GRINL1A complex locus 1 | GCOM1 |
| hippocalcin-like 1 | HPCAL1 |
| mitogen-activated protein kinase 9 | MAPK9 |
| nuclear paraspeckle assembly transcript 1 (non-protein coding) | NEAT1 |
| protein tyrosine kinase 2 | PTK2 |
| RAS-like, family 11, member B | RASL11B |
| small nucleolar RNA, H/ACA box 68 | SNORA68 |
| superoxide dismutase 2, mitochondrial | SOD2 |
| transcription factor 7-like 2 (T-cell specific, HMG-box) | TCF7L2 |
| v-raf murine sarcoma viral oncogene homolog B | BRAF |
| chromosome 1 open reading frame 61 | C1orf61 |
| Calreticulin | CALR |
| calcium/calmodulin-dependent protein kinase II beta | CAMK2B |
| caveolin 1, caveolae protein, 22 kDa | CAV1 |
| chromodomain helicase DNA binding protein 2 | CHD2 |
| clathrin, light chain A | CLTA |
| cAMP responsive element modulator | CREM |
| Cortactin | CTTN |
| dishevelled associated activator of morphogenesis 2 | DAAM2 |
| Dab, mitogen-responsive phosphoprotein, homolog 2 (Drosophila) | DAB2 |
| GABA(A) receptor-associated protein like 1 | GABARAPL1 GABA(A) |
| glutamate-ammonia ligase | GLUL |
| helicase with zinc finger | HELZ |
| immunoglobulin heavy constant gamma 1 (G1m marker) | IGHG1 |
| interleukin 1, beta | IL1B |
| jun proto-oncogene | JUN |
| jun B proto-oncogene | JUNB |
| lipoma HMGIC fusion partner | LHFP |
| myristoylated alanine-rich protein kinase C substrate | MARCKS |
| metallothionein 1E | MT1E |
| metallothionein 1H | MT1H |
| metallothionein 2A | MT2A |
| N-myc downstream regulated 1 | NDRG1 |
| nucleobindin 2 | NUCB2 |

TABLE 1-continued

Top Candidate Biomarker Genes - increase in expression

| Gene Name | Gene Symbol |
|---|---|
| PHD finger protein 20-like 1 | PHF20L1 |
| phosphatase and tensin homolog | PTEN |
| reversion-inducing-cysteine-rich protein with kazal motifs | RECK |
| shisa family member 2 | SHISA2 |
| transmembrane 4 L six family member 1 | TM4SF1 |
| trophoblast glycoprotein | TPBG |
| tumor protein D52-like 1 | TPD52L1 |
| TSC22 domain family, member 3 | TSC22D3 |
| vacuole membrane protein 1 | VMP1 |
| ZFP36 ring finger protein | ZFP36 |
| zinc fingers and homeoboxes 2 | ZHX2 |
| UDP-Gal:betaGlcNAc beta 1,4-galactosyltransferase, polypeptide 1 | B4GALT1 |
| BTB (POZ) domain containing 3 | BTBD3 |
| cell adhesion molecule 1 | CADM1 |
| chitobiase, di-N-acetyl- | CTBS |
| DEP domain containing 5 | DEPDC5 |
| dystrobrevin, alpha | DTNA |
| egf-like module containing, mucin-like, hormone receptor-like 2 | EMR2 |
| endogenous retrovirus group 3, member 2 | ERV3-2 |
| family with sequence similarity 183, member C, pseudogene | FAM183CP |
| histone cluster 1, H2bo | HIST1H2BO |
| potassium channel tetramerization domain containing 21 | KCTD21 |
| Keratocan | KERA |
| laminin, beta 1 | LAMB1 |
| uncharacterized LOC100289061 | LOC100129917 |
| uncharacterized LOC285500 | LOC285500 |
| RAB36, member RAS oncogene family | RAB36 |
| uncharacterized LOC283352 | RP11-66N7.2 |
| transcription factor Dp-1 | TFDP1 |
| TMLHE antisense RNA 1 | TMLHE-AS1 |
| superoxide dismutase 2, mitochondrial | SOD2 |
| period circadian clock 1 | PER1 |
| Ras association (RalGDS) | RAPH1 |
| spondin 1, extracellular matrix protein | SPON1 |
| forkhead box P1 | FOXP1 |
| hepatitis A virus cellular receptor 2 | HAVCR2 |
| Rho GTPase activating protein 15 | ARHGAP15 |
| gap junction protein, alpha 1, 43 kDa | GJA1 |
| hes family bHLH transcription factor 1 | HES1 |
| HtrA serine peptidase 1 | HTRA1 |
| TIMP metallopeptidase inhibitor 1 | TIMP1 |
| erythrocyte membrane protein band 4.1 like 5 | EPB41L5 |
| interleukin 1 receptor, type I | IL1R1 |
| intelectin 1 (galactofuranose binding) | ITLN1 |
| killer cell immunoglobulin-like receptor, two domains, long cytoplasmic tail, 4 | KIR2DL4 |
| nudix (nucleoside diphosphate linked moiety X)-type motif 10 | NUDT10 |
| pyridoxal-dependent decarboxylase domain containing 1 | PDXDC1 |
| family with sequence similarity 214, member A | FAM214A |
| heat shock 60 kDa protein 1 (chaperonin) | HSPD1 |
| zinc finger, MYND-type containing 8 | ZMYND8 |
| adenylate kinase 2 | AK2 |
| AF4/FMR2 family, member 3 | AFF3 |
| mitochondrial ribosomal protein S5 | MRPS5 |
| v-akt murine thymoma viral oncogene homolog 3 | AKT3 |
| aspartate beta-hydroxylase | ASPH |
| ataxin 1 | ATXN1 |
| Brain and reproductive organ-expressed (TNFRSF1A modulator) | BRE |
| ClpB caseinolytic peptidase B homolog (*E. coli*) | CLPB |
| deleted in primary ciliary dyskinesia homolog (mouse) | DPCD |
| ECSIT signalling integrator | ECSIT |
| ectonucleoside triphosphate diphosphohydrolase 1 | ENTPD1 |
| EPH receptor B4 | EPHB4 |
| Fanconi anemia, complementation group I | DANCI |
| general transcription factor IIIC, polypeptide 3, 102 kDa | GTF3C3 |
| inter-alpha-trypsin inhibitor heavy chain family, member 5 | ITIH5 |
| kelch-like family member 28 | KLHL28 |
| major histocompatibility complex, class I-related | MR1 |
| protein inhibitor of activated STAT, 1 | PIAS1 |
| periphilin 1 | PPHLN1 |
| retinol dehydrogenase 13 (all-trans/9-cis) | RDH13 |
| strawberry notch homolog 1 (*Drosophila*) | SBN01 |
| sorting nexin family member 27 | SNX27 |
| single-stranded DNA binding protein 2 | SSBP2 |

TABLE 1-continued

Top Candidate Biomarker Genes - increase in expression

| Gene Name | Gene Symbol |
| --- | --- |
| striatin, calmodulin binding protein | STRN |
| tetratricopeptide repeat domain 7A | TTC7A |
| ubiquitin interaction motif containing 1 | UIMC1 |
| Z-DNA binding protein 1 | ZBP1 |
| zinc finger protein 596 | ZNF596 |
| adaptor-related protein complex 3, sigma 2 subunit | AP3S2 |

In one particularly suitable embodiment, the subject is a male and the blood biomarker that increases in expression level as compared to the reference expression level is selected from solute carrier family 4 (sodium bicarbonate cotransporter), member 4 (SLC4A4), cell adhesion molecule 1 CADM1, dystrobrevin, alpha (DTNA), spermidine/spermine N1-acetyltransferase 1 (SAT1), interleukin 6 (interferon, beta 2) (IL6) and combinations thereof. In another embodiment, the subject is a female and the blood biomarker that increases in expression level as compared to the reference expression level is selected from erythrocyte membrane protein band 4.1 like 5 (EPB41L5), HtrA serine peptidase 1 (HTRA1), deleted in primary ciliary dyskinesia homolog (DPCD), general transcription factor IIIC, polypeptide 3, 102 kDa (GTF3C3), period circadian clock 1 (PER1), pyridoxal-dependent decarboxylase domain containing 1 (PDXDC1), kelch-like family member 28 (KLHL28), ubiquitin interaction motif containing 1 (UIMC1), sorting nexin family member 27 (SNX27) and combinations thereof.

In another embodiment, the expression level of the blood biomarker in the sample obtained from the subject is decreased as compared to the reference expression level of the biomarker. Suitable biomarkers that indicate a risk for suicide when the expression level decreases as compared to the reference expression level have been found to include, for example, one or more biomarkers as listed in Table 2 and combinations thereof.

TABLE 2

Top Candidate Biomarker Genes - decrease in expression

| Gene Name | Gene Symbol |
| --- | --- |
| spindle and kinetochore associated complex subunit 2 | SKA2 |
| coiled-coil domain containing 136 | CCDC136 |
| CD44 molecule (Indian blood group) | CD44 |
| fatty acid desaturase 1 | FADS1 |
| FK506 binding protein 5 | FKBP5 |
| forkhead box N3 | FOXN3 |
| hydroxyacyl-CoA dehydrogenase/3-ketoacyl-CoA thiolase/enoyl-CoA hydratase (trifunctional protein), alpha subunit | HADHA |
| adenosylhomocysteinase-like 1 | AHCYL1 |
| AKT1 substrate 1 (proline-rich) | AKT1S1 |
| aldehyde dehydrogenase 3 family, member A2 | ALDH3A2 |
| B-cell CLL/lymphoma 2 | BCL2 |
|  | C20orf27 |
| calpain, small subunit 1 | CAPNS1 |
| CDC42 effector protein (Rho GTPase binding) 4 | CDC42EP4 |
| EH domain binding protein 1 | EHBP1 |
| eukaryotic translation initiation factor 5A | EIF5A |
| fumarate hydratase | FH |
| glycoprotein M6B | GPM6B |

TABLE 2-continued

Top Candidate Biomarker Genes - decrease in expression

| Gene Name | Gene Symbol |
| --- | --- |
| homeobox and leucine zipper encoding | HOMEZ |
| inhibitor of kappa light polypeptide gene enhancer in B-cells, kinase beta | IKBKB |
| integrin, beta 4 | ITGB4 |
| low density lipoprotein receptor adaptor protein 1 | LDLRAP1 |
| uncharacterized LOC728543 | LOC728543 |
| mitogen-activated protein kinase kinase 5 | MAP2K5 |
| neuromedin B | NMB |
| platelet-activating factor acetylhydrolase 1b, catalytic subunit 2 (30 kDa) | PAFAH1B2 |
| pterin-4 alpha-carbinolamine dehydratase/dimerization cofactor of hepatocyte nuclear factor 1 alpha (TCF1) 2 | PCBD2 |
| phosphatidylinositol-4-phosphate 3-kinase, catalytic subunit type 2 alpha | PIK3C2A |
| plakophilin 4 | PKP4 |
| solute carrier family 5 (sodium/myo-inositol cotransporter), member 3 | SLC5A3 |
| spectrin repeat containing, nuclear envelope 2 | SYNE2 |
| trans-golgi network protein 2 | TGOLN2 |
| trafficking protein, kinesin binding 2 | TRAK2 |
| adrenergic, beta, receptor kinase 1 | ADRBK1 |
| adenosylhomocysteinase-like 2 | AHCYL2 |
| aminoacyl tRNA synthetase complex-interacting multifunctional protein 1 | AIMP1 |
| ATPase, H+ transporting, lysosomal 9 kDa, V0 subunit e1 | ATP6V0E1 |
| BRCA1/BRCA2-containing complex, subunit 3 | BRCC3 |
| 2',3'-cyclic nucleotide 3' phosphodiesterase | CNP |
| collagen, type IX, alpha 2 | COL9A2 |
| cleavage and polyadenylation specific factor 2, 100 kDa | CPSF2 |
| cullin 4B | CUL4B |
| delta-like 1 (*Drosophila*) | DLL1 |
| dynein, axonemal, heavy chain 2 | DNAH2 |
| dipeptidyl-peptidase 4 | DPP4 |
| G2/M-phase specific E3 ubiquitin protein ligase | G2E3 |
| guanylate kinase 1 | GUK1 |
| Janus kinase 3 | JAK3 |
| lysosomal protein transmembrane 4 beta | LAPTM4B |
| lysophosphatidic acid receptor 1 | LPAR1 |
| membrane associated guanylate kinase, WW and PDZ domain containing 3 | MAGI3 |
| myelin basic protein | MBP |
| microspherule protein 1 | MCRS1 |
| myocyte enhancer factor 2C | MEF2C |
| opioid growth factor receptor | OGFR |
| protocadherin 9 | PCDH9 |
| pleckstrin homology domain containing, family B (evectins) member 1 | PLEKHB1 |
| polymerase (RNA) II (DNA directed) polypeptide D | POLR2D |
| protein kinase, cAMP-dependent, catalytic, alpha | PRKACA |
| protein kinase C, beta | PRKCB |

TABLE 2-continued

Top Candidate Biomarker Genes - decrease in expression

| Gene Name | Gene Symbol |
|---|---|
| proteasome (prosome, macropain) subunit, beta type, 4 | PSMB4 |
| RAB35, member RAS oncogene family | RAB35 |
| RNA binding motif protein, X-linked | RBMX |
| ribonuclease L (2',5'-oligoisoadenylate synthetase-dependent) | RNASEL |
| selenium binding protein 1 | SELENBP1 |
| solute carrier family 35, member E1 | SLC35E1 |
| synaptosomal-associated protein, 23 kDa | SNAP23 |
| transmembrane protein 254 | TMEM254 |
| transmembrane protein 259 | TMEM259 |
| tensin 1 | TNS1 |
| tripartite motif containing 23 | TRIM23 |
| tetraspanin 33 | TSPAN33 |
| pre-B lymphocyte 3 | VPREB3 |
| zinc finger, FYVE domain containing 21 | ZFYVE21 |
| zinc finger protein 519 | ZNF519 |
| cation channel, sperm associated 3 | CATSPER3 |
| chemokine (C-C motif) ligand 28 | CCL28 |
| CAP-GLY domain containing linker protein family, member 4 | CLIP4 |
| chromosome Y open reading frame 17 | CYorf17 |
| DDB1 and CUL4 associated factor 15 | DCAF15 |
| EPH receptor A10 | EPHA10 |
| v-ets avian erythroblastosis virus E26 oncogene homolog | ERG |
| heparan sulfate (glucosamine) 3-O-sulfotransferase 3B1 | HS3ST3B1 |
| IQ motif containing H | IQCH |
| kinesin family member 2C | KIF2C |
| kelch domain containing 3 | KLHDC3 |
| uncharacterized LOC100129917 | LOC100129917 |
| uncharacterized LOC100996345 | LOC100996345 |
| mediator complex subunit 21 | MED21 |
| PDX1 C-terminal inhibiting factor 1 | PCIF1 |
| plectin | PLEC |
| RAD23 homolog A (S. cerevisiae) | RAD23A |
| Rh-associated glycoprotein | RHAG |
| roundabout, axon guidance receptor, homolog 4 (Drosophila) | ROBO4 |
| ribosomal protein L6 pseudogene 17 | RPL6P17 |
| SET domain containing (lysine methyltransferase) 8 | SETD8 |
| SH3-domain GRB2-like endophilin B2 | SH3GLB2 |
| ST6 (alpha-N-acetyl-neuraminyl-2,3-beta-galactosyl-1,3)-N-acetylgalactosaminide alpha-2,6-sialyltransferase 4 | ST6GALNAC4 |
| testis expressed 10 | TEX10 |
| testis expressed 261 | TEX261 |
| thymosin beta 15B | TMSB15B |
| tubulin, gamma complex associated protein 3 | TUBGCP3 |
| thioredoxin reductase 2 | TXNRD2 |
| ubiquitin specific peptidase 12 | USP12 |
| vascular endothelial growth factor B | VEGFB |
| zinc finger and BTB domain containing 7A | ZBTB7A |
| glycogen synthase kinase 3 beta | GSK3B |
| adaptor-related protein complex 1, sigma 2 subunit | AP1S2 |
| catalase | CAT |
| chromosome 18 open reading frame 54 | C19orf54 |
| long intergenic non-protein coding RNA 342 | LINC00342 |
| MOB kinase activator 3B | MOB3B |
| phosphatidylinositol-4-phosphate 5-kinase, type I, beta | PIP5K1B |
| prolylcarboxypeptidase (angiotensinase C) | PRCP |
| CD200 receptor 1 | CD200R1 |
| CD84 molecule | CD84 |
| centrosomal protein 44 kDa | CEP44 |
| carnitine O-octanoyltransferase | CROT |
| DDB1 and CUL4 associated factor 5 | DCAF5 |
| DTW domain containing 2 | DTWD2 |
| endoplasmic reticulum protein 27 | ERP27 |
| family with sequence similarity 173, member B | FAM173B |
| glucosidase, alpha; neutral C | GANC |
| general transcription factor IIIC, polypeptide 2, beta 110 kDa | GTF3C2 |
| INO80 complex subunit D | INO80D |
| inositol polyphosphate-4-phosphatase, type I, 107 kDa | INPP4A |
| Jrk homolog (mouse) | JRK |
| potassium channel tetramerization domain containing 5 | KCTD5 |
| methyltransferase like 15 | METTL15 |
| phosphatidylinositol 3-kinase, catalytic subunit type 3 | PIK3C3 |
| RNA binding motif protein 48 | RBM48 |
| SWI/SNF Related, Matrix Associated, Actin Dependent Regulator Of Chromatin, Subfamily A, Member 2 | SMARCA2 |
| ubiquitin carboxyl-terminal hydrolase L5 | UCHL5 |
| vacuolar protein sorting 53 homolog (S. cerevisiae) | VPS53 |
| zinc finger protein 302 | ZNF302 |
| capping protein (actin filament) muscle Z-line, alpha 2 | CAPZA2 |
| leucine rich repeat containing 8 family, member B | LRRC8B |
| protein phosphatase, Mg2+ | PPM1B |
| ARP3 actin-related protein 3 homolog (yeast) | ACTR3 |
| SH2 domain containing 1A | SH2D1A |
| ALG13, UDP-N-acetylglucosaminyltransferase subunit | ALG13 |
| Rho GTPase activating protein 35 | ARHGAP35 |
| AT rich interactive domain 4B (RBP1-like) | ARID4B |
| charged multivesicular body protein 2B | CHMP2B |
| casein kinase 1, alpha 1 | CSNK1A1 |
| ethanolamine kinase 1 | ETNK1 |
| F-box and leucine-rich repeat protein 3 | FBXL3 |
| HECT and RLD domain containing E3 ubiquitin protein ligase 4 | HERC4 |
| jumonji domain containing 1C | JMJD1C |
| La ribonucleoprotein domain family, member 4 | LARP4 |
| muscleblind-like splicing regulator 1 | MBNL1 |
| mex-3 RNA binding family member C | MEX3C |
| nudix (nucleoside diphosphate linked moiety X)-type motif 6 | NUDT6 |
| polyhomeotic homolog 3 (Drosophila) | PHC3 |
| peroxiredoxin 3 | PRDX3 |
| Pvt1 oncogene (non-protein coding) | PVT1 |
| RAB22A, member RAS oncogene family | RAB22A |
| solute carrier family 35 (adenosine 3'-phospho 5'-phosphosulfate transporter), member B3 | SLC35B3 |
| small nuclear ribonucleoprotein 27kDa (U4 | SNRNP27 |
| USP6 N-terminal like | USP6NL |
| WW domain containing adaptor with coiled-coil | WAC |
| wings apart-like homolog (Drosophila) | WAPAL |
| zinc finger, AN1-type domain 5 | ZFAND5 |
| zinc finger protein 117 | ZNF117 |
| zinc finger protein 141 | ZNF141 |
| zinc finger protein 548 | ZNF548 |
| signal sequence receptor, alpha | SSR1 |

In one particularly suitable embodiment, the subject is a male and the blood biomarker that decreases in expression level as compared to the reference expression level is spindle and kinetochore associated complex subunit 2 (SKA2), CAP-GLY domain containing linker protein family, member 4 (CLIP4), kinesin family member 2C (KIF2C), kelch domain containing 3 (KLHDC3) and combinations thereof. In another embodiment, the subject is a female and the blood biomarker that decreases in expression level as compared to the reference expression level is selected from phosphatidylinositol 3-kinase, catalytic subunit type 3 (PIK3C3), aldehyde dehydrogenase 3 family, member A2 (ALDH3A2), ARP3 actin-related protein 3 homolog (yeast) (ACTR3), B-cell CLL (BCL2), MOB kinase activator 3B (MOB3B), casein kinase 1, alpha 1 (CSNK1A1), La ribonucleoprotein domain family, member 4 (LARP4), zinc finger protein 548 (ZNF548) and combinations thereof.

Table 3 further discloses the top biomarkers across gender having expression levels that increase or decrease (as indicated) as compared to the reference expression levels to predict suicidality.

TABLE 3

Top Universal Biomarkers for Suicide Across Genders

| Gene Symbol Gene Name | Affymetrix Probesets | Discovery in Blood (Direction of Change)/ Score | Validation in Blood ANOVA p-value/Score | Significant Prediction of Suicidal Ideation Across All and Best In a Diagnostic Group ROC AUC/ p-value |
|---|---|---|---|---|
| BCL2 B-cell CLL/lymphoma 2 | 203685_at | (D)/1 | 5.98E−11/4 | All 0.609/0.005 Male SZ/SZA 0.68/0.011 |
| CD164 CD164 molecule, sialomucin | 208654_s_at | (D)/2 | 3.01E−08/4 | All 0.589/0.017 Male BP 0.68/0.020 |
| CD47 CD47 molecule | 211075_s_at | (D)/2 | 1.62E−17/4 | All 0.598/0.010 Male SZ/SZA 0.67/0.016 |
| DLG1 discs, large homolog 1 (*Drosophila*) | 202514_at | (D)/1 | 0.0000844 | All 0.58/0.036 Male SZ/SZA 0.65/0.030 |
| DLG1 discs, large homolog 1 (*Drosophila*) | 202516_s_at | (D)/1 | 0.0000000000016/4 | All 0.58/0.029 |
| DYRK2 dual-specificity tyrosine-(Y)-phosphorylation regulated kinase 2 | 202969_at | (D)/1 | 0.00000000000017/4 | All 0.58/0.034 Male SZ/SZA 0.68/0.010 |
| ITGB1BP1 integrin beta 1 binding protein 1 | 203336_s_at | (D)/1 | 0.000000025/4 | All 0.57/0.042 |
| APOE apolipoprotein E | 203382_s_at | (I)/1 | 3.44E−09/4 | All 0.59/0.021 Male BP 0.71/0.0091 |
| MRPS14 mitochondrial ribosomal protein S14 | 203800_s_at | (D)/1 | 0.00000000039/4 | Male SZ/SZA 0.69/0.0080 |
| MRPS14 mitochondrial ribosomal protein S14 | 203801_at | (D)/1 | 2.45E−17/4 | All 0.60/0.0069 Male SZ/SZA 0.68/0.011 |
| IL6 interleukin 6 | 205207_at | (I)/1 | 1.82E−15/4 | All 0.58/0.038 |
| AKAP13 A kinase (PRKA) anchor protein 13 | 209534_x_at | (I)/1 | 0.000021/4 | Male PTSD 0.78/0.0083 |
| SECISBP2L SECIS binding protein 2-like | 212450_at | (D)/1 | 0.000063/4 | All 0.59/0.021 Male BP 0.71/0.0076 |
| SOD2 superoxide dismutase 2, mitochondrial | 215078_at | (I)/2 | 2.27E−34/4 | |
| LHFP lipoma HMGIC fusion partner | 218656_s_at | (I)/1 | 0.00000000040/4 | All 0.57/0.05 Male MDD 0.69/0.034 |

TABLE 3-continued

Top Universal Biomarkers for Suicide Across Genders

| Gene | Probe | Type | p-value | Cohort / AUC/p |
|---|---|---|---|---|
| SKA2 spindle and kinetochore associated complex subunit 2 | 225686_at | (D)/1 | 4.55E−03/2 | All 0.62/0.003 Male SZ/SZA 0.75/0.00063 |
| GSK3B glycogen synthase kinase 3 beta | 226183_at | (D)/1 | 2.19E−36/4 | |
| ITPKB inositol-trisphosphate 3-kinase B | 232526_at | AP (I)/1 | 0.0000000045/4 | All 0.62/0.0019 Male BP 0.76/0.0013 |
| MTERF4 mitochondrial transcription termination factor 4 | 1557966_x_at | (D)/2 | 6.72E−06/4 | All 0.61/0.005 Male SZ/SZA 0.72/0.0019 |
| GDI2 GDP dissociation inhibitor 2 | 200008_s_at | (D)/2 | 1.52E−11/4 | All 0.59/0.013 Male BP 0.67/0.024 |
| PRKAR1A protein kinase, cAMP-dependent, regulatory, type I, alpha | 200605_s_at | (D)/2 | 2.47E−06/4 | Male BP 0.72/0.0059 |
| NR3C1 nuclear receptor subfamily 3, group C, member 1 (glucocorticoid receptor) | 201866_s_at | (D)/1 | 1.64E−03/2 | Male BP 0.67/0.029 |
| ADK adenosine kinase | 204119_s_at | DE (D)/4 | 0.000000020/4 | All 0.62/0.0026 Male SZ/SZA 0.66/0.019 |
| PGK1 phosphoglycerate kinase 1 | 217383_at | (D)/2 | 4.07E−07/4 | Male SZ/SZA 0.63/0.046 |
| ZFYVE21 zinc finger, FYVE domain containing 21 | 219929_s_at | (D)/2 | 5.96E−06/4 | All 0.58/0.026 |
| RBM3 RNA binding motif (RNP1, RRM) protein 3 | 222026_at | (D)/2 | 1.73E−05/4 | |
| FAM107B family with sequence similarity 107, member B | 223058_at | (D)/2 | 2.36E−02/2 | All 0.58/0.024 Male BP 0.71/0.0079 |
| ECHDC1 enoyl CoA hydratase domain containing 1 | 223087_at | (D)/2 | 3.35E−09/4 | All 0.60/0.009 Male SZ/SZA 0.66/0.019 |
| TBL1XR1 transducin (beta)-like 1 X-linked receptor 1 | 235890_at | AP (D)/2 | 0.000000023/4 | Male BP 0.66/0.034 |
| LONRF2 LON peptidase N-terminal domain and ring finger 2 | 235977_at | (I)/1 | 1.48E−03/2 | Male BP 0.73/0.0040 |
| QKI QKI, KH domain containing, RNA binding | 241938_at | (I)/2 | 1.88E−03/2 | Male PTSD 0.77/0.011 |
| YWHAH tyrosine 3-monooxygenase/tryptophan 5-monooxygenase activation protein, eta | 242325_at | (I)/2 | 6.65E−11/4 | All 0.571/0.047 Male BP 0.66/0.033 |

TABLE 3-continued

Top Universal Biomarkers for Suicide Across Genders

| | | | | |
|---|---|---|---|---|
| SLC4A4 solute carrier family 4 (sodium bicarbonate cotransporter), member 4 | 210739_x_at | (I)/1 | 7.74E−05/4 | All 0.64/0.00038 Male BP 0.77/0.00094 |
| GDI2 GDP dissociation inhibitor 2 | 200009_at | (D)/1 | 0.000015/4 | All 0.64/0.0006 Male SZ/SZA 0.72/0.0028 |
| UQCRC2 ubiquinol-cytochrome c reductase core protein II | 200883_at | (D)/1 | 0.012/2 | All 0.61/0.0035 Male SZ/SZA 0.67/0.013 |
| CTNNB1 catenin (cadherin-associated protein), beta 1, 88 kDa | 201533_at | (D)/1 | 0.0023/2 | All 0.59/0.018 Male BP 0.74/0.0037 |
| PSMB4 proteasome (prosome, macropain) subunit, beta type, 4 | 202243_s_at | (D)/1 | 6.55E−14/4 | All 0.6/0.011 Male SZ/SZA 0.68/0.010 |
| PRKACB protein kinase, cAMP-dependent, catalytic, beta | 202742_s_at | (D)/1 | 0.00042/2 | All 0.58/0.028 |
| LPAR1 lysophosphatidic acid receptor 1 | 204036_at | (D)/1 | 1.35003E−234 | Male BP 0.68/0.022 |
| HTR2C 5-hydroxytryptamine (serotonin) receptor 2C, G protein-coupled | 207307_at | (I)/1 | 4.30E−02/2 | All 0.583/0.025 Male MDD 0.69/0.035 |
| CTTN cortactin | 214782_at | DE (I)/1 | 1.042E−19/4 | Male BP 0.76/0.0016 |
| PDCL3 phosducin-like 3 | 219043_s_at | (D)/2 | 1.37E−02/2 | All 0.6/0.009 Male SZ/SZA 0.65/0.030 |
| SNX6 sorting nexin 6 | 222410_s_at | DE (D)/1 | 0.0000068/4 | All 0.62/0.0025 Male SZ/SZA 0.65/0.024 |
| PIK3CA phosphatidylinositol-4,5-bisphosphate 3-kinase, catalytic subunit alpha | 231854_at | DE (D)/1 | 2.41E−37/4 | All 0.57/0.042 Male BP 0.65/0.047 |
| MBP myelin basic protein | 225408_at | (D)/2 | 8.34E−07/4 | |
| CCDC136 coiled-coil domain containing 136 | 226972_s_at | (D)/4 | 3.13E−03/2 | |
| AIMP1 aminoacyl tRNA synthetase complex-interacting multifunctional protein 1 | 227605_at | (D)/2 | 1.02E−05/4 | All 0.60/0.007 Male SZ/SZA 0.66/0.018 |

TABLE 3-continued

Top Universal Biomarkers for Suicide Across Genders

| Gene | Probe | Direction | p-value | Group |
|---|---|---|---|---|
| PITHD1<br>PITH (C-terminal proteasome-interacting domain of thioredoxin-like) domain containing 1 | 229856_s_at | (D)/4 | 0.000000067/4 | Female BP<br>0.83/0.031 |
| PCDH9<br>protocadherin 9 | 238919_at | (D)/2 | 6.61E−05/4 | |
| CAPZA2<br>capping protein (actin filament) muscle Z-line, alpha 2 | 201238_s_at | (D)/1 | 0.00029/2 | All<br>0.6/0.0086<br>Male BP<br>0.65/0.047 |
| PSME4<br>Proteasome Activator Subunit 4 | 237180_at | (I)/1 | 2.64E−36/4 | All<br>0.6/0.011<br>Male PTSD<br>0.79/0.0062 |
| GABRB1<br>gamma-aminobutyric acid (GABA) A receptor, beta 1 | 1557256_a_at | (I)/1 | 0.012/2 | Male BP<br>0.74/0.0034 |
| CNP<br>2',3'-cyclic nucleotide 3' phosphodiesterase | 1557943_at | (D)/1 | 0.019/2 | |
| RAP1A<br>RAP1A, member of RAS oncogene family | 202362_at | (D)/1 | 0.035/2 | All<br>0.6/0.011<br>Male BP<br>0.71/0.0082 |
| NGFR<br>nerve growth factor receptor | 205858_at | (I)/1 | 2.24E−15/4 | All<br>0.59/0.018<br>Male SZ/SZA<br>0.72/0.0020 |
| CAMK2B<br>calcium/calmodulin-dependent protein kinase II beta | 209956_s_at | DE<br>(I)/1 | 0.00078/2 | All<br>0.62/0.0017<br>Male BP<br>0.74/0.0029 |
| CLN5<br>ceroid-lipofuscinosis, neuronal 5 | 214252_s_at | DE<br>(D)/1 | 1.79E−15/4 | All<br>0.65/0.0002<br>Male SZ/SZA<br>0.68/0.010 |
| CLTA<br>clathrin, light chain A | 216295_s_at | DE<br>(D)/1 | 1.74E−15/4 | All<br>0.64/0.0006<br>Male BP<br>0.73/0.0049 |
| DOCK8<br>dedicator of cytokinesis 8 | 232843_s_at | DE<br>(D)/1 | 0.0022/2 | All<br>0.6/0.0079<br>Male BP<br>0.78/0.00078 |
| RARS2<br>arginyl-tRNA synthetase 2, mitochondrial | 232902_s_at | DE<br>(D)/1 | 0.022/2 | All<br>0.63/0.0014<br>Male SZ/SZA<br>0.70/0.0043 |
| PTK2<br>protein tyrosine kinase 2 | 241453_at | DE<br>(I)/1 | 2.87E−32/4 | All<br>0.61/0.0045<br>Male MDD<br>0.69/0.033 |
| PLCL1<br>phospholipase C-like 1 | 241859_at | (D)/1 | 0.040/2 | Male PTSD<br>0.78/0.0083 |
| LPAR1<br>lysophosphatidic acid receptor 1 | 204038_s_at | (D)/2 | 1.66E−04/2 | |
| AK2<br>adenylate kinase 2 | 205996_s_at | (D)/2 | 0.00000011/4 | All<br>0.64/0.0005<br>Male SZ/SZA<br>0.74/0.0012 |
| APLP2<br>amyloid beta (A4) precursor-like protein 2 | 208703_s_at | (D)/2 | 3.65E−02/2 | |

TABLE 3-continued

Top Universal Biomarkers for Suicide Across Genders

| | | | | | |
|---|---|---|---|---|---|
| BACE1<br>beta-site APP-<br>cleaving enzyme 1 | 224335_s_at | (I)/1 | 0.00037/2 | | All<br>0.58/0.032<br>Male BP<br>0.67/0.024 |
| ELOVL5<br>ELOVL fatty<br>acid elongase 5 | 214153_at | (I)/1 | 0.0028/2 | | Male PTSD<br>0.76/0.012 |
| KIF2C<br>kinesin family<br>member 2C | 211519_s_at | (D)/4 | 0.014/2 | | |

| Gene Symbol<br>Gene Name | Significant<br>Prediction of<br>Future<br>Hospitalizations<br>for<br>Suicidality<br>Across All<br>and Best in a<br>Diagnostic<br>Group<br>ROC AUC/<br>p-value | Convergent<br>Genetic and Brain<br>Evidence For<br>Involvement in<br>Suicide | Other Psychiatric<br>and Related<br>Disorders Evidence | Drugs that<br>Modulate the<br>Biomarker in<br>Opposite<br>Direction to<br>Suicide |
|---|---|---|---|---|
| BCL2<br>B-cell<br>CLL/lymphoma 2 | Male PTSD<br>0.83/0.013 | 5 | Aging<br>Alcoholism<br>Anxiety<br>BP<br>Mood Disorders<br>PTSD<br>SZ | Omega-3<br>Lithium |
| CD164<br>CD164 molecule,<br>sialomucin | Male PTSD<br>0.96/0.0004 | 4 | BP<br>Cocaine<br>Dependence<br>Stress | Clozapine |
| CD47<br>CD47 molecule | Male PTSD<br>0.87/0.0048 | 4 | MDD<br>Stress<br>SZ | Clozapine<br>Omega-3 |
| DLG1<br>discs, large<br>homolog 1<br>(*Drosophila*) | Male PTSD<br>0.9/0.0023 | 4 | Alcoholism<br>BP<br>MDD<br>SZ | Omega-3 |
| DLG1<br>discs, large<br>homolog 1<br>(*Drosophila*) | Male PTSD<br>0.79/<br>0.028 | 4 | Alcoholism<br>BP<br>MDD<br>SZ | Omega-3 |
| DYRK2<br>dual-specificity<br>tyrosine-(Y)-<br>phosphorylation<br>regulated kinase 2 | Male PTSD<br>0.93/0.001 | 4 | Aging<br>BP<br>MDD<br>Sleep Disorders | Clozapine |
| ITGB1BP1<br>integrin beta 1<br>binding protein 1 | Male PTSD<br>0.83/0.013 | 4 | Alzheimer's Disease<br>BP<br>Mood Disorders<br>SZ | Lithium |
| APOE<br>apolipoprotein E | | 6 | Aggression<br>Aging<br>Alcoholism<br>Alzheimer's Disease<br>Autism<br>Dementia<br>Depression-related<br>Longevity<br>MDD<br>Psychosis<br>PTSD<br>SZ | Omega-3 |
| MRPS14<br>mitochondrial<br>ribosomal protein<br>S14 | Male PTSD<br>0.84/0.0093 | 4 | SZ | Omega-3 |
| MRPS14<br>mitochondrial<br>ribosomal protein<br>S14 | Male PTSD<br>0.77/0.035 | 4 | SZ | Omega-3 |
| IL6<br>interleukin 6 | Female PTSD<br>1/0.028 | 6 | Aggression<br>Anxiety<br>BP | |

TABLE 3-continued

Top Universal Biomarkers for Suicide Across Genders

| Gene | Group | n | Associated | Drug |
|---|---|---|---|---|
| | | | Cognition | |
| | | | Dementia | |
| | | | Depression | |
| | | | Longevity | |
| | | | MDD | |
| | | | Mood Disorders | |
| | | | Panic | |
| | | | Psychosis | |
| | | | PTSD | |
| | | | Sleep Disorders | |
| | | | Stress | |
| | | | SZ | |
| AKAP13 A kinase (PRKA) anchor protein 13 | All 0.57/0.047 Male PTSD 0.80/0.022 | 4 | Cocaine Dependence Panic Stress | Clozapine |
| SECISBP2L SECIS binding protein 2-like | Male PTSD 0.89/0.0034 | 4 | Cocaine Dependence MDD SZ | Clozapine |
| SOD2 superoxide dismutase 2, mitochondrial | Male PTSD 0.85/0.010 | 5 | Longevity MDD Methamphetamine Abuse Mood Disorders SZ | Clozapine |
| LHFP lipoma HMGIC fusion partner | Male MDD 0.79/0.004 | 4 | SZ | Omega-3 |
| SKA2 spindle and kinetochore associated complex subunit 2 | Male PTSD 0.84/0.0093 | 8 | PTSD Stress | |
| GSK3B glycogen synthase kinase 3 beta | Male PTSD 0.84/0.0093 | 6 | Aging Alcoholism BP Dementia Depression Mood Stabilizers response Lithium response MDD SZ | Lithium |
| ITPKB inositol-trisphosphate 3-kinase B | Male PTSD 0.87/0.0048 | 4 | Aging Alcoholism Alzheimer's Disease Autism BP MDD Multiple Sclerosis Stress SZ SZA | Omega-3 |
| MTERF4 mitochondrial transcription termination factor 4 | Male PTSD 0.94/0.0006 | 4 | Stress | |
| GDI2 GDP dissociation inhibitor 2 | | 4 | BP MDD Mood Disorders SZ | Clozapine |
| PRKAR1A protein kinase, cAMP-dependent, regulatory, type I, alpha | Male PTSD 0.90/0.0023 | 4 | Alcoholism BP Epilepsy Mood Disorders Stress SZ | |
| NR3C1 nuclear receptor subfamily 3, group C, member 1 (glucocorticoid receptor) | Male PTSD 0.91/0.0015 | 5 | Alcoholism Anxiety BP Depression Longevity MDD PTSD Response to escitalopram (SSRI) Response to | Clozapine |

TABLE 3-continued

Top Universal Biomarkers for Suicide Across Genders

| Gene | Group | Score | Associations | Drug |
|---|---|---|---|---|
| | | | Nortriptyline (TCA) | |
| | | | Stress | |
| | | | SZ | |
| ADK adenosine kinase | Male PTSD 0.84/0.0093 | 0 | Depression | Omega-3 |
| PGK1 phosphoglycerate kinase 1 | | 4 | Alcoholism BP MDD SZ SZA | Clozapine |
| ZFYVE21 zinc finger, FYVE domain containing 21 | All 0.58/0.030 Male MDD 0.78/0.0044 | 4 | SZ | |
| RBM3 RNA binding motif (RNP1, RRM) protein 3 | Female PTSD 1/0.028 | 4 | Epilepsy Response to Lithium SZ | Omega-3 Lithium |
| FAM107B family with sequence similarity 107, member B | Male PTSD 0.93/0.001 | 4 | BP MDD Psychosis Response to Lithium Sleep Disorder SZ | Lithium |
| ECHDC1 enoyl CoA hydratase domain containing 1 | Male PTSD 0.94/0.0006 | 4 | Addictions BP PTSD | |
| TBL1XR1 transducin (beta)-like 1 X-linked receptor 1 | Female PTSD 1/0.028 | 2 | Alcoholism BP Longevity | Clozapine |
| LONRF2 LON peptidase N-terminal domain and ring finger 2 | Male PTSD 0.77/0.039 | 5 | Stress BP | Omega-3 |
| QKI QKI, KH domain containing, RNA binding | All 0.58/0.031 | 4 | BP Longevity MDD PTSD Stress SZ | Omega-3 |
| YWHAH tyrosine 3-monooxygenase/tryptophan 5-monooxygenase activation protein, eta | | 4 | Alcoholism BP Longevity MDD SZ | Omega-3 |
| SLC4A4 solute carrier family 4 (sodium bicarbonate cotransporter), member 4 | | 6 | Circadian abnormalities Longevity MDD SZ | |
| GDI2 GDP dissociation inhibitor 2 | | 4 | BP MDD Mood Disorders SZ | Clozapine |
| UQCRC2 ubiquinol-cytochrome c reductase core protein II | Male PTSD 0.81/0.017 | 4 | ADHD Alcohol BP MDD Multiple Sclerosis SZ | Omega-3 |
| CTNNB1 catenin (cadherin-associated protein), beta 1, 88 kDa | Male PTSD 0.80/0.022 | 4 | MDD PTSD Stress SZ | Clozapine |
| PSMB4 proteasome (prosome, macropain) subunit, beta type, 4 | Male PTSD 0.80/0.022 | 4 | BP MDD SZ SZA | |

TABLE 3-continued

Top Universal Biomarkers for Suicide Across Genders

| | | | | |
|---|---|---|---|---|
| PRKACB protein kinase, cAMP-dependent, catalytic, beta | Male PTSD 0.96/0.0004 | 4 | Alcohol Alzheimer's Disease BP Chronic Fatigue Syndrome | Clozapine |
| LPAR1 lysophosphatidic acid receptor 1 | | 4 | Aging BP Longevity MDD Mood PTSD SZ | Clozapine Omega-3 |
| HTR2C 5-hydroxytryptamine (serotonin) receptor 2C, G protein-coupled | | 6 | Affective Disorder Alcohol Antipsychotics BP MDD Mood Disorders Panic Disorder SZ | Clozapine |
| CTTN cortactin | | 4 | BP Effect of valproate MDD Stress | Clozapine Omega-3 |
| PDCL3 phosducin-like 3 | Male PTSD 0.80/ 0.022 | 5 | Sleep Disorders | |
| SNX6 sorting nexin 6 | Male PTSD 0.86/ 0.0068 | 4 | Panic | 0 |
| PIK3CA phosphatidylinositol-4,5-bisphosphate 3-kinase, catalytic subunit alpha | | 4 | Longevity MDD Stress SZ | Lithium |
| MBP myelin basic protein | | 4 | Alcohol Alzheimer's Disease BP MDD Mood Disorders SZ | Clozapine Omega-3 Lithium |
| CCDC136 coiled-coil domain containing 136 | | 4 | Psychosis | Clozapine |
| AIMP1 aminoacyl tRNA synthetase complex-interacting multifunctional protein 1 | Male PTSD 0.93/ 0.001 | 4 | | |
| PITHD1 PITH (C-terminal proteasome-interacting domain of thioredoxin-like) domain containing 1 | Male PTSD 0.87/ 0.0048 | | BP Psychosis SZ | |
| PCDH9 protocadherin 9 | | 4 | Aging MDD Psychosis SZ | Clozapine Omega-3 |
| CAPZA2 capping protein (actin filament) muscle Z-line, alpha 2 | Male PTSD 0.93/ 0.001 | 4 | BP MDD PTSD SZ | |
| PSME4 Proteasome Activator Subunit 4 | | 4 | Autism | |

TABLE 3-continued

Top Universal Biomarkers for Suicide Across Genders

| | | | | |
|---|---|---|---|---|
| GABRB1 gamma-aminobutyric acid (GABA) A receptor, beta 1 | | 4 | Alcohol Autism Mood Stabilizers BP MDD SZ SZA | |
| CNP 2',3'-cyclic nucleotide 3' phosphodiesterase | Female SZ/SZA 1/ 0.029 | 4 | Alcohol Epilepsy MDD Multiple Sclerosis Sleep Disorders SZ | Clozapine Omega-3 |
| RAP1A RAP1A, member of RAS oncogene family | Male PTSD 0.83/ 0.013 | 4 | Longevity SZ SZA | |
| NGFR nerve growth factor receptor | | 4 | MDD OCD Panic Disorder SZ | |
| CAMK2B calcium/calmodulin-dependent protein kinase II beta | | 4 | Addictions BP SZ | Clozapine |
| CLN5 ceroid-lipofuscinosis, neuronal 5 | Male PTSD 0.84/ 0.0093 | 4 | | |
| CLTA clathrin, light chain A | | 4 | Alzheimer's Disease BP MDD | |
| DOCK8 dedicator of cytokinesis 8 | Male PTSD 0.76/ 0.044 | 4 | ADHD Longevity | |
| RARS2 arginyl-tRNA synthetase 2, mitochondrial | Male PTSD 0.86/ 0.0068 | 4 | PTSD BP | |
| PTK2 protein tyrosine kinase 2 | | 4 | Alcohol Autism BP Circadian abnormalities MDD Psychosis Stress SZ | 0 |
| PLCL1 phospholipase C-like 1 | | 4 | Alcohol Psychosis SZ | Clozapine |
| LPAR1 lysophosphatidic acid receptor 1 | | 4 | Aging BP Longevity MDD Mood Disorders PTSD SZ | Clozapine Omega-3 |
| AK2 adenylate kinase 2 | | 2 | BP SZ | |
| APLP2 amyloid beta (A4) precursor-like protein 2 | | 4 | BP Depression Effect of valproate Chronic Fatigue Syndrome | Lithium Omega-3 |
| BACE1 beta-site APP-cleaving enzyme 1 | | 4 | Alzheimer's Disease Cocaine Dependence MDD Psychosis | |

TABLE 3-continued

Top Universal Biomarkers for Suicide Across Genders

| | | |
|---|---|---|
| ELOVL5<br>ELOVL fatty<br>acid elongase 5 | 3 | Alcohol<br>Autism<br>BP<br>Circadian<br>abnormalities<br>Cocaine<br>Dependence<br>MDD<br>Mood Disorders |
| KIF2C<br>kinesin family<br>member 2C | | |

Particularly suitable subjects are humans. Suitable subjects can also be experimental animals such as, for example, monkeys and rodents, that display a behavioral phenotype associated with suicide, for example, a mood disorder or psychosis. In one particular aspect, the subject is a female human. In another particular aspect, the subject is a male human.

In another aspect, the subject can further be diagnosed with a psychiatric disorder as known in the art. In particular aspects, the psychiatric disorder can be bipolar disorder, major depressive disorder, schizophrenia, and schizoaffective disorder, post-traumatic stress disorder, and combinations thereof.

In one embodiment, the subject can be diagnosed as having or as suspected of having bipolar disorder (BP) and the biomarker can be selected from DTNA; HS3ST3B1; CADM1; Unknown gene; KSR1; CD44; DAPP1; OPRM1; SPTBN1; AKT1S1; SAT1; C20orf27; and combinations thereof. As summarized in FIG. 17, the biomarker expression level can increase above a reference expression level of the biomarker or decrease below a reference expression level of the biomarker.

In another embodiment, the subject can be diagnosed as having or as suspected of having depression (MDD) and the biomarker can be selected from PHF20; EIF1B-AS1; TLN1; NUCKS1; DLK1; BBIP1; BDNF; SKA2; IL10; GATM; PRPF40A; and combinations thereof. As summarized in FIG. 17, the biomarker expression level can increase above a reference expression level of the biomarker or decrease below a reference expression level of the biomarker.

In another embodiment, the subject can be diagnosed as having or as suspected of having schizoaffective disorder (SZA) and the biomarker can be selected from USP48; NPRL3; TSPYL1; TMSB15B; IL6; TNS1; TNF; S100B; JUN; BATF2; ANXA11; and combinations thereof. As summarized in FIG. 17, the biomarker expression level can increase above a reference expression level of the biomarker or decrease below a reference expression level of the biomarker.

In another embodiment, the subject can be diagnosed as having or as suspected of having schizophrenia (SZ) and the biomarker can be selected from RP11-389C8.2; CYB561; LOC100128288; CDDC163P; C1orf61; SKA2; BDNF; HTR2A; SLC5A3; ATP6V0E1; JUN; LOC100131662; and combinations thereof. As summarized in FIG. 17, the biomarker expression level can increase above a reference expression level of the biomarker or decrease below a reference expression level of the biomarker.

A particularly suitable sample for which the expression level of a biomarker is determined can be, for example, blood, including whole blood, serum, plasma, leukocytes, and megakaryocytes.

The method can further include assessing mood, anxiety, and other like psychiatric symptoms, and combinations thereof in the subject using questionnaires and/or a computer-implemented method for assessing mood, anxiety, other like psychiatric symptoms, and combinations thereof. In one aspect, the method is implemented using a first computer device coupled to a memory device, the method comprising: receiving mood information, anxiety information, and combinations thereof into the first computer device; storing, by the first computer device, the mood information, anxiety information, and combinations thereof in the memory device; computing, by the first computer device, of the mood information, anxiety information, and combinations thereof, a score that can be used to predict suicidality; presenting, by the first computer device, in visual form the mood information, anxiety information, and combinations thereof to a second computer device; receiving a request from the second computer device for access to the mood information, anxiety information, and combinations thereof; and transmitting, by the first computer device, the mood information, anxiety information, and combinations thereof to the second computer device to assess mood, anxiety, and combinations thereof in the subject. Suitable mood and anxiety information is described herein in more detail below.

The method can further include assessing socio-demographic/psychological suicidal risk factors in the subject using a computer-implemented method for assessing socio-demographic/psychological suicidal risk factors in the subject, the method implemented using a first computer device coupled to a memory device, the method comprising: receiving socio-demographic/psychological suicidal risk factor information into the first computer device; storing, by the first computer device, the socio-demographic/psychological suicidal risk factor information in the memory device; presenting, by the first computer device, in visual form the socio-demographic/psychological suicidal risk factor information to a second computer device; receiving a request from the second computer device for access to socio-demographic/psychological suicidal risk factor information; and transmitting, by the first computer device, the socio-demographic/psychological suicidal risk factor information to the second computer device to assess the socio-demographic/psychological suicidal risk factors in the subject. Suitable socio-demographic/psychological suicidal risk factors are described herein in more detail below.

In accordance with the present disclosure, biomarkers useful for objectively predicting future hospitalization due to suicidality in subjects have been discovered. In one aspect, the present disclosure is directed to a method for future hospitalization due to suicidality in a subject. The method includes obtaining a first expression level of a blood biomarker in an initial sample obtained from the subject; and determining a second expression level of the blood biomarker in a subsequent sample obtained from the subject, wherein an increase in the expression level of the blood biomarker in the subsequent sample obtained from the subject as compared to the expression level of the initial sample indicates a higher risk of future hospitalizations due to suicidality. In some embodiments, the methods further include obtaining clinical risk factor information and clinical scale data such as for anxiety, mood and/or psychosis from the subject in addition to obtaining blood biomarker expression level in a sample obtained from the subject.

Suitable biomarkers for predicting future hospitalization due to suicidality in a subject wherein an increase in the expression level of the blood biomarker occurs can be, for example, the blood biomarker(s) set forth in Table 1.

In another embodiment, the expression level of the blood biomarker in the sample obtained from the subject is increased as compared to the reference expression level of the biomarker. Suitable biomarkers that indicate a risk for future hospitalization due to suicidality when the expression level increases in males as compared to the reference expression level have been found to include, for example, solute carrier family 4 (sodium bicarbonate cotransporter), member 4 (SLC4A4), cell adhesion molecule 1 CADM1, dystrobrevin, alpha (DTNA), spermidine/spermine N1-acetyltransferase 1 (SAT1), interleukin 6 (interferon, beta 2) (IL6) and combinations thereof. Suitable biomarkers that indicate a risk for future hospitalization due to suicidality when the expression level increases in females as compared to the reference expression level have been found to include, for example, erythrocyte membrane protein band 4.1 like 5 (EPB41L5), HtrA serine peptidase 1 (HTRA1), deleted in primary ciliary dyskinesia homolog (DPCD), general transcription factor IIIC, polypeptide 3, 102 kDa (GTF3C3), period circadian clock 1 (PER1), pyridoxal-dependent decarboxylase domain containing 1 (PDXDC1), kelch-like family member 28 (KLHL28), ubiquitin interaction motif containing 1 (UIMC1), sorting nexin family member 27 (SNX27) and combinations thereof.

In another embodiment, the expression level of the blood biomarker in the sample obtained from the subject is decreased as compared to the reference expression level of the biomarker. Suitable biomarkers that indicate a risk for future hospitalization due to suicidality when the expression level decreases in males as compared to the reference expression level have been found to include, for example, spindle and kinetochore associated complex subunit 2 (SKA2), CAP-GLY domain containing linker protein family, member 4 (CLIP4), kinesin family member 2C (KIF2C), kelch domain containing 3 (KLHDC3) and combinations thereof. Suitable biomarkers that indicate a risk for future hospitalization due to suicidality when the expression level decreases in females as compared to the reference expression level have been found to include, for example, phosphatidylinositol 3-kinase, catalytic subunit type 3 (PIK3C3), aldehyde dehydrogenase 3 family, member A2 (ALDH3A2), ARP3 actin-related protein 3 homolog (yeast) (ACTR3), B-cell CLL (BCL2), MOB kinase activator 3B (MOB3B), casein kinase 1, alpha 1 (CSNK1A1), La ribonucleoprotein domain family, member 4 (LARP4), zinc finger protein 548 (ZNF548) and combinations thereof.

Particularly suitable subjects are humans. Suitable subjects can also be experimental animals such as, for example, monkeys and rodents, that display a behavioral phenotype associated with suicide, for example, a mood disorder or psychosis. In one particular embodiment, the subject is a female human. In another particular aspect, the subject is a male human.

In another aspect, the subject can further be diagnosed with a psychiatric disorder. The psychiatric disorder can be bipolar disorder, major depressive disorder, schizophrenia, and schizoaffective disorder, post-traumatic stress disorder and combinations thereof.

A particularly suitable sample for which the expression level of a biomarker is determined can be, for example, blood, including whole blood, serum, plasma, leukocytes, and megakaryocytes.

Suitable biomarkers found to have a difference in expression level include, for example, spermidine/spermine N1-acetyltransferase 1 (SAT1), interleukin 6 (interferon beta 2) (IL6), solute carrier family 4 (sodium bicarbonate cotransporter), member 4 (SLC4A4), spindle and kinetochore associated complex subunit 2 (SKA2), jun proto-oncogen (JUN), cell adhesion molecule 1 (CADM1), dystrobrevin alpha (DTNA), monoamine oxidase B (MAOB), myristoylated alanine-rich protein kinase C substrate (MARCKS), phosphatase and tensin homolog (PTEN), fatty acid desaturase 1 (FADS1), Rho GTPase activating protein 26 (ARHGAP26), B-cell CLL/lymphoma 2 (BCL2), cadherin 4 type 1 R cadherin (retinal) (CDH4), chemokine (C-X-C motif) ligand 11 (CXCL11), EMI domain containing 1 (EMID1), family with sequence similarity 49 member B (FAM49B), GRINL1A complex locus (GCOM1), hippocalcin-like 1 (HPCAL1), mitogen-activated protein kinase 9 (MAPK9), nuclear paraspeckle assembly transcript 1 (NEAT1), protein tyrosine kinase 2 (PTK2), RAS-like family 11 member B (RASL11B), small nucleolar RNA H/ACA box 68 (SNORA68), superoxide dismutase 2 mitochondrial (SOD2), transcription factor 7-like 2 (T-cell specific HMG-box) (TCF7L2), v-raf murine sarcoma viral oncogene homolog (BRAF), Chromosome 1 Open Reading Frame 61 (C1orf61), calreticulin (CALR), calcium/calmodulin-dependent protein kinase II beta (CAMK2B), caveolin 1 caveolae proein 22 kDa (CAV1), chromodomain helicase DNA binding protein 2 (CHD2), cAMP responsive element modulators (CREM), cortactin (CTTN), dishevelled associated activator of morphogenesis 2 (DAAM2), Dab mitogen responsive phosphoprotein homolog 2 (DAB2), GABA(A) receptor associated protein like 1 (GABARAPL1), glutamate-ammonia ligase (GLUL), helicase with zinc finger (HELZ), immunoglobulin heavy chain constant gamma 1 (IGHG1), interleukin 1 beta (IL1B), jun B proto-oncogen (JUNB), lipoma HMGIC fusion partner (LHFP), metallothionein 1 E (MT1E), metallothionein 1 H (MT1H), metallothionein 2 (MT2A), N-myc downstream regulated 1 (NDRG1), nucleobindin 2 (NUCB2), PHD finger protein 20-like 1 (PHF20L1), cysteine-rich protein with kazal motifs (RECK), shisa family member 2 (SHISA2), transmembrane 4 L six family member 1 (TM4SF1), trophoblast glycoprotein (TPBG), tumor protein D52-like 1 (TPD52L1), TSC22 domain family member 3 (TSC22D3), vacuole membrane protein 1 (VMP1), ZFP 36 ring finger protein (ZFP36), zink finger FYVE domain containing 21 (ZHX2), histone cluster 1 H2bo (HIST1H2BO), keratocan (KERA), transcription factor Dp-1 (TFDP1), Single-Stranded DNA Binding Protein 2 (SSBP2), Transcription Factor EC (TFEC), Diphosphoinositol Pentakisphosphate Kinase 1 (PPIP5K1), Fibroblast Growth Factor Receptor 1 Oncogene Partner 2 (FGFR1OP2), Zinc Finger MYND-Type Containing 8 (ZMYND8), Interferon Gamma (IFNG), Brain-Derived Neurotrophic Factor (BDNF), cAMP Responsive Element Binding Protein 1 (CREB1), Hes Family BHLH Transcription Factor 1 (HES1), Ankyrin Repeat And MYND Domain Containing 1 (ANKMY1), Aldehyde Dehydrogenase 3 Family Member A2 (ALDH3A2), Heparan Sulfate (Glucosamine) 3-O-Sulfotransferase 3B1 (HS3ST3B1), Kinase Suppressor Of Ras 1 (KSR1), Dual Adaptor Of Phosphotyrosine And 3-Phosphoinositides (DAPP1), Opioid Receptor Mu 1 (OPRM1), Spectrin Beta Non-Erythrocytic 1 (SPTBN1), PHD Finger Protein 20 (PHF20), EIF1B Antisense RNA 1 (EIF1B-AS1), Talin 1 (TLN1), Nuclear Casein Kinase And Cyclin-Dependent Kinase Substrate 1 (NUCKS1), Delta-Like 1 Homolog (DLK1), BBSome Interacting Protein 1 (BBIP1), Interleukin 10 (IL10), Glycine Amidinotransferase (GATM), PRP40 Pre-MRNA Processing Factor 40 Homolog A (PRPF40A), Ubiquitin Specific Peptidase 48 (USP48), Nitrogen Permease Regulator-Like 3 (NPRL3), Testis-Specific Y-Encoded-Like Protein-Like 1 (TSPYL1), thymosin beta 15B (TMSB15B), Minichromosome Maintenance Complex Component 8 (MCM8), tensin 1 (TNS1), Tumor Necrosis Factor (TNF), S100 Calcium Binding Protein B (S100B), Basic Leucine Zipper Transcription Factor ATF-Like 2 (BATF2), Annexin A11 (ANX11), RP11-389C8.2, Cytochrome B561 (CYB561), LOC100128288 (Uncharacterized LOC100128288), Coiled-Coil Domain Containing 163 Pseudogene (CCDC163P), 5-Hydroxytryptamine (Serotonin) Receptor 2A, G Protein-Coupled (HTR2A), Annexin A11 (ANXA11), Uncharacterized LOC100131662 (LOC100131662), Prolylcarboxypeptidase (Angiotensinase C; PRCP), and combinations thereof. See, FIG. 9 for a list of biomarkers identified as showing a difference in expression level.

In another aspect, the present disclosure is directed to a method for mitigating suicidality in a subject in need thereof. The method includes: obtaining an expression level of a blood biomarker in a sample obtained from the subject; obtaining a reference expression level of the blood biomarker; identifying a difference in the expression level of the blood biomarker in the sample as compared to the reference expression level of the blood biomarker; and administering a treatment, wherein the treatment reduces the difference between the expression level of the blood biomarker in the sample as compared to the reference expression level of the blood biomarker to mitigate suicidality in the subject. As used herein, "mitigate", "mitigating", and the like refer to making a condition less severe and/or preventing a condition. More particularly, the phrase "mitigate suicidality" refers to reducing suicide ideation in a subject and/or preventing suicide completion.

Suitable treatments can be a lifestyle modification, administering a therapy, and combinations thereof.

Suitable therapy can be a nutritional, a drug and psychotherapy.

Particularly suitable nutritionals can be omega-3 fatty acids, including, by way of example, docosahexaenoic acid (DHA).

Particularly suitable drugs include, for example, ketamine, lithium, clozapine, selegeline, tocilizumab, siltuximab, enkephalin, methionine, gevokizumab, gallium nitrate, vemurafenib, dabrafenib, oblimersen, rasagiline, (−)-gossypol, navitoclax, gemcitabine/paclitaxel, bortezomib/paclitaxel, ABT-199, paclitaxel/trastuzumab, paclitaxel/pertuzumab/trastuzumab, lapatinib/paclitaxel, doxorubicin/paclitaxel, epirubicin/paclitaxel, paclitaxel/topotecan, paclitaxel, canakinumab, tesevatinib, enzastaurin, fomepizole, miglitol, anakinra, and combinations thereof. Other suitable drugs, as well as biomarkers found to be changed in opposite direction in suicide versus in treatments with omega-3 fatty acids, lithium, clozapine, or antidepressants (MAOIs) as listed in Tables 4 & 5. These biomarkers could potentially be used to stratify patients to different treatment approaches, and monitor their responses.

TABLE 4

Top candidate biomarker genes - drugs that modulate expression of these markers in the opposite direction in male subjects

| Gene symbol/<br>Gene Name | Discovery<br>(Change) Method/<br>Score | Modulated by<br>Omega-3 | Modulated by<br>Lithium | Modulated by<br>Clozapine | Other<br>Drugs |
|---|---|---|---|---|---|
| CCDC136<br>coiled-coil domain<br>containing 136 | (D)<br>AP4 | | | (I)<br>Mouse<br>VT[356] | |
| CD44<br>CD44 molecule (Indian<br>blood group) | (D)<br>DE2 | | | (I)<br>Mouse<br>Blood[356] | |
| IL6<br>interleukin 6 (interferon,<br>beta 2) | (I)<br>AP2 | (D)<br>Human<br>Blood[357] | | | tocilizumab<br>siltuximab |
| SAT1<br>spermidine/spermine N1-<br>acetyltransferase 1 | (I)<br>DE2<br>DE1 | (D)<br>Mouse<br>Blood[358] | | | |
| MAOB<br>monoamine oxidase B | (I)<br>DE1 | | | | selegiline |
| ARHGAP26<br>Rho GTPase activating<br>protein 26 | (I)<br>DE1 | | | (D)<br>Mouse<br>VT[356] | |
| BCL2<br>B-cell CLL/lymphoma 2 | (D)<br>DE1 | | (I)<br>Human<br>Blood[153] | (I)<br>Rat<br>Dentate gyrus<br>Hippocampus[359] | |
| EHBP1<br>EH domain binding protein 1 | (D)<br>DE 4 | | | (I) VT[356] | |
| FAM49B<br>family with sequence<br>similarity 49, member B | (I)<br>AP2 | (D)<br>Mouse<br>Blood[358] | | | |
| HPCAL1<br>hippocalcin-like 1 | (I)<br>DE2 | | | (D)<br>Mouse<br>VT[356] | |

TABLE 4-continued

Top candidate biomarker genes - drugs that modulate expression of these markers in the opposite direction in male subjects

| Gene symbol/ Gene Name | Discovery (Change) Method/ Score | Modulated by Omega-3 | Modulated by Lithium | Modulated by Clozapine | Other Drugs |
|---|---|---|---|---|---|
| MAPK9 mitogen-activated protein kinase 9 | (I) DE2 | | | (D) Mouse VT[356] | |
| NEAT1 nuclear paraspeckle assembly transcript 1 (non-protein coding) | (I) DE2 | | | (D) Mouse VT[356] | |
| RASL11B RAS-like, family 11, member B | (I) AP2 | | | (D) Mouse Caudate putamen[356] | |
| TRAK2 trafficking protein, kinesin binding 2 | (D) DE2 | (I) Mouse Blood[358] | (I) Mouse PFC[360] | | |
| ADRBK1 adrenergic, beta, receptor kinase 1 | (D) DE1 | | | (I) Mouse PFC[361] | |
| BRAF v-raf murine sarcoma viral oncogene homolog B | (I) DE1 | | | | Vemurafenib Dabrafenib |
| CAMK2B calcium/calmodulin-dependent protein kinase II beta | (I) DE1 | | | (D) Mouse striatum[362] | |
| CNP 2',3'-cyclic nucleotide 3' phosphodiesterase | (D) AP1 | (I) Mouse Hippocampus[358] | | (I) Mouse AMY[356] | |
| CTTN cortactin | (I) DE1 | (D) Mouse Blood[358] | | (D) Mouse VT[356] | |
| G2E3 G2/M-phase specific E3 ubiquitin protein ligase | (D) AP1 | (I) Mouse Hippocampus[358] | | | |
| GABARAPL1 GABA(A) receptor-associated protein like 1 | (I) DE1 | (D) Mouse Blood[358] | | | |
| HELZ helicase with zinc finger | (I) DE1 | (D) Mouse Blood[358] | | | |
| IL1B interleukin 1, beta | (I) DE1 | (D) Mouse Blood[358] | | | canakinumab gevokizumab gallium nitrate |
| LHFP lipoma HMGIC fusion partner | (I) DE1 | (D) Mouse Blood[358] | | | |
| LPAR1 lysophosphatidic acid receptor 1 | (D) AP1 | (I) Mouse Hippocampus, Blood[358] | | (I) Mouse AMY[356] | |
| MBP myelin basic protein | (D) AP1 | (I) Mouse Blood[358] | (I) Oligodendrocytes[363] Mouse Brain[360] | (I) Mouse AMY and Blood[356] | |
| MEF2C myocyte enhancer factor 2C | (D) DE1 | | | (I) Mouse Hippocampus and VT[356] | |
| NDRG1 N-myc downstream regulated 1 | (I) DE1 | (D) Mouse Blood[358] | | | |
| OGFR opioid growth factor receptor | (D) DE1 | | | | enkephalin methionine |
| PCDH9 protocadherin 9 | (D) AP1 | | | (I) Mouse VT[356] | |
| PHF20L1 PHD finger protein 20-like 1 | (I) DE1 | (D) Mouse Blood[358] | | (D) Mouse Hippocampus[356] | |
| PRKCB protein kinase C, beta | (D) DE1 AP1 | | (I) Mouse PFC[360] AMY[364] | | |

TABLE 4-continued

Top candidate biomarker genes - drugs that modulate expression of these markers in the opposite direction in male subjects

| Gene symbol/ Gene Name | Discovery (Change) Method/ Score | Modulated by Omega-3 | Modulated by Lithium | Modulated by Clozapine | Other Drugs |
|---|---|---|---|---|---|
| RBMX RNA binding motif protein, X-linked | (D) DE1 | (I) Mouse NAC, Blood[358] | | | |
| RNASEL ribonuclease L (2',5'-oligoisoadenylate synthetase-dependent) | (D) AP1 | (I) Mouse Blood[358] | | | |
| SNAP23 synaptosomal-associated protein, 23 kDa | (D) AP1 | | | (I) Mouse Blood[356] | |
| TM4SF1 transmembrane 4 L six family member 1 | (I) DE1 | (D) Mouse Blood[358] | | | |
| TSPAN33 tetraspanin 33 | (D) AP1 | (I) Mouse Blood[358] | | (I) Mouse VT[356] | |
| VMP1 vacuole membrane protein 1 | (I) DE1 | (D) Mouse Blood[358] | | | |
| ZFP36 ZFP36 ring finger protein | (I) DE1 | (D) Mouse Blood[358] | (D) Rat Brain[365] | | |
| BTBD3 BTB (POZ) domain containing 3 | (I) DE 4 | (D) Mouse AMY[358] | | | |
| CADM1 cell adhesion molecule 1 | (I) DE4 | | | (D) Mouse VT[356] | |
| CTBS chitobiase, di-N-acetyl- | (I) DE 4 | | | (D) VT [356] | |
| LAMB1 laminin, beta 1 | (I) AP4 | (D) Mouse HIP[358] | | | |
| PLEC plectin | (D) DE 4 | | | (I) Mouse VT[356] | |
| RAD23A RAD23 homolog A (*S. cerevisiae*) | (D) DE 4 | (I) Mouse Blood[358] | | | |
| SETD8 SET domain containing (lysine methyltransferase) 8 | (D) DE 4 | (I) Mouse Blood[358] | | | |
| TXNRD2 thioredoxin reductase 2 | (D) AP4 | | | (I) Mouse Blood[356] | |

(I): increase in biomarker expression;
(D): decrease in biomarker expression

TABLE 5

Top candidate biomarker genes - drugs that modulate expression of these markers in the opposite direction in female subjects

| Gene Symbol/ Gene Name | Discovery (Change) Method/ Score | Modulated by Omega-3 | Modulated by Lithium | Modulated by Clozapine | Other Drugs |
|---|---|---|---|---|---|
| Out of Validated Biomarkers (Bonferroni) (49 genes, 50 probesets) | | | | | |
| BCL2 B-cell CLL | (D) DE/2 | (I) FC (Chen, Zeng et al. 1999) (I) cerebellar granule cells (Chen and Chuang 1999) (I) Human Blood (Lowthert, Leffert et al. 2012) (I) Astrocyte (Keshavarz, | | (I) Hip (Bai, Zhang et al. 2004) | oblimersen, rasagiline, (−)-gossypol, navitoclax, gemcitabine/paclitaxel, bortezomib/paclitaxel, ABT-199, paclitaxel/trastuzumab, paclitaxel/pertuzumab/trastuzumab, lapatinib/paclitaxel, doxorubicin/paclitaxel, epirubicin/paclitaxel, paclitaxel/topotecan, paclitaxel |

TABLE 5-continued

Top candidate biomarker genes - drugs that modulate expression of these markers in the opposite direction in female subjects

| Gene Symbol/ Gene Name | Discovery (Change) Method/ Score | Modulated by Omega-3 | Modulated by Lithium | Modulated by Clozapine | Other Drugs |
|---|---|---|---|---|---|
| | | | Emamghoreishi et al. 2013) (I) HIP (Chen, Rajkowska et al. 2000) (I) Dentate gyrus, HIP(Hammonds and Shim 2009) | | |
| GSK3B glycogen synthase kinase 3 beta | (D) DE/1 | | (I) FC (Fatemi, Reutiman et al. 2009) | | enzastaurin |
| CAT catalase | (D) DE/2 | | Oxidative Stress BP (I) Plasma (de Sousa, Zarate et al. 2014) | | fomepizole |
| JUN jun proto-oncogene | (I) DE/2 DE/1 | | (D) leukocytes (Watanabe, Iga et al. 2014) | (D) FC (MacDonald, Eaton et al. 2005) | |
| MOB3B MOB kinase activator 3B | (D) DE/1 | (I) PFC (females) (Le-Niculescu, Case et al. 2011) | | | |
| NDRG1 N-myc downstream regulated 1 | (I) DE/1 | (D) Blood (Le-Niculescu, Case et al. 2011) | | | |
| SPON1 spondin 1, extracellular matrix protein | (D) DE/1 | | | (I) VT (Le-Niculescu, Balaraman et al. 2007) | |
| FOXP1 forkhead box P1 | (I) DE/4 | (D) Blood (Le-Niculescu, Case et al. 2011) | | | |
| HAVCR2 hepatitis A virus cellular receptor 2 | (I) DE/4 | | | (D) PFC (Jakovcevski, Bharadwaj et al. 2013) | |
| GJA1 gap junction protein, alpha 1, 43 kDa | (I) DE/1 | (D) HIP (females) (Le-Niculescu, Case et al. 2011) | | (D) VT (Le-Niculescu, Balaraman et al. 2007) | |
| CD84 CD84 molecule | (D) DE/2 | | | (I) Blood (Le-Niculescu, Balaraman et al. 2007) | |
| DCAF5 DDB1 andCUL4 associated factor 5 | (D) DE/2 | | | (I) VT (Le-Niculescu, Balaraman et al. 2007) | |
| GANC glucosidase, alpha; neutral C | (D) DE/2 | | | | miglitol |
| IL1R1 interleukin 1 receptor, type I | (I) AP/1 | | | | anakinra |
| INPP4A inositol polyphosphate-4-phosphatase, type I, 107 kDa | (D) DE/1 | | | (I) VT (Le-Niculescu, Balaraman et al. 2007) | |
| JRK Jrk homolog (mouse) | (D) AP/2 | (I) Brain(Hammamieh, Chakraborty et al. 2014) | | | |

TABLE 5-continued

Top candidate biomarker genes - drugs that modulate expression of these markers in the opposite direction in female subjects

| Gene Symbol/ Gene Name | Discovery (Change) Method/ Score | Modulated by Omega-3 | Modulated by Lithium | Modulated by Clozapine | Other Drugs |
|---|---|---|---|---|---|
| PDXDC1 pyridoxal-dependent decarboxylase domain containing 1 | (I) DE/2 | | | (D) VT (Le-Niculescu, Balaraman et al. 2007) | |
| SMARCA2 SWI | (D) DE/1 | (I) HIP (males) (Le-Niculescu, Case et al. 2011) | | | |
| Out of Top Discovery and Prioritization Biomarkers(Non Bonferroni Validated, 65 genes) | | | | | |
| CLTA clathrin, light chain A | (I) DE/4 | | | (D) FC (MacDonald, Eaton et al. 2005) | |
| PPM1B protein phosphatase, Mg2+ | (D) DE/4 | | | (I) VT (Le-Niculescu, Balaraman et al. 2007) | |
| AFF3 AF4/FMR2 family, member 3 | (I) AP/4; (I) DE/1 | (D) Blood (Le-Niculescu, Case et al. 2011) | | | |
| WAC WW domain containing adaptor with coiled-coil | (D) DE/4 | | | (I) VT (Le-Niculescu, Balaraman et al. 2007) | |
| AKT3 v-akt murine thymoma viral oncogene homolog 3 | (I) AP/4 | | | | enzastaurin |
| ARID4B AT rich interactive domain 4B (RBP1-like) | (D) DE/4 | (I) HIP (males) (Le-Niculescu, Case et al. 2011) | | | |
| ATXN1 ataxin 1 | (I) DE/4 | (D) Blood (Le-Niculescu, Case et al. 2011) | | | |
| BRE Brain and reproductive organ-expressed (TNFRSF1A modulator) | (I) AP/4 | | | (D) VT (Le-Niculescu, Balaraman et al. 2007) | |
| CSNK1A1 casein kinase 1, alpha 1 | (D) DE/4 | (I) Blood (Le-Niculescu, Case et al. 2011) | | | |
| ENTPD1 ectonucleoside triphosphate diphosphohydrolase 1 | (I) AP/4 | (D) Blood (Le-Niculescu, Case et al. 2011) | | (D) PFC (Jakovcevski, Bharadwaj et al. 2013) | |
| EPHB4 EPH receptor B4 | (I) DE/4 | | | | tesevatinib |
| ETNK1 ethanolamine kinase 1 | (D) AP/4 | (I) PFC (males)(Le-Niculescu, Case et al. 2011) | | | |
| ITIH5 inter-alpha-trypsin inhibitor heavy chain family, member 5 | (I) AP/4 | (D) Blood (Le-Niculescu, Case et al. 2011) | | (D) PFC (Jakovcevski, Bharadwaj et al. 2013) | |
| LARP4 La ribonucleoprotein domain family, member 4 | (D) DE/4 | | | (I) VT (Le-Niculescu, Balaraman et al. 2007) | |
| MBNL1 muscleblind-like splicing regulator 1 | (D) DE/4 | (I) HIP (males) (Le-Niculescu, Case et al. 2011) | | (I) Blood (Le-Niculescu, Balaraman et al. 2007) | |

TABLE 5-continued

Top candidate biomarker genes - drugs that modulate expression of these markers in the opposite direction in female subjects

| Gene Symbol/ Gene Name | Discovery (Change) Method/ Score | Modulated by Omega-3 | Modulated by Lithium | Modulated by Clozapine | Other Drugs |
|---|---|---|---|---|---|
| MR1 major histocompatibility complex, class I-related | (I) DE/4 | | | | Anti-Lymphocyte serum |
| PRDX3 peroxiredoxin 3 | (D) DE/4 | (I) Blood (Le-Niculescu, Case et al. 2011) | | | |
| RAB22A RAB22A, member RAS oncogene family | (D) DE/4 | | | (I) Blood (Le-Niculescu, Balaraman et al. 2007) | |
| SNX27 sorting nexin family member 27 | (I) AP/4 | | | (D) AMY (Le-Niculescu, Balaraman et al. 2007) | |
| SSBP2 single-stranded DNA binding protein 2 | (I) AP/4 | (D) Blood(Le-Niculescu, Case et al. 2011) | | (D) VT (Le-Niculescu, Balaraman et al. 2007) | |
| WAPAL wings apart-like homolog (*Drosophila*) | (D) DE/4 | | (I) SK-N-AS cells (ATCC derived from a human neuroblastoma cell (Seelan, Khalyfa et al. 2008) | (I) VT (Le-Niculescu, Balaraman et al. 2007) | |

(I): increase in biomarker expression;
(D): decrease in biomarker expression

More particularly, it has been found that BCL2, JUN, GHA1, ENTPD1, ITIH5, MBNL1, and SSBP2 are changed in expression by the above listed treatments, and in particular therapies such as nutritionals and drugs, suggesting these biomarkers may be core to the anti-suicidal mechanism of these drugs. Further, BCL2, CAT, and JUN may be useful blood pharmacogenomic markers of response to lithium. CD84, MBNL1, and RAB22A may be useful blood pharmacogenomic markers of response to clozapine. NDRG1, FOXP1, AFF3, ATXN1, CSNK1A1, ENTPD1, ITIH5, PRDX3, and SSBP2 may be useful blood pharmacogenomic markers of response to omega-3 fatty acids. Three existing drugs, used for other indications, have been identified as targeting the top suicide biomarkers identified in the present disclosure, and could potentially be re-purposed for testing in treatment of acute suicidality: anakinra (inhibiting ILR1), enzastaurin (inhibiting AKT3), and tesevatinib (inhibiting EPHB4). Additionally, Connectivity Map analyses (FIGS. 34A-34C) identified novel compounds that induce gene expression signatures that are the opposite of those present in suicide, and might generate leads and/or be tested for use to treat/prevent suicidality: betulin (an anti-cancer compound from the bark of birch trees), zalcitabine (an anti-HIV drug), and atractyloside (a toxic glycoside). Other common drugs identified by the Connectivity Map analyses are nafcillin, lansoprazole, mifepristone, LY294002, minoxidil, acetysalicilic acid, estradiol, buspirone, dicloxacillin, corticosterone, metformin, diphenhydramine, haloperidol, metaraminol, yohimbine, trimethadione and fluoxetine (see also Table 6, 7, and 8).

TABLE 6

Therapeutic Compounds for Suicidality across Gender

| Therapeutic compound/Drug | Score* |
|---|---|
| fluoxetine | −0.812 |
| betulin | −0.812 |
| dl-alpha tocopherol | −0.821 |
| haloperidol | −0.823 |
| hesperidin | −0.824 |
| calcium folinate | −0.825 |
| harpagoside | −0.826 |
| trimipramine | −0.836 |
| rilmenidine | −0.845 |
| tenoxicam | −0.851 |
| chlorpromazine | −0.852 |
| harman | −0.858 |
| homatropine | −0.863 |
| ramifenazone | −0.864 |
| clozapine | −0.866 |
| diphenhydramine | −0.873 |
| prochlorperazine | −0.874 |
| pirenperone | −0.876 |
| asiaticoside | −0.886 |
| adiphenine | −0.923 |
| verapamil | −0.922 |
| metaraminol | −0.936 |
| vohimbine | −0.958 |
| metformin | −0.983 |
| trimethadione | −1 |
| chlorogenic acid | −1 |

*Score of −1 means maximum opposite effect.

TABLE 7

Therapeutic Compounds for Suicidality in Men

| Therapeutic compound/drug | Score* |
|---|---|
| thiamine | −0.778 |
| homatropine | −0.789 |
| vitexin | −0.794 |
| ergocalciferol | −0.801 |
| tropicamide | −0.801 |
| (−)-atenolol | −0.817 |
| betulin | −0.905 |
| spaglumic acid | −1 |

*Score of −1 means maximum opposite effect.

TABLE 8

Therapeutic Compounds for Suicidality in Women

| Therapeutic compound/drug | Score* |
|---|---|
| mifepristone | −0.797 |
| lansoprazole | −0.888 |
| nafcillin | −0.895 |
| betulin | −1 |

*Score of −1 means maximum opposite effect.

In another aspect, the subject can further be diagnosed with a psychiatric disorder. The psychiatric disorder can be any psychiatric disorder known in the art, including, for example, bipolar disorder, major depressive disorder, schizophrenia, and schizoaffective disorder, post-traumatic stress disorder, and combinations thereof.

In another aspect, the present disclosure is directed to a questionnaire and/or a computer-implemented method for assessing mood, anxiety, and combinations thereof in the subject using a computer-implemented method for assessing mood, anxiety, and the like, and combinations thereof. In one aspect, the method is implemented using a computer device coupled to a memory device. The method implemented using a first computer device coupled to a memory device includes receiving mood information, anxiety information, and combinations thereof into the first computer device; storing, by the first computer device, the mood information, anxiety information, and combinations thereof in the memory device; presenting, by the first computer device, in visual form the mood information, anxiety information, and combinations thereof to a second computer device; receiving a request from the second computer device for access to the mood information, anxiety information, and combinations thereof; and transmitting, by the first computer device, the mood information, anxiety information, and combinations thereof to the second computer device to assess mood, anxiety, and combinations thereof in the subject.

Mood information includes information relating to a subject's mood, motivation, movement, thinking, self-esteem, interest, appetite, and combinations thereof. Anxiety information includes information relating to a subjects anxiety, uncertainty, fear, anger, and combinations thereof. Particular mood and anxiety information assessed can include: determining how good is the subject's mood; determining the subject's motivation, drive, determination to do things right now; determining how high is the subject's physical energy and the amount of moving about that the subject feels like doing right now; determining how high is the subject's mental energy and thinking activity going on in the subject's mind right now; determining how good the subject feels about himself/herself and his/her accomplishments right now; determining how high the subject's interest to do things that are fun and enjoyable right now; determining how high the subjects appetite and desire for food is right now; determining how anxious the subject is right now; determining how uncertain about things the subject is right now; determining how frightened about things the subject feels right now; determining how angry about things the subject feels right now; determining events or actions the subject thinks are influencing how the subject feels right now; determining additional feelings the subject has right now; and combinations thereof. As illustrated in FIGS. 6A-6C, the mood and anxiety information can be assessed by having the subject rate each piece of information on a scale of lowest to highest.

The subject of the method can further be diagnosed as having a psychiatric disorder selected from bipolar disorder, major depressive disorder, schizophrenia, and schizoaffective disorder, post-traumatic stress disorder, and combinations thereof.

In another aspect, the present disclosure is directed to a computer-implemented method for assessing socio-demographic/psychological suicidal risk factors in the subject using a computer-implemented method for assessing socio-demographic/psychological suicidal risk factors in the subject, the method implemented using a computer device coupled to a memory device. The method includes: receiving socio-demographic/psychological suicidal risk factor information into the first computer device; storing, by the first computer device, the socio-demographic/psychological suicidal risk factor information in the memory device; presenting, by the first computer device, in visual form the socio-demographic/psychological suicidal risk factor information to a second computer device; receiving a request from the second computer device for access to socio-demographic/psychological suicidal risk factor information; and transmitting, by the first computer device, the socio-demographic/psychological suicidal risk factor information to the second computer device to assess the socio-demographic/psychological suicidal risk factors in the subject.

Socio-demographic and clinical risk factors for suicide includes items for assessing the influence of mental health factors, as well as of life satisfaction, physical health, environmental stress, addictions, cultural factors known to influence suicidal behavior, and two demographic factors, age and gender. Socio-demographic/psychological suicidal risk factors assessed can include: lack of coping skills when faced with stress; dissatisfaction with current life; lack of hope for the future; current substance abuse; acute loss/grief; psychiatric illness diagnosed and treated; poor treatment compliance; family history of suicide in blood relatives; personally knowing somebody who committed suicide; history of abuse (such as physical abuse, sexual abuse, emotional abuse, and neglect); acute/severe medical illness (including acute pain); chronic stress (including perceived uselessness, not feeling needed, and burden to extended kin); history of excessive introversion/conscientiousness (including planned suicide attempts); past history of suicidal acts/gestures; lack of religious beliefs; rejection; lack of positive relationships/social isolation; history of excessive extroversion and impulsive behavior (including rage, anger, physical fights and seeking revenge); lack of children/not in touch with children/not helping care for children; history of command hallucinations of self-directed violence; age (older than 60 years or younger than 25 years); gender; and combinations thereof.

The socio-demographic/psychological suicidal risk factors can be assessed by having the subject provide an answer to the above factors such as a yes answer, a no answer and a not applicable answer.

The subject of the method can further be diagnosed as having a psychiatric disorder selected from bipolar disorder, major depressive disorder, schizophrenia, and schizoaffective disorder, post-traumatic stress disorder, and combinations thereof.

In another aspect, the present disclosure is directed to a method for predicting suicidality in a subject. The method includes: identifying a difference in the expression level of a blood biomarker in a sample obtained from a subject and a reference expression level of the blood biomarker by obtaining the expression level of the blood biomarker in a sample obtained from a subject; obtaining a reference expression level of a blood biomarker; analyzing the blood biomarker in the sample obtained from the subject and the reference expression level of the blood biomarker to detect the difference between the blood biomarker in the sample and the reference expression level of the blood biomarker; assessing mood, anxiety, and combinations thereof, using a first computer device coupled to a memory device, wherein the first computer device receives mood information, anxiety information, and combinations thereof into the first computer device; storing, by the first computer device, the mood information, anxiety information, and combinations thereof in the memory device; presenting, by the first computer device, in visual form the mood information, anxiety information, and combinations thereof to a second computer device; receiving a request from the second computer device for access to the mood information, anxiety information, and combinations thereof; and transmitting, by the first computer device, the mood information, anxiety information, and combinations thereof to the second computer device to assess mood, anxiety, and combinations thereof in the subject; assessing socio-demographic/psychological suicidal risk factors in the subject using the first computer device coupled to a memory device, wherein the first computer device receives socio-demographic/psychological suicidal risk factor information into the first computer device; storing, by the first computer device, the socio-demographic/psychological suicidal risk factor information in the memory device; presenting, by the first computer device, in visual form the socio-demographic/psychological suicidal risk factor information to the second computer device; receiving a request from the second computer device for access to socio-demographic/psychological suicidal risk factor information; and transmitting, by the first computer device, the socio-demographic/psychological suicidal risk factor information to the second computer device to assess the socio-demographic/psychological suicidal risk factors in the subject; and predicting suicidality in the subject by the combination of the difference between the expression level of the biomarker in the subject and the reference expression level of the blood biomarker; the assessment of mood, anxiety, and combinations thereof; and the assessment of socio-demographic/psychological suicidal risk factor information.

As used herein, while the methods are described as using a first and second computer device, it should be understood that more or less than two computer devices may be used to perform the methods of the present disclosure. Particularly, three computer devices, or four computer devices or even five or more computer devices can be used to perform the methods without departing from the scope of the present disclosure.

In one aspect, the present disclosure is directed to a method for predicting future hospitalization of a subject due to suicidality. The method includes: identifying a difference in the expression level of a blood biomarker in a sample obtained from a subject and a reference expression level of the blood biomarker by obtaining the expression level of the blood biomarker in a sample obtained from a subject; obtaining a reference expression level of a blood biomarker; analyzing the blood biomarker in the sample obtained from the subject and the reference expression level of the blood biomarker to detect the difference between the blood biomarker in the sample and the reference expression level of the blood biomarker; assessing mood, anxiety, and combinations thereof, using a first computer device coupled to a memory device, wherein the first computer device receives mood information, anxiety information, and combinations thereof into the first computer device; storing, by the first computer device, the mood information, anxiety information, and combinations thereof in the memory device; presenting, by the first computer device, in visual form the mood information, anxiety information, and combinations thereof to a second computer device; receiving a request from the second computer device for access to the mood information, anxiety information, and combinations thereof; and transmitting, by the first computer device, the mood information, anxiety information, and combinations thereof to the second computer device to assess mood, anxiety, and combinations thereof in the subject; assessing socio-demographic/psychological suicidal risk factors in the subject using the first computer device coupled to a memory device, wherein the first computer device receives socio-demographic/psychological suicidal risk factor information into the first computer device; storing, by the first computer device, the socio-demographic/psychological suicidal risk factor information in the memory device; presenting, by the first computer device, in visual form the socio-demographic/psychological suicidal risk factor information to a second computer device; receiving a request from the second computer device for access to socio-demographic/psychological suicidal risk factor information; and transmitting, by the first computer device, the socio-demographic/psychological suicidal risk factor information to the second computer device to assess the socio-demographic/psychological suicidal risk factors in the subject; and predicting future hospitalization of the subject due to suicidality by the combination of the difference between the expression level of the biomarker in the subject and the reference expression level of the blood biomarker; the assessment of mood, anxiety, and combinations thereof; and the assessment of socio-demographic/psychological suicidal risk factor information.

Suitable biomarkers for use in the method for predicting suicide ideation in a subject and the method for predicting future hospitalization a subject due to suicidality include those described herein.

Mood information for use in the method for predicting suicide ideation in a subject and the method for predicting future hospitalization of a subject due to suicidality includes information relating to a subject's mood, motivation, movement, thinking, self-esteem, interest, appetite, and combinations thereof as described herein. Anxiety information includes information relating to a subjects anxiety, uncertainty, fear, anger, and combinations thereof as described herein.

Socio-demographic and clinical risk factors for suicide for use in the method for predicting suicide ideation in a subject and the method for predicting future hospitalization of a subject due to suicidality include items for assessing the influence of mental health factors, as well as of life satisfaction, physical health, environmental stress, addictions, cultural factors known to influence suicidal behavior, and two demographic factors, age and gender as described herein.

EXAMPLES

Methods

Human Blood Gene Expression Experiments and Analyses

RNA Extraction.

Whole blood (2.5-5 ml) was collected into each PaxGene tube by routine venipuncture. PaxGene tubes contain proprietary reagents for the stabilization of RNA. RNA was extracted and processed.

Microarrays.

Biotin-labeled aRNAs were hybridized to Affymetrix HG-U133 Plus 2.0 GeneChips (Affymetrix; with over 40 000 genes and expressed sequence tags), according to the manufacturer's protocols. Arrays were stained using standard Affymetrix protocols for antibody signal amplification and scanned on an Affymetrix GeneArray 2500 scanner with a target intensity set at 250. Quality-control measures, including 30/50 ratios for glyceraldehyde 3-phosphate dehydrogenase and β-actin, scale factors, background and Q-values, were within acceptable limits.

Analysis.

Figure 1C:
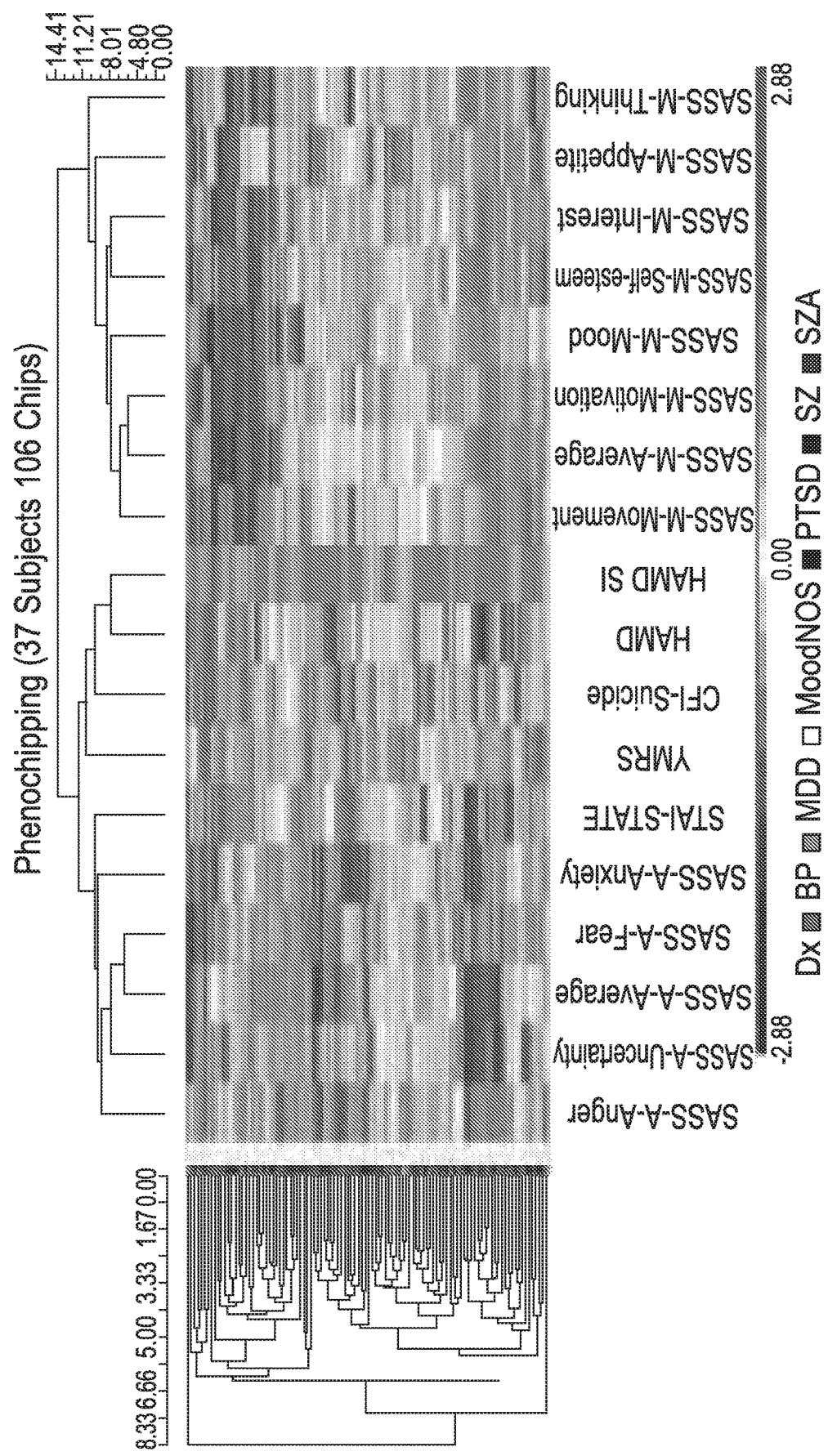
Figures 10A, 10B:
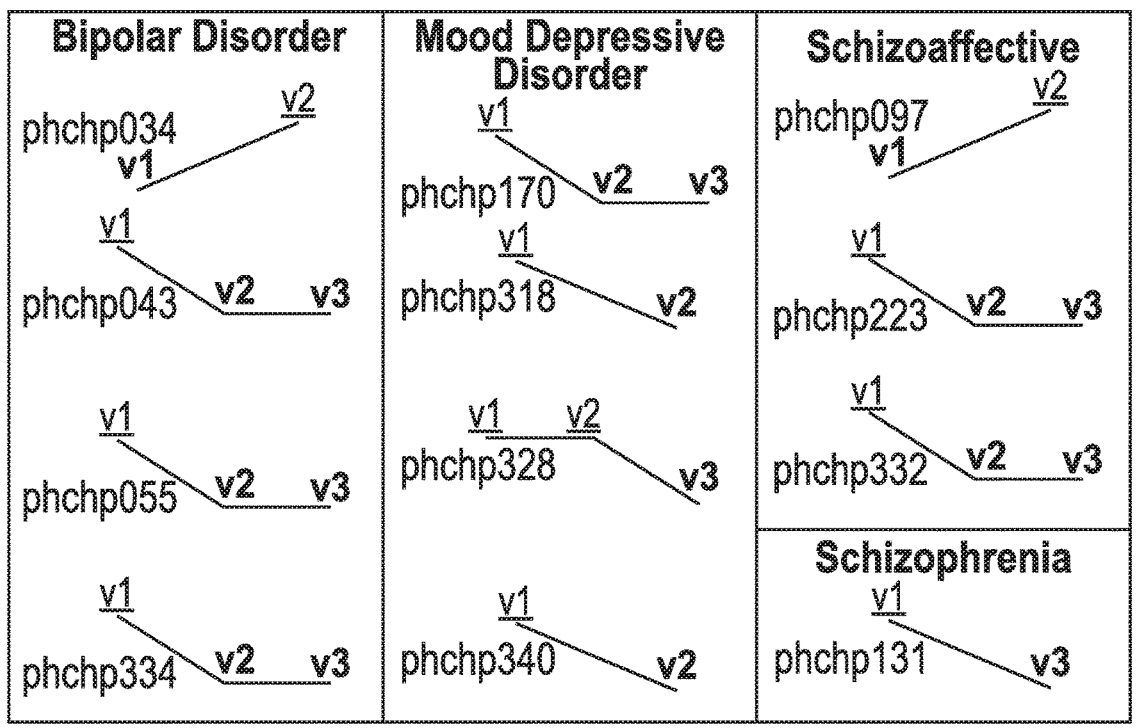
FIGS. 10A-10C depict biomarker discovery as analyzed in Example 2. Discovery cohort: longitudinal within-participant analysis. Phchp ### is study ID for each participant. V #denotes visit number (1, 2, 3, 4, 5, or 6).
Figure 10C:
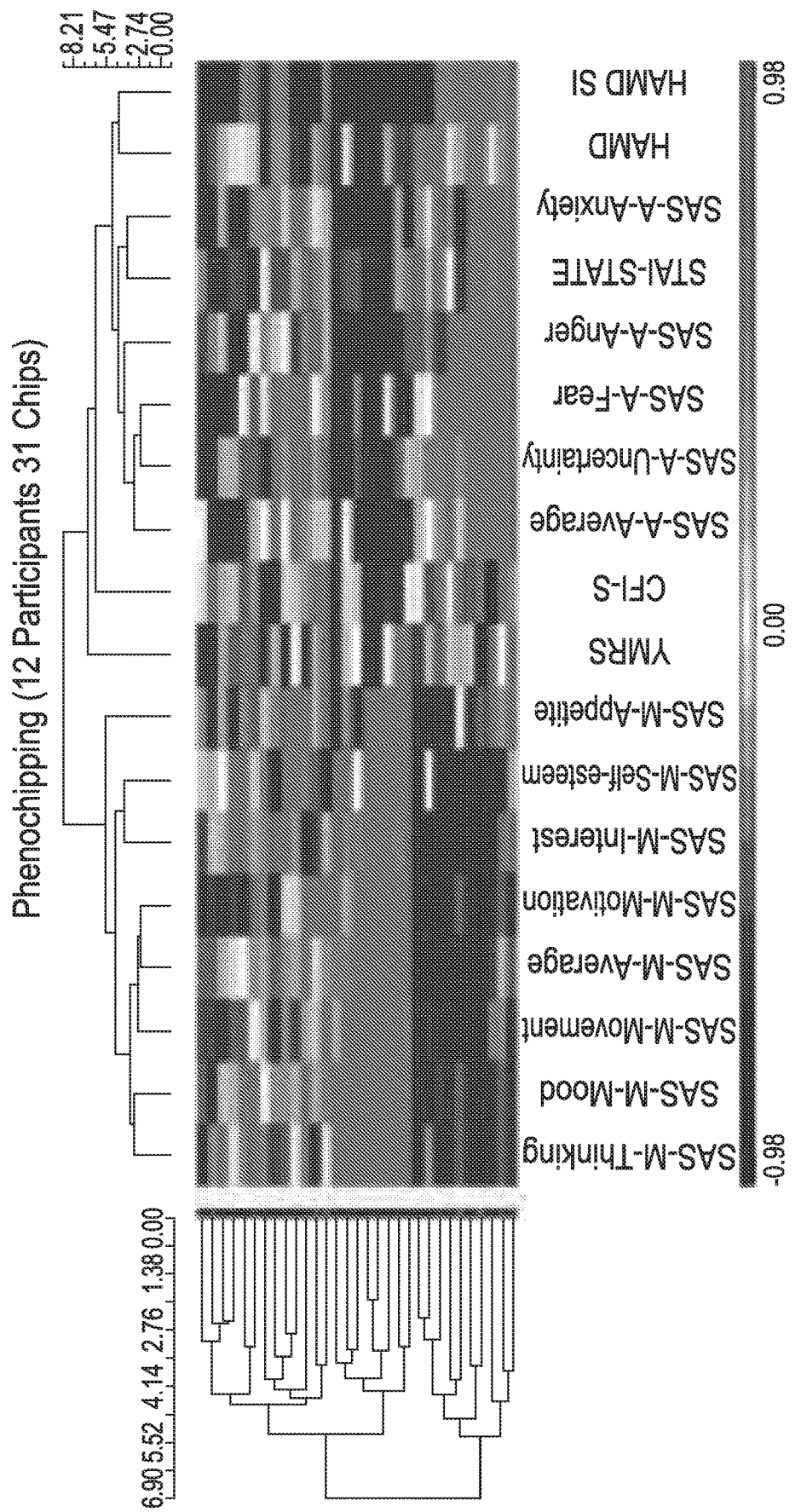

The participant's SI scores at the time of blood collection (0—no suicidal ideation (SI) compared with 2 and above—high SI) were used. Gene expression differences between the no SI and the high SI visits were analyzed using a within-participant design, then an across-participants summation (FIGS. 1C and 10C).

Gene Expression Analysis in the Discovery Cohort

Data was analyzed in two ways: an Absent-Present (AP) approach and a differential expression (DE) approach. The AP approach may capture turning on and off of genes, and the DE approach may capture gradual changes in expression. For the AP approach, Affymetrix Microarray Suite Version 5.0 (MAS5) was used to generate Absent (A), Marginal (M), or Present (P) calls for each probe set on the chip (Affymetrix U133 Plus 2.0 GeneChips) for all participants in the discovery cohort. For the DE approach, all Affymetrix microarray data was imported as Cel. files into Partek Genomic Suites 6.6 software package (Partek Incorporated, St Louis, Mo., USA). Using only the perfect match values, a robust multi-array analysis (RMA) was run, background corrected with quantile normalization and a median polish probe set summarization, to obtain the normalized expression levels of all probe sets for each chip. RMA was performed independently for each of the 6 diagnoses used in the study, to avoid potential artefacts due to different ranges of gene expression in different diagnoses (Niculescu et al. MP 2015). Then the participants' normalized data was extracted from these RMA and assembled for the different cohorts used in the Example.

A/P analysis.

For the longitudinal within participant AP analysis, comparisons were made within participant between sequential visits to identify changes in gene expression from Absent to Present that track changes in phene expression (suicidal ideation, "SI") from No SI to High SI. For a comparison, if there was a change from A to P tracking a change from No SI to High SI, or a change from P to A tracking a change from High SI to No SI, that was given a score of +1 (increased biomarker in High SI). If the change was in opposite direction in the gene vs the phene (SI), that was given a score of −1 (decreased biomarker in High SI). If there was no change in gene expression between visits, despite a change of phene expression (suicidal ideation), or a change in gene expression between visits, despite no change in phene expression (suicidal ideation), that was given a score of 0 (not tracking as a biomarker). If there was no change in gene expression and no change in suicidal ideation between visits, that was given a score of +1 if there was concordance (P-P with High SI-High SI, or A-A with No SI-No SI), or a score of −1 if there was the opposite (A-A with High SI-High SI, or P-P with No SI-No SI). If the changes were to M (moderate) instead of P, the values used were 0.5 or −0.5. These values were then summed up across the comparisons in each participant, resulting in a participant score for each gene/probeset in each participant. A perfection bonus was also used. If the gene expression perfectly tracked the suicidal ideation in a participant that had at least two comparisons (3 visits), that probe set was rewarded by a doubling of its participant score. Additionally, a non-tracking correction was used. If there was no change in gene expression in any of the comparisons for a particular participant, that overall participant score for that probe set in that participant was zero.

DE Analysis.

For the longitudinal within participant DE analysis, fold changes (FC) in gene expression were calculated between sequential visits within each participant. Scoring methodology was similar to that used above for AP. Probe sets that had a FC≥1.2 were scored+1 (increased in High SI) or −1 (decreased in High SI). FC≥1.1 were scored+0.5 or −0.5. FC lower than 1.1 were considered no change. The only difference between the DE and the AP analyses was when scoring comparisons where there was no phene expression (SI) change between visits and no change in gene expression between visits (FC lower than 1.1). In that case, the comparison received the same score as the nearest preceding comparison where there was a change in SI from visit to visit. If no preceding comparison with a change in SI was available, then it was given the same score as the nearest subsequent comparison where there was a change in SI. Also for DE, a perfection bonus and a non-tracking correction was used. If the gene expression perfectly tracked the suicidal ideation in a participant who had at least two comparisons (3 visits), that probe set was rewarded by a doubling of its score. If there was no change in gene expression in any of the comparisons for a particular participant, that overall participant score for that probe set in that participant was zero.

Internal Score.

Once scores within each participant were calculated, an algebraic sum across all participants was obtained for each probe set. Probe sets were then given internal CFG points based upon these algebraic sum scores. Probe sets with scores above the 33% of the distribution (for increased probe sets and decreased probe sets) received 1 point, those above 50% of the distribution received 2 points, and those above 80% of the distribution received 4 points.

Figure 2A:
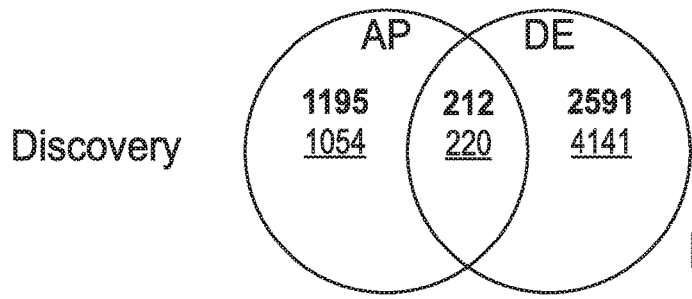
FIGS. 2A-2D depict the Biomarker Discovery, Prioritization and Validation of Example 1.
Figure 11A:
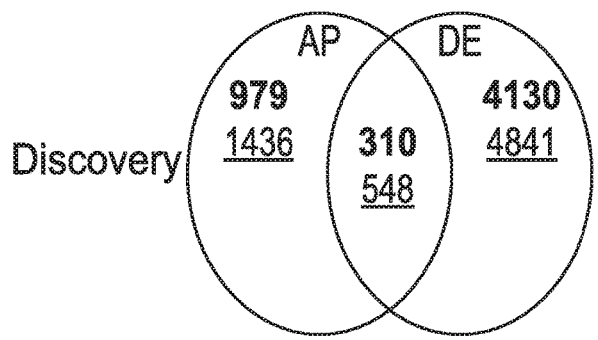
FIGS. 11A-11C depict biomarker prioritization and validation as analyzed in Example 2.

In Example 1, for AP analyses, 23 probe sets received 4 points, 581 probe sets received 2 points, and 2077 probe sets received 1 point, for a total of 2681 probe sets. For DE analyses, 31 probe sets received 4 points, 1294 probe sets received 2 points, and 5839 probe sets received 1 point, for a total of 7164 probe sets. The overlap between the two discovery methods is shown in FIG. 2A. For Example 2, for AP analyses, 30 probesets received 4 points, 647 probesets with 2 points, and 2596 probesets with 1 point, for a total of 3273 probesets. For DE analyses, 95 probesets received 4 points, 2215 probesets with 2 points, and 7520 probesets with 1 point, for a total of 9829 probesets. The overlap between the two discovery methods for probesets with an internal score of 1 is shown in FIG. 11A.

Different probe sets may be found by the two methods due to differences in scope (DE capturing genes that were present in both visits of a comparison (i.e. PP, but are changed in expression), thresholds (what makes the 33% change cutoff across participants varies between methods), and technical detection levels (what is considered in the noise range varies between the methods).

Figure 2B:
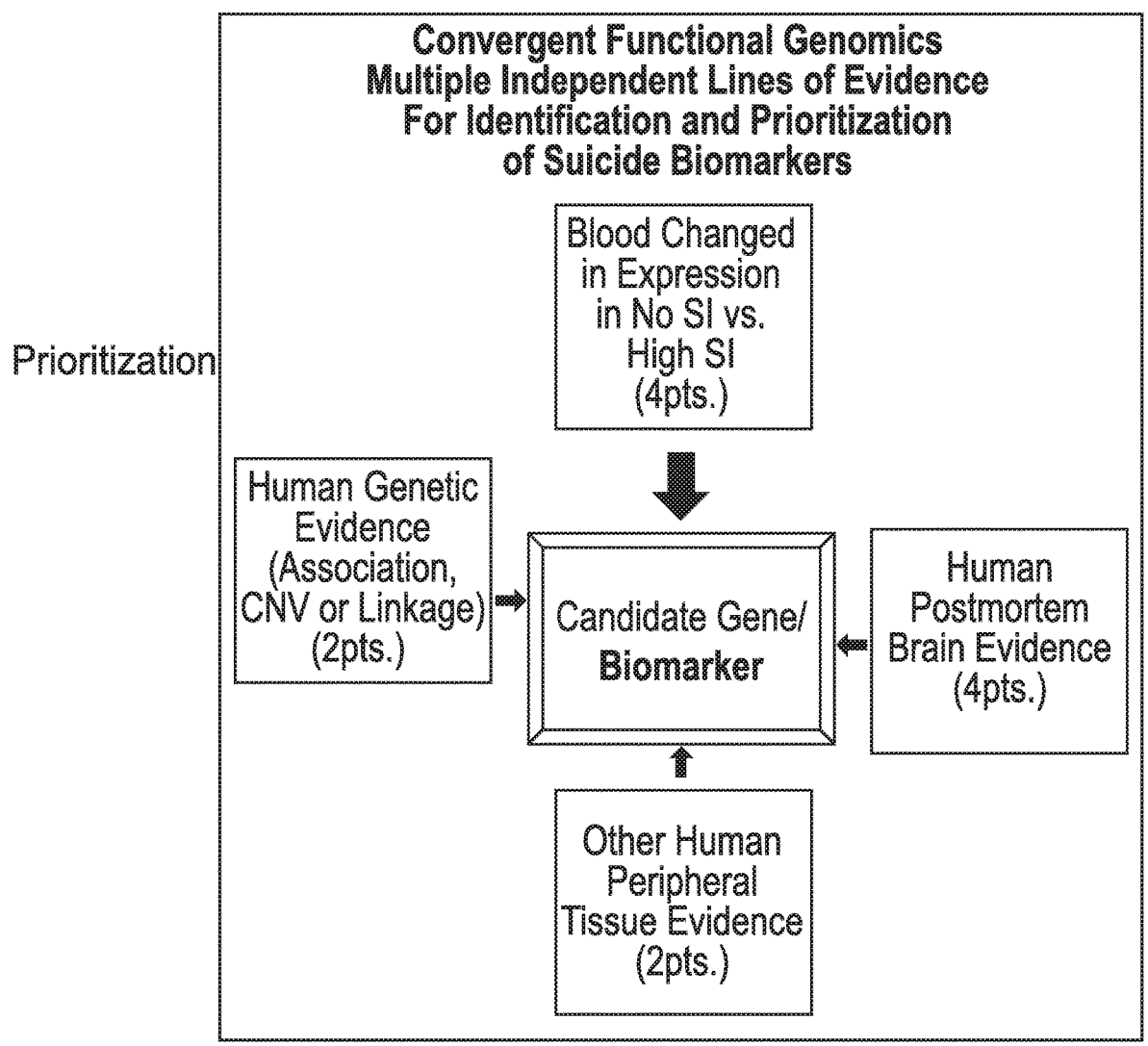
Figure 2C:
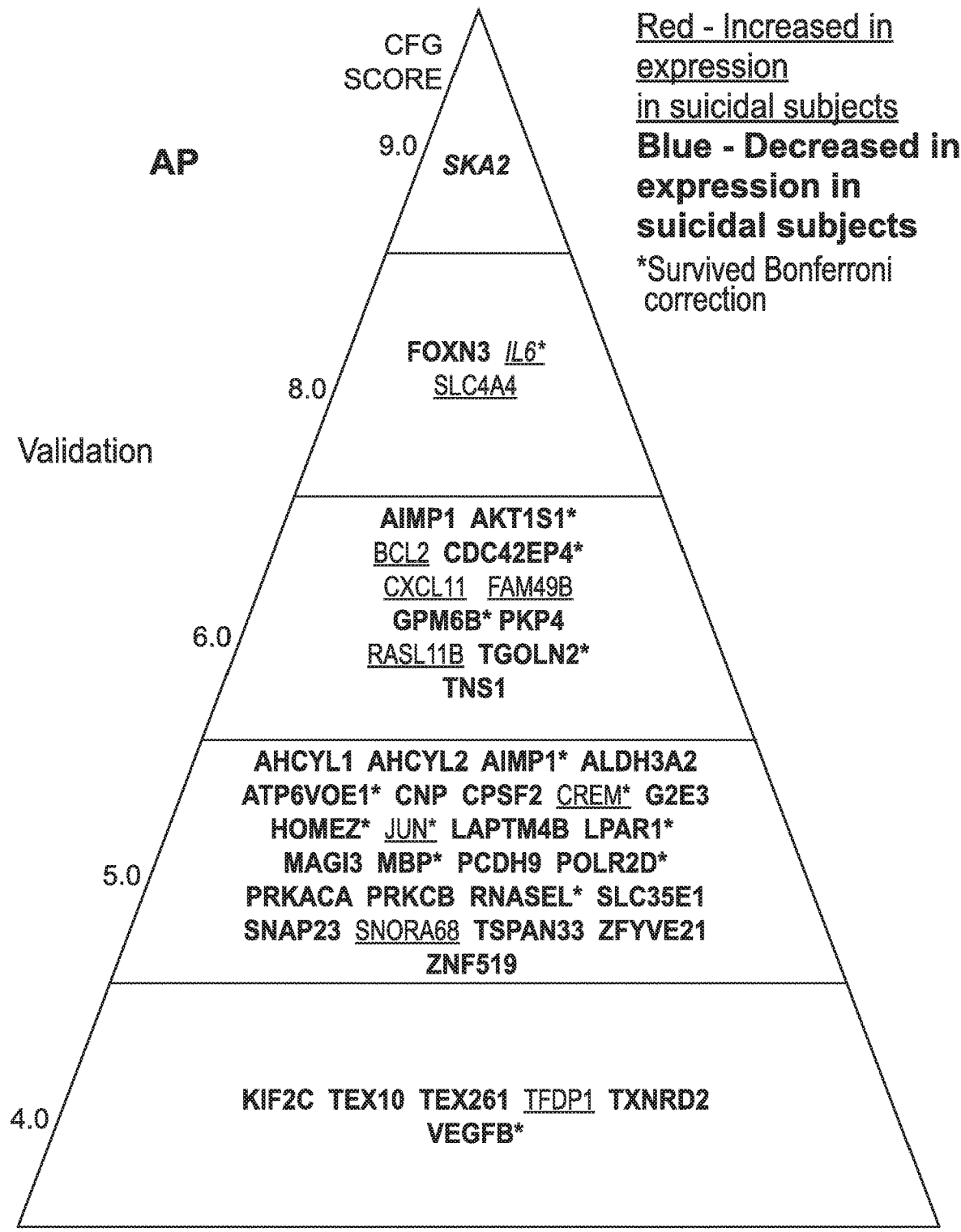
Figure 2D:
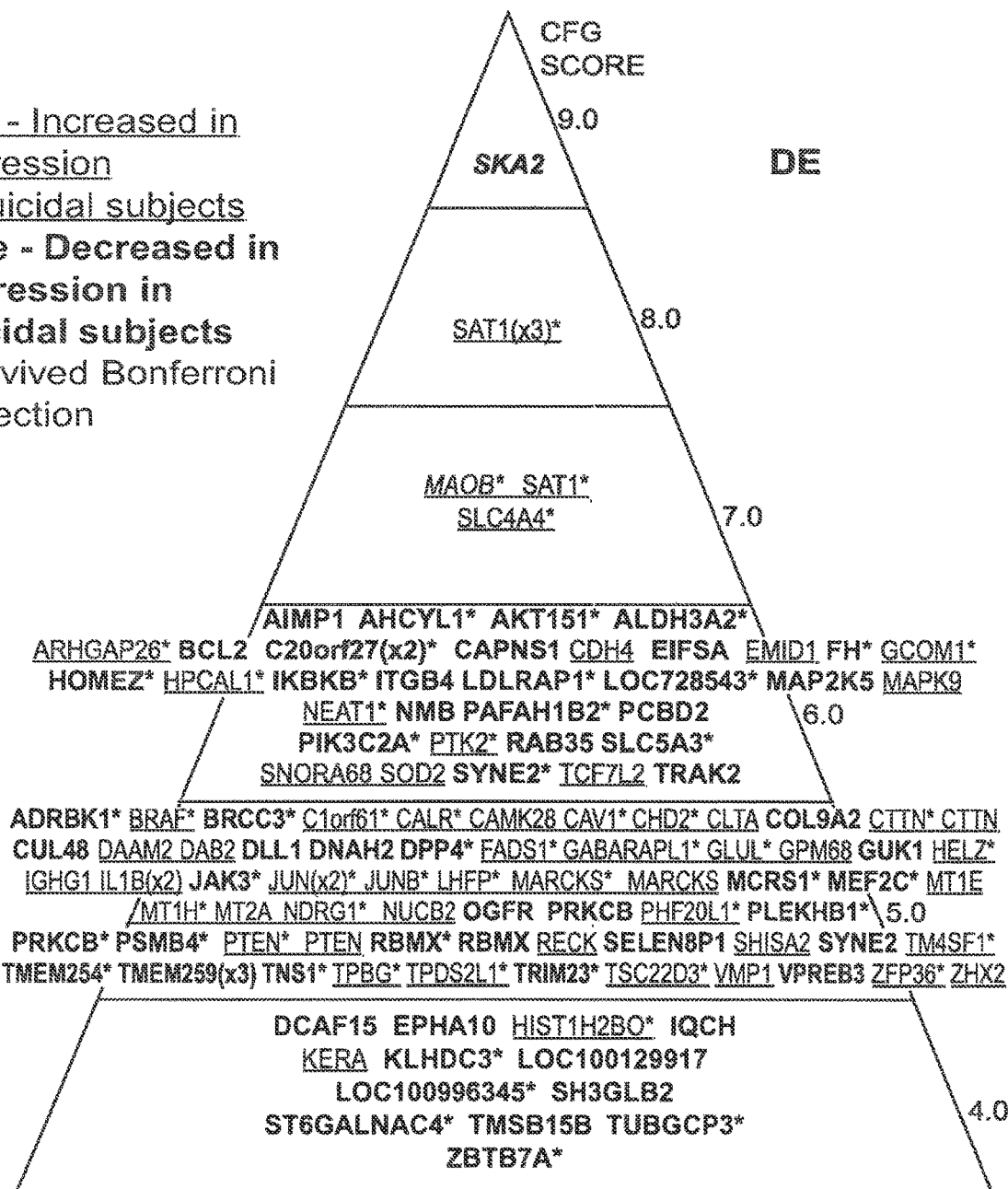
Figure 11B:
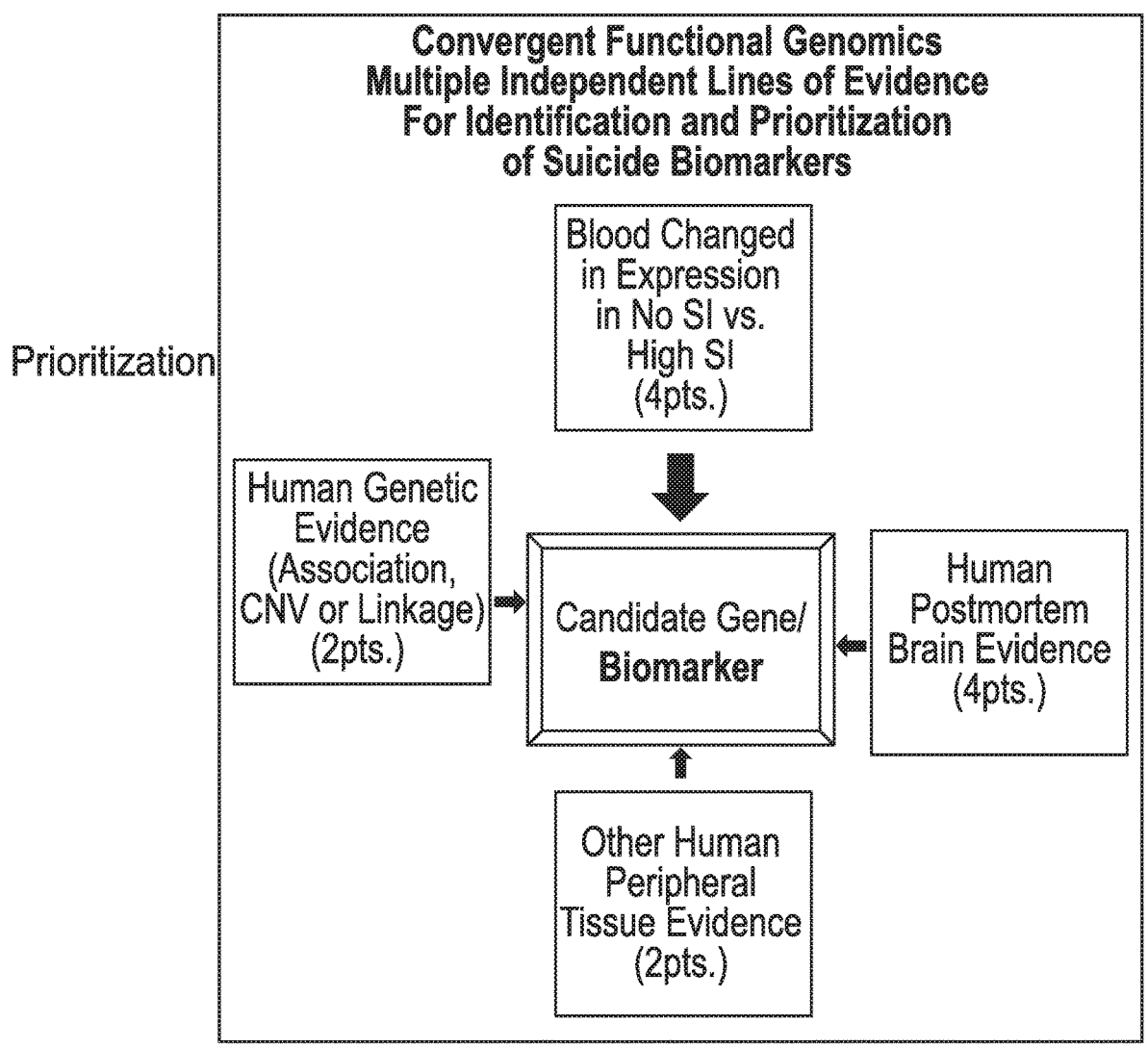
Figure 11C:
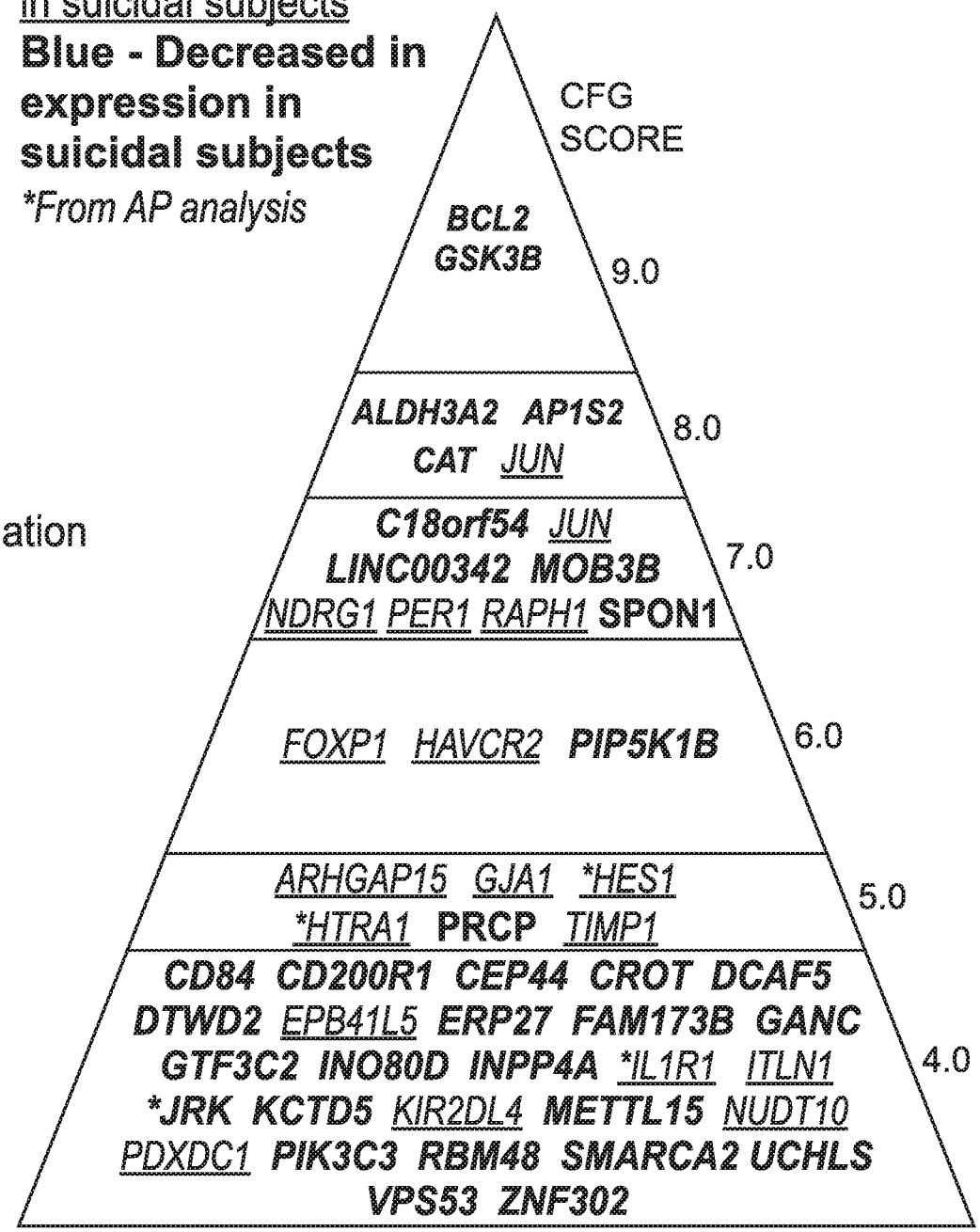

In total, 9413 probe sets were identified with an internal CFG score of 1. Gene names for the probe sets were identified using NetAffyx (Affymetrix) and Partek for Affymetrix HG-U133 Plus 2.0 GeneChips, followed by GeneCards to confirm the primary gene symbol. In addition, for those probe sets that were not assigned a gene name by NetAffyx or Partek, the UCSC Genome Browser was used to directly map them to known genes, with the following limitations. In case the probe set fell in an intron, that particular gene was assumed to be implicated. Only one gene was assigned to each probe set. Genes were then scored using manually curated CFG databases as described below (FIGS. 2C and 11C).

Convergent Functional Genomics Databases.

Manually curated databases of all the human gene expression (postmortem brain, blood and cell cultures), human genetics (association, copy number variations and linkage), and animal model gene expression and genetic studies published to date on psychiatric disorders was established (Laboratory of Neurophenomics, Indiana University School of Medicine, www.neurophenomics.info). The databases include only primary literature data and do not include review papers or other secondary data integration analyses to avoid redundancy and circularity. These large and constantly updated databases have been used for CFG cross validation and prioritization (FIGS. 2B, 2C, 11B and 11C). For Example 2, data from 442 papers on suicide were present in the databases at the time of the CFG analyses (genetic studies—164, brain studies—192, peripheral fluids—86).

Human Postmortem Brain Gene Expression Evidence.

Converging evidence was scored for a gene if there were published reports of human postmortem data showing changes in expression of that gene or changes in protein levels in brains from participants who died from suicide.

Human Blood and Other Peripheral Tissue Gene Expression Data.

Converging evidence was scored for a gene if there were published reports of human blood, lymphoblastoid cell lines, CSF, or other peripheral tissue data showing changes in expression of that gene or changes in protein levels in participants who had a history of suicidality or who died from suicide.

Human Genetic Evidence (Association and Linkage).

To designate convergence for a particular gene, the gene had to have independent published evidence of association or linkage for suicide. For linkage, the location of each gene was obtained through GeneCards (http://www.genecards.org), and the sex averaged cM location of the start of the gene was then obtained through http://compgen.rutgers.edu/mapinterpolator. For linkage convergence, the start of the gene had to map within 5 cM of the location of a marker linked to the disorder.

CFG Scoring.

For CFG analysis (FIGS. 2C and 11C), the external cross-validating lines of evidence were weighted such that findings in human postmortem brain tissue, the target organ, were prioritized over peripheral tissue findings and genetic findings, by giving them twice as many points. Human brain expression evidence was given 4 points, whereas human peripheral evidence was given 2 points, and human genetic evidence was given a maximum of 2 points for association and 1 point for linkage. Each line of evidence was capped in such a way that any positive findings within that line of evidence resulted in maximum points, regardless of how many different studies support that single line of evidence, to avoid potential popularity biases. In addition to the external CFG score, genes were also prioritized based upon the initial gene expression analyses used to identify them. Probe sets identified by gene expression analyses could receive a maximum of 4 points. Thus, the maximum possible total CFG score for each gene was 12 points (4 points for the internal CFG score and 8 points for the external CFG score). The scoring system was decided upon before the analyses were carried out. Twice as much weight was given to external CFG than to internal CFG in order to increase generalizability and avoid fit to cohort of the prioritized genes. It is recognized that other ways of scoring the lines of evidence may give slightly different results in terms of prioritization, if not in terms of the list of genes per se. Nevertheless, it is believed that this simple scoring system provides a good separation of genes based on gene expression evidence and on independent cross-validating evidence in the field (FIGS. 2B and 11B).

Pathway Analyses

Figure 15:
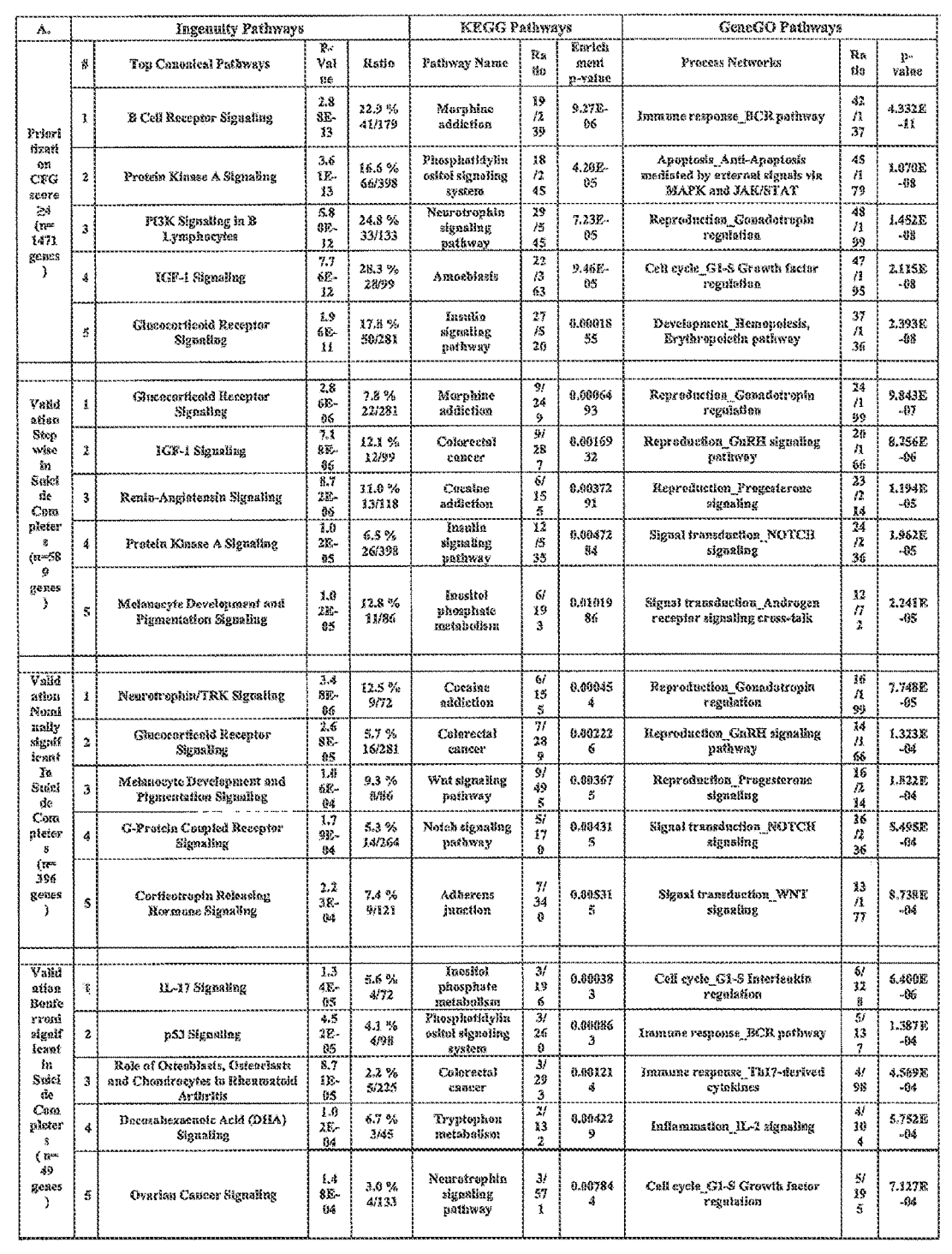
Figure 17A:
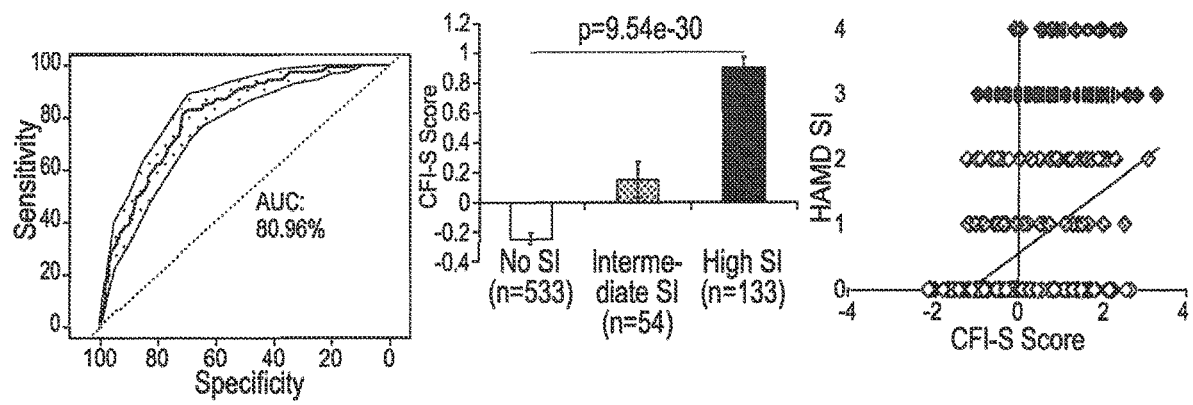
Figure 18A:
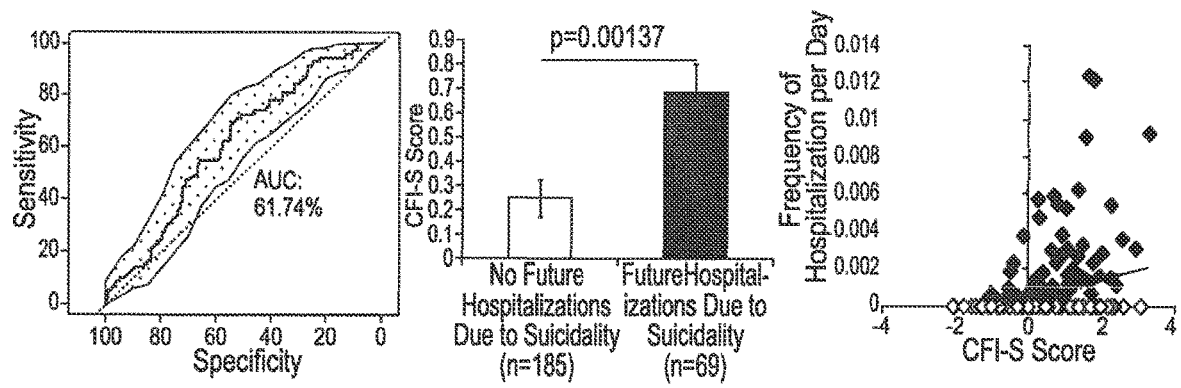

IPA 9.0 (Ingenuity Systems, Redwood City, Calif., USA), GeneGO MetaCore (Encinitas, Calif.), and Kyoto Encyclopedia of Genes and Genomes (through the Partek Genomics Suite 6.6 software package) were used to analyze the biological roles, including top canonical pathways, and diseases, of the candidate genes resulting from this work, as well as to identify genes in the dataset that are the target of existing drugs (FIGS. 8, 15 and 17). The analyses was run together for all the AP and DE probe sets with a total CFG score≥4, then for those of them that showed stepwise change in the suicide completers validation cohort, then for those of them that were nominally significant, and finally for those of them that survived Bonferroni correction.

Validation Analyses

For validation of the candidate biomarker genes, which of the top candidate genes (CFG score of 4 or above) that were stepwise changed in expression from the No SI group to the High SI group to the suicide completers group, were examined. The empirical cutoff of 33% of the maximum possible CFG score of 12 was used, which also permits the inclusion of potentially novel genes with maximal internal CFG score, but no external CFG score. Statistical analyses were performed in SPSS using one-way ANOVA and Bonferonni corrections.

For the AP analyses, the Affymetrix microarray data files were imported from the participants in the validation cohort of suicide completers into MASS, alongside the data files from the participants in the discovery cohort.

For the DE analyses, Cel. files were imported into Partek Genomic Suites. A RMA was then run, background corrected with quantile normalization, and a median polish probe set summarization of all the chips from the validation cohort to obtain the normalized expression levels of all probe sets for each chip. Partek normalizes expression data into a log base of 2 for visualization purposes. Expression data was non-log-transformed by taking 2 to the power of the transformed expression value. The non-log-transformed expression data was then used to compare expression levels of biomarkers in the different groups.

Testing Analyses

The test cohort for suicidal ideation and the test cohort for future hospitalizations analyses were assembled out of data that was RMA normalized by diagnosis. Phenomic (clinical) and gene expression markers used for predictions were z-scored by diagnosis, to be able to combine different markers into panels and to avoid potential artefacts due to different ranges of phene expression and gene expression in different diagnoses. Markers were combined by computing the average of the increased risk markers minus the average of the decreased risk markers. Predictions were performed using R-studio.

Predicting Suicidal Ideation.

Receiver-operating characteristic (ROC) analyses between marker levels and suicidal ideation (SI) were performed by assigning participants with a HAMD SI score of 0-1 into the no SI category, and participants with a HAMD-SI score of 2 and greater into the SI category. Additionally, ANOVA was performed between no (HAMD-SI 0), moderate (HAMD-SI 1), and high SI participants (HAMD-SI 2 and above) and Pearson R (one-tail) was calculated between HAMD-SI scores and marker levels.

Predicting Future Hospitalizations for Suicidality.

Analyses for hospitalizations in the first year following testing were conducted on data for all the participants for which data was collected. For each participant in the test cohort for future hospitalizations, the Example visit with highest levels for the marker or combination of markers was selected as index visit (or with the lowest levels, in the case of decreased markers). ROC analyses between marker levels and future hospitalizations were performed based on assigning if participants had been hospitalized for suicidality (suicide ideation, suicide attempts) or not following the index testing visit. Additionally, a one tailed t-test with unequal variance was performed between groups of participants with and without hospitalizations for suicidality. Pearson R (one-tail) correlation was performed between hospitalization frequency (number of hospitalizations for suicidality divided by duration of follow-up) and biomarker score. The correlation analysis for hospitalizations frequency was also conducted for all future hospitalizations due to suicide beyond one year, as this calculation, unlike the ROC and t-test, accounts for the actual length of follow-up, which varied beyond one year from participant to participant.

Example 1

In this Example, male subjects were analyzed for predicting suicidal ideation and future hospitalizations for suicidality.

Human Participants

Data was obtained from four cohorts: one live psychiatric participants discovery cohort (within-participant changes in suicidal ideation; n=37 out of 217); one postmortem coroner's office validation cohort (suicide completers; n=26); and two live psychiatric participants test cohorts—one for predicting suicidal ideation (n=108) and one for predicting future hospitalizations for suicidality (n=157).

Live psychiatric participants were recruited from the patient population at the Indianapolis VA Medical Center. All participants understood and signed informed consent forms detailing the research goals, procedure, caveats and safeguards. Participants completed diagnostic assessments by an extensive structured clinical interview—Diagnostic Interview for Genetic Studies—at a baseline visit, followed by up to six testing visits, 3-6 months apart or whenever a hospitalization occurred. At each testing visit, they received a series of psychiatric rating scales, including the Hamilton Rating Scale for Depression-17, which includes a suicidal ideation (SI) rating item (FIGS. 1A-1C), and blood was drawn. Whole blood (10 ml) was collected in two RNA-stabilizing PAXgene tubes, labeled with an anonymized ID number, and stored at −80 degrees C. in a locked freezer until the time of future processing. Whole-blood (predominantly lymphocyte) RNA was extracted for microarray gene expression studies from the PAXgene tubes, as detailed below. This Example focused on a male population because of the demographics of the catchment area (primarily male in a VA Medical Center), and to minimize any potential gender-related effects on gene expression, which would have decreased the discriminative power of the analysis given the relatively small sample size.

The within participant discovery cohort, from which the biomarker data were derived, consisted of 37 male participants with psychiatric disorders, with multiple visits, who each had at least one diametric change in SI scores from no SI to high SI from one testing visit to another testing visit. There was 1 participant with 6 visits, 1 participant with 5 visits, 1 participant with 4 visits, 23 participants with 3 visits each, and 11 participants with 2 visits each, resulting in a total of 106 blood samples for subsequent microarray studies (FIG. 1B).

The postmortem cohort, in which the top biomarker findings were validated, consisted of a demographically matched cohort of 24 male violent suicide completers obtained through the Marion County coroner's office (FIG. 9). A last observed alive postmortem interval of 24 hours or less was required, and the cases selected had completed suicide by means other than overdose, which could affect gene expression. 14 participants completed suicide by gunshot to head or chest, 8 by hanging, 1 by electrocution and 1 by slit wrist. Next of kin signed informed consent at the coroner's office for donation of tissues and fluids for research. The samples were collected as part of the INBRAIN initiative (Indiana Center for Biomarker Research in Neuropsychiatry).

The independent test cohort for predicting suicidal ideation consisted of 108 male participants with psychiatric disorders, demographically matched with the discovery cohort with one or multiple testing visits in the lab, with either no SI, intermediate SI, or high SI, resulting in a total of 223 blood samples in whom whole-genome blood gene expression data were obtained.

The test cohort for predicting future hospitalizations consisted of male participants in whom whole-genome blood gene expression data were obtained at testing visits over the years as part of a longitudinal study. If the participants had multiple testing visits, the visit with the highest marker (or combination of markers) levels was selected for the analyses. The participants' subsequent number of psychiatric hospitalizations, with or without suicidality, was tabulated from electronic medical records. All participants had at least one year of follow-up or more at the VA Medical Center since the time of the testing visits in the lab. Participants were evaluated for the presence of future hospitalizations for suicidality, and for the frequency of such hospitalizations. A hospitalization was deemed to be without suicidality if suicidality was not listed as a reason for admission, and no SI was described in the admission and discharge medical notes. Conversely, a hospitalization was deemed to be because of suicidality if suicidal acts or intent was listed as a reason for admission, and SI was described in the admission and discharge medical notes.

Medications

The participants in the discovery cohort were all diagnosed with various psychiatric disorders (e.g., BP, MDD, SZA, SZ, PTSD). The participants were on a variety of different psychiatric medications: mood stabilizer, antidepressants, antipsychotics, benzodiazepines and others. Medications can have a strong influence on gene expression. However, the identification of differentially expressed genes was based on within-participant analyses, which factor out not only genetic background effects but also medication effects, as the participants had no major medication changes between visits. Moreover, there was no consistent pattern in any particular type of medication, or between any change in medications and SI, in the rare instances where there were changes in medications between visits.

Results

The top increased and decreased biomarkers after the discovery for ideation (CADM1, CLIP4, DTNA, KIF2C), prioritization with CFG for prior evidence (SAT1, SKA2, SLC4A4), and validation for behavior in suicide completers (IL6, MBP, JUN, KLHDC3) steps were tested in a completely independent test cohort of psychiatric participants for prediction of suicidal ideation (n=108), and in a future follow-up cohort of psychiatric participants (n=157) for prediction of psychiatric hospitalizations due to suicidality. The best individual biomarker across psychiatric diagnoses for predicting suicidal ideation was SLC4A4, with 72% accuracy. For bipolar disorder in particular, SLC4A4 predicted suicidal ideation with 93% accuracy, and future hospitalizations with 70% accuracy. Two new clinical information apps, one for affective state (Simplified Affective Scale, SASS) and one for suicide risk factors (Convergent Functional Information for Suicide, CFI-S) are disclosed, and how well they predict suicidal ideation across psychiatric diagnoses (85% accuracy for SASS, 89% accuracy for CFI-S). Also disclosed is that the integration of the top biomarkers and the clinical information into a universal predictive measure (UP-Suicide) was able to predict suicidal ideation across psychiatric diagnoses with 92% accuracy. For bipolar disorder, it was able to predict suicidal ideation with 98% accuracy and future hospitalizations with 94% accuracy.

For discovery, two differential expression methodologies were used: Absent/Present (AP) (reflecting on/off of transcription) and Differential Expression (DE) (reflecting more subtle gradual changes in expression levels). Genes that tracked suicidal ideation in each participant were identified. Three thresholds were used for increased in expression genes and for decreased in expression genes: ≥33% (low), ≥50% (medium), and ≥80% (high) of the maximum scoring increased and decreased gene across participants. These differentially expressed genes were then prioritized using a Bayesian-like Convergent Functional Genomics (CFG) approach (FIGS. 2A-2C), integrating all the previously published human genetic evidence, postmortem brain gene expression evidence, and peripheral fluids evidence for suicide available in the field as of September 2014 to identify and prioritize disease relevant genomic biomarkers, extracting generalizable signal out of potential cohort-specific noise and genetic heterogeneity. For validation, genes whose levels of expression were changed stepwise significantly from no suicidal ideation to high suicidal ideation to suicide completion, and who survived Bonferroni correction for multiple comparisons, were carried forward. The overall best biomarkers for suicidal ideation across diagnostic groups was identified. The top genes after discovery were DTNA and KIF2C from AP, CADM1 and CLIP4 from DE. The top genes after prioritization with CFG were SLC4A4 and SKA2 from AP; and SAT1 and SKA2 from DE. The top genes after validation in suicide completers were IL6 and MBP from AP; and JUN and KLHDC3 from DE (FIGs. 2C-2C). Notably, the SAT1 finding is a replication and expansion of previously reported results identifying SAT1 as a biomarker for suicidality (Le-Niculescu et al. 2013), and the SKA2 finding is an independent replication of a previous report identifying SKA2 as a biomarker for suicidality (Kaminsky et al. 2014). A number of other genes identified are completely novel in terms of their involvement in suicidality.

To understand the biology represented by the biomarkers identified, and derive some mechanistic and practical insights, unbiased biological pathway analyses and hypothesis driven mechanistic queries, overall disease involvement and specific neuropsychiatric disorders queries, and overall drug modulation along with targeted queries for omega-3, lithium and clozapine were conducted. Administration of omega-3s in particular may be a mass-deployable therapeutic and preventive strategy.

The sets of biomarkers identified have biological roles in immune and inflammatory response, growth factor regulation, mTOR signaling, stress, and perhaps overall the switch between cell survival and proliferation vs. apoptosis (FIGS. 8A-8B). An extrapolation can be made and model proposed whereas suicide is a whole body apoptosis (or "self-poptosis") in response to perceived stressful life events.

Evidence for the involvement of the biomarkers for suicidality was also examined for involvement in other psychiatric disorders, allowing for analysis of context and specificity FIGS. 8 and 9). SKA2, HADHA, SNORA68, RASL11B, CXCL11, HOMEZ, LOC728543, AHCYL1, LDLRAP1, NEAT1 and PAFAH1B2 appeared to be relatively specific for suicide, based on the evidence to date. SAT1, IL6, FOXN3 and FKBP5 were less specific for suicide, having equally high evidence for involvement in suicide and in other psychiatric disorders, possibly mediating stress response as a common denominator. CADM1, discovered in this Example as a top biomarker for suicide, had previous evidence for involvement in other psychiatric disorders, such as ASD and BP. Interestingly, it was identified in a previous study as a blood biomarker increased in expression in low mood states in bipolar participants, and it is increased in expression in the current Example in high suicidal ideation states. Increased expression of CADM1 is associated with decreased cellular proliferation and with apoptosis, and this gene is decreased in expression or silenced in certain types of cancers.

A 22-item scale and app for suicide risk, Convergent Functional Information for Suicidality (CFI-S), was also developed, which integrates information about known life events, mental health, physical health, stress, addictions, and cultural factors that can influence suicide risk. Clinical risk predictors and scales are of high interest in the military and in the general population at large. The scale disclosed herein builds on those excellent prior achievements, while aiming for comprehensiveness, simplicity and quantification similar to a polygenic risk score. CFI-S is able to distinguish between individuals who committed suicide (coroner's cases, information obtained from the next of kin, n=35) and those high risk participants who did not, but had experienced changes in suicidal ideation (e.g., the discovery cohort of psychiatric participants described herein). Items of the CFI-S scale that were the most significantly different were analyzed. Seven (7) items that were significantly different were identified, 5 of which survived Bonferroni correction: lack of coping skills when faced with stress (p=3.35E-11), dissatisfaction with current life (p=2.77E-06), lack of hope for the future (4.58E-05), current substance abuse (p=1.25E-04), and acute loss/grief (p=9.45E-4). The top item was inability to cope with stress, which was independently consistent with the biological mechanistic results discussed above.

CFI-S provided good accuracy (ROC AUC 0.70, p-value 0.006) at predicting future hospitalizations for suicidality in the first year, across diagnostic groups. CFI-Suicide had very good accuracy (AUC 0.89, p-value 3.53E-13) at predicting suicidal ideation in psychiatric participants across diagnostic groups. Within diagnostic groups, in affective disorders, the accuracy was even higher. CFI-S had excellent accuracy at predicting high suicidal ideation in bipolar participants (AUC 0.97, p-value 1.75E-06) and in depression participants (AUC 0.95, p-value 7.98E-06).

Previously, the TASS (Total Affective State Scale) was developed and described for measuring mood and anxiety. The wording used in TASS was simplified and a new app was developed for an 11 item scale for measuring mood and anxiety, the Simplified Affective State Scale (SASS). The SASS is a set of 11 visual analog scales (7 for mood, 4 for anxiety) that provides a number ranging from 0 to 100 for mood state and for anxiety state.

SASS had very good accuracy (AUC 0.85, 9.96E-11) at predicting suicidal ideation in psychiatric participants across diagnostic groups. Within diagnostic groups, in affective disorders, the accuracy was even higher (AUC 0.87) in both bipolar disorder and depression. SASS also had good accuracy (AUC 0.71, p-value 0.008) at predicting future hospitalizations for suicidality in the first year following testing.

The best single biomarker predictor for suicidal ideation state across all diagnostic groups was SLC4A4, the top increased biomarker from AP CFG prioritization (AUC 0.72, p-value 2.41E-05). Within diagnostic groups, the accuracy was even higher. SLC4A4 had very good accuracy at predicting future high suicidal ideation in bipolar participants (AUC 0.93, p-value 9.45E-06) and good accuracy in schizophrenia participants (AUC 0.76, p-value 0.030). SLC4A4 is a sodium-bicarbonate co-transporter that regulates intracellular pH, and possibly apoptosis. Very little is known to date about its roles in the brain, thus representing a completely novel finding.

SKA2, the top decreased biomarker from AP and DE CFG, had good accuracy at predicting suicidal ideation across all diagnostic groups (AUC 0.69), and even better accuracy in bipolar participants (AUC 0.76, p-value 0.011) and schizophrenia participants (AUC 0.82).

The best single top biomarker predictor for future hospitalizations for suicidal behavior in the first year across all diagnostic groups was SAT1, the top increased biomarker from the DE CFG (AUC 0.55). Within diagnostic groups, in affective disorders, the SAT1 prediction accuracies were higher (depression AUC 0.62, bipolar AUC 0.63).

The a priori primary endpoint was a combined universal predictor for suicide (UP-Suicide), composed of the top biomarkers from discovery, prioritization and validation (n=11), along with CFI-Suicide, and SASS. UP-Suicide is an excellent predictor of suicidal ideation across all disorders in the independent cohort of psychiatric participants (AUC 0.92). UP-Suicide also has good predictive ability for future psychiatric hospitalizations for suicidality in the first year of follow-up (AUC 0.70). The predictive ability of UP-Suicide is notably higher in affective disorder participants (bipolar, depression) (FIGS. 4A & 4B).

Example 2

In this Example, female subjects were analyzed for predicting suicidal ideation and future hospitalizations for suicidality.

Human Participants

Four cohorts were used: one live psychiatric participants discovery cohort (within-participant changes in suicidal ideation; n=12 out of 51); one postmortem coroner's office validation cohort (suicide completers; n=6); and two live psychiatric participants test cohorts—one for predicting suicidal ideation (n=33), and one for predicting future hospitalizations for suicidality (n=24).

The live psychiatric participants were part of a larger longitudinal cohort that was continuously being collected. Participants were recruited from the patient population at the Indianapolis VA Medical Center and Indiana University School of Medicine through referrals from care providers, the use of brochures left in plain sight in public places and mental health clinics, and through word of mouth. All participants understood and signed informed consent forms detailing the research goals, procedure, caveats and safeguards. Participants completed diagnostic assessments by an extensive structured clinical interview—Diagnostic Interview for Genetic Studies—at a baseline visit, followed by up to six testing visits, 3-6 months apart or whenever a new psychiatric hospitalization occurred. At each testing visit, they received a series of psychiatric rating scales, including the Hamilton Rating Scale for Depression-17, which includes a suicidal ideation (SI) rating item (FIG. 10A), and the blood was drawn. Whole blood (10 ml) was collected in two RNA-stabilizing PAXgene tubes, labeled with an anonymized ID number, and stored at −80 degrees C. in a locked freezer until the time of future processing. Whole-blood (predominantly lymphocyte) RNA was extracted for microarray gene expression studies from the PAXgene tubes, as detailed below. This Exampled focused on a female population.

The within participant discovery cohort, from which the biomarker data were derived, consisted of 12 female participants with psychiatric disorders and multiple visits in the lab, who each had at least one diametric change in SI scores from no SI to high SI from one testing visit to another. There were 7 participants with 3 visits each, and 5 participants with 2 visits each, resulting in a total of 31 blood samples for subsequent microarray studies (FIGS. 10B and 10C).

The postmortem cohort, in which the top biomarker findings were validated for behavior, consisted of a demographically matched cohort of 6 female violent suicide completers obtained through the Marion County coroner's office (FIG. 14). A last observed alive postmortem interval of 24 hours or less was required, and the cases selected had completed suicide by means other than overdose, which could affect gene expression. 5 participants completed suicide by gunshot to head or chest, and 1 by asphyxiation. Next of kin signed informed consent at the coroner's office for donation of blood for research. The samples were collected as part of the INBRAIN initiative (Indiana Center for Biomarker Research in Neuropsychiatry).

The independent test cohort for predicting suicidal ideation (FIG. 14) consisted of 33 female participants with psychiatric disorders, demographically matched with the discovery cohort, with one or multiple testing visits in the lab, with either no SI, intermediate SI, or high SI, resulting in a total of 74 blood samples in whom whole-genome blood gene expression data were obtained (FIG. 14).

The test cohort for predicting future hospitalizations (FIG. 14) consisted of 24 female participants in whom whole-genome blood gene expression data were obtained at testing visits over the years as part of a longitudinal study. If the participants had multiple testing visits, the visit with the highest marker (or combination of markers) levels was selected for the analyses (so called "high watermark" or index visit). The participants' subsequent number of psychiatric hospitalizations, with or without suicidality (ideation or attempt), was tabulated from electronic medical records. Participants were evaluated for the presence of future hospitalizations for suicidality, and for the frequency of such hospitalizations. A hospitalization was deemed to be without suicidality if suicidality was not listed as a reason for admission, and no SI was described in the admission and discharge medical notes. Conversely, a hospitalization was deemed to be because of suicidality if suicidal acts or intent was listed as a reason for admission, and/or SI was described in the admission and discharge medical notes.

Medications

The participants in the discovery cohort were all diagnosed with various psychiatric disorders (FIG. 14). Their psychiatric medications were listed in their electronic medical records, and documented at the time of each testing visit. The participants were on a variety of different psychiatric medications: mood stabilizers, antidepressants, antipsychotics, benzodiazepines and others (data not shown). Medications can have a strong influence on gene expression. However, discovery of differentially expressed genes was based on within-participant analyses, which factor out not only genetic background effects but also medication effects, as the participants had no major medication changes between visits. Moreover, there was no consistent pattern in any particular type of medication, or between any change in medications and SI, in the rare instances where there were changes in medications between visits.

Clock Gene Database

In this Example, a database was compiled of genes associated with circadian function, by using a combination of review papers (Zhang et al. Cell 2009; 139(1):19-210, McCarthy and Welsh Journal of biological rhythms 2012; 27(5):339-352) and searches of existing databases CircaDB (circadb.hogeneschlab.org), GeneCards (www.genecards.org), and GenAtlas (genatlas.medecine.univ-paris5.fr). Using the data, a total of 1280 genes were identified that show circadian functioning. The genes were classified into "core" clock genes, i.e. those genes that are the main engine driving circadian function (n=18), "immediate" clock genes, i.e. the genes that directly input or output to the core clock (n=331), and "distant" clock genes, i.e. genes that directly input or output to the immediate clock genes (n=1,119).

Clinical Measures

The Simplified Affective State Scale (SASS) is an 11-item scale for measuring mood and anxiety. The SASS has a set of 11 visual analog scales (7 for mood, 4 for anxiety) that ends up providing a number ranging from 0 to 100 for mood state, and the same for anxiety state. Also developed is an Android app version.

In some embodiments, the systems and methods described utilize a computer implemented method for assessing suicidal risk factors based upon patient psychiatric information further including mood information, anxiety information, and other psychiatric symptom information. Any and all such patient psychiatric information may be represented as a quantitative rating on a defined analog scale, such as the ratings and scales described above. Further, as used herein, such patient psychiatric information may be processed using an associated processing algorithm. The associated processing algorithm may include calculating mean values for each component of patient psychiatric information and then assigning a suitable weighting to each calculated mean value. The processing algorithm may thus use the quantitative ratings of the patient psychiatric information as inputs to calculate a diagnostic output score. The diagnostic output score may be used to compare to reference scores (from a diagnostic database) associated with patients having psychiatric symptom information (e.g., psychiatric disorder diagnosis or lack thereof) similar to the patient. By such comparison, the diagnostic output score may be assigned a percentile. The diagnostic output score may also be compared to the reference scores in the diagnostic database associated with individuals with no suicidality and high suicidality. Thus, if the diagnostic output score meets or exceeds a high suicidality reference score, a patient may be marked as at risk for suicide. Conversely, if the diagnostic output score meets or falls below a low suicidality reference score, a patient may be marked as not at risk for suicide.

Convergent Functional Information for Suicidality (CFI-S) is a 22-item scale and Android app for suicide risk, which integrates, in a simple binary fashion (Yes—1, No—0), similar to a polygenic risk score, information about known life events, mental health, physical health, stress, addictions, and cultural factors that can influence suicide risk. The scale was administered at participant testing visits (n=39), or scored based on retrospective electronic medical record information and Diagnostic Interview for Genetic Testing (DIGS) information (n=48). When information was not available for an item, it was not scored (NA).

In other embodiments, the systems and methods described utilize a computer implemented method for assessing suicidal risk factors based upon socio-demographic/psychological suicidal risk factors. Any and all such socio-demographic/psychological suicidal risk factors may be represented as a quantitative rating on a defined analog scale, such as the ratings and scales described above. Further, as used herein, such socio-demographic/psychological suicidal risk factors may be processed using an associated processing algorithm. The associated processing algorithm may include calculating mean values for each component socio-demographic/psychological suicidal risk factor and then assigning a suitable weighting to each calculated mean value. The processing algorithm may thus use the quantitative ratings of the socio-demographic/psychological suicidal risk factors as inputs to calculate a diagnostic output score. The diagnostic output score may be used to compare to reference scores (from a diagnostic database) associated with patients having socio-demographic/psychological suicidal risk factors similar to the patient. By such comparison, the diagnostic output score may be assigned a percentile. The diagnostic output score may also be compared to the reference scores in the diagnostic database associated with individuals with no suicidality and high suicidality. Thus, if the diagnostic output score meets or exceeds a high suicidality reference score, a patient may be marked as at risk for suicide. Conversely, if the diagnostic output score meets or falls below a low suicidality reference score, a patient may be marked as not at risk for suicide.

In some computer-implemented methods described above and herein, multiple computing devices may interact with one another (e.g., first and second computer devices). To protect data and privacy, such requests and transmissions are made using data encryption.

Combining Gene Expression and Clinical Measures

The Universal Predictor for Suicide (UP-Suicide) construct, the primary endpoint, was decided upon as part of a apriori study design to be broad-spectrum, and combine the top Bonferroni validated biomarkers with the phenomic (clinical) markers (SASS and CFI-S).

Results

Discovery of Biomarkers for Suicidal Ideation

A whole-genome gene expression profiling was conducted in the blood samples from a longitudinally followed cohort of female participants with psychiatric disorders that predispose to suicidality. The samples were collected at repeated visits, 3-6 months apart. State information about suicidal ideation (SI) was collected from a questionnaire (HAMD) administered at the time of each blood draw. Out of 51 female psychiatric participants (with a total of 123 visits) followed longitudinally in this Example, with a diagnosis of BP, MDD, SZ and SZA, there were 12 participants that switched from a no SI (SI score of 0) to a high SI state (SI score of 2 and above) at different visits, which was the intended discovery group (FIG. 10B). A within-participant design was used to analyze data from these 12 participants and their 31 visits. A within-participant design factors out genetic variability, as well as some medications, lifestyle, and demographic effects on gene expression, permitting identification of relevant signal with Ns as small as 1. Another benefit of a within-participant design may be accuracy/consistency of self-report of psychiatric symptoms ('phene expression'), similar in rationale to the signal detection benefits it provides in gene expression.

For discovery, two differential expression methodologies were used: Absent/Present (AP) (reflecting on/off of transcription), and Differential Expression (DE) (reflecting more subtle gradual changes in expression levels). The genes that tracked suicidal ideation in each participant were identified in the analyses. Three thresholds were used for increased in expression genes and for decreased in expression genes: ≥33.3% (low), ≥50% (medium), and ≥80% (high) of the maximum scoring increased and decreased gene across participants. Such a restrictive approach was used as a way of minimizing false positives, even at the risk of having false negatives. For example, there were genes on each of the two lists, from AP and DE analyses, that had clear prior evidence for involvement in suicidality, such as AKAP10 (31.7%) and MED28 (31.8%) from AP, and S100B (31.7%) and SKA2 (31.4%) for DE, but were not included in subsequent analyses because they did not meet the apriori set 33.3% threshold. Notably, SKA2 reproduces the results in males (Example 1).

Prioritization of Biomarkers Based on Prior Evidence in the Field

These differentially expressed genes were then prioritized using a Bayesian-like Convergent Functional Genomics (CFG) approach (FIGS. 11B and 11C) integrating all the previously published human genetic evidence, postmortem brain gene expression evidence, and peripheral fluids evidence for suicide in the field available at the time of this analyses (i.e., September 2015). This is a way of identifying and prioritizing disease relevant genomic biomarkers, extracting generalizable signal out of potential cohort-specific noise and genetic heterogeneity. The manually curated databases of the psychiatric genomic and proteomic literature to date were used in CFG analyses. The CFG approach is thus a de facto field-wide collaboration.

Validation of Biomarkers for Behavior in Suicide Completers

For validation in suicide completers, 1471 genes were used that had a CFG score of 4 and above, from AP and DE, reflecting either maximum internal score from discovery or additional external literature cross-validating evidence. Out of these, 882 did not show any stepwise change in suicide completers (NC—non-concordant). As such, they may be involved primarily in ideation and not in behavior. The remaining 589 genes (40.0%) had levels of expression that were changed stepwise from no suicidal ideation to high suicidal ideation to suicide completion. 396 of these genes (26.9%) were nominally significant, and 49 genes (50 probesets—two for JUN) (3.33%) survived Bonferroni correction for multiple comparisons (FIG. 11C). These genes are likely involved in suicidal ideation and suicidal behavior. (A person can have suicidal ideation without suicidal behavior, but cannot have suicidal behavior without suicidal ideation).

Selection of Biomarkers for Testing of Predictive Ability

For testing, Bonferroni validated biomarkers (49 genes, 50 probesets) were focused on. A secondary analysis of the top scoring biomarkers from both discovery and prioritization (65 genes) was conducted so as to avoid potential false negatives in the validation step due to possible postmortem artefacts or extreme stringency of statistical cutoff. The top CFG scoring genes after the Bonferroni validation step were BCL2 and GSK3B. The top CFG scoring genes from the discovery and prioritization steps were FAM214A, CLTA, HSPD1, and ZMYND8. Notably, all have co-directional gene expression changes evidence in brains of suicide completers in studies form other groups.

Biological Understanding

Unbiased biological pathway analyses and hypothesis driven mechanistic queries, overall disease involvement and specific neuropsychiatric disorders queries, and overall drug modulation along with targeted queries for omega-3, lithium and clozapine were studied (FIGS. 15 and 17). Administration of omega-3s in particular may be a mass-deployable therapeutic and preventive strategy.

The sets of biomarkers identified have biological roles in inflammation, neurotrophins, inositol signaling, stress response, and perhaps overall the switch between cell survival and proliferation vs. apoptosis (FIG. 15).

The involvement of these biomarkers for suicidality in other psychiatric disorders were also analyzed. FAM214A, MOB3B, ZNF548, and ARHGAP35 were relatively specific for suicide, based on the evidence to date in the field, and were also identified co-directionally in the previous male work (Example 1). BCL2, GSK3B, HSPD1, and PER1 were less specific for suicide, having equally high evidence for involvement in suicide and in other psychiatric disorders. BCL2 was also identified co-directionally in Example 1.

HSPD1, found to be a top biomarker in this Example, increased in expression in suicidality, and was also increased in expression in the blood following anti-depressant treatment. Thus, this may be a useful biomarker for treatment-emergent suicidal ideation (TESI).

Further, a number of the genes changed in expression in opposite direction in suicide in this Example vs. high mood in Example 1—SSBP2, ZNF596, suggesting that suicidal participants are in a low mood state. Also, some of the top suicide biomarkers are changed in expression in the same direction as in high psychosis participants in a previous psychosis biomarker study—HERC4, PIP5K1B, SLC35B3, SNX27, KIR2DL4, NUDT10, suggesting that suicidal participants may be in a psychosis-like state. Taken together, the data indicates that suicidality could be viewed as a psychotic dysphoric state. This molecularly informed view is consistent with the emerging clinical evidence in the field.

A number of top biomarkers identified have biological roles that are related to the core circadian clock (such as PER1), or modulate the circadian clock (such as CSNK1A1), or show at least some circadian pattern (such as HTRA1). To be able to ascertain all the genes in the dataset that were circadian and do estimates for enrichment, a database from literature was compiled of all the known genes that fall into these three categories, numbering a total of 1468 genes. Using an estimate of about 21,000 genes in the human genome, that gives about 7% of genes having some circadian pattern. Out of the 49 Bonferroni validated biomarker genes, 7 had circadian evidence (14.3%), suggesting a 2-fold enrichment for circadian genes.

Additionally, biological pathway analyses were conducted on the genes that, after discovery and prioritization, were stepwise changed in suicide completers (n=882) and may be involved in ideation and behavior vs. those that were not stepwise changed (n=589), and that may only be involved in ideation. The genes involved in ideation map to pathways related to PI3K signaling. The genes involved in behavior map to pathways related to glucocorticoid receptor signaling. This is consistent with ideation being related to neurotrophic factors, and behavior being related to stress.

Clinical Information

Figure 12A:
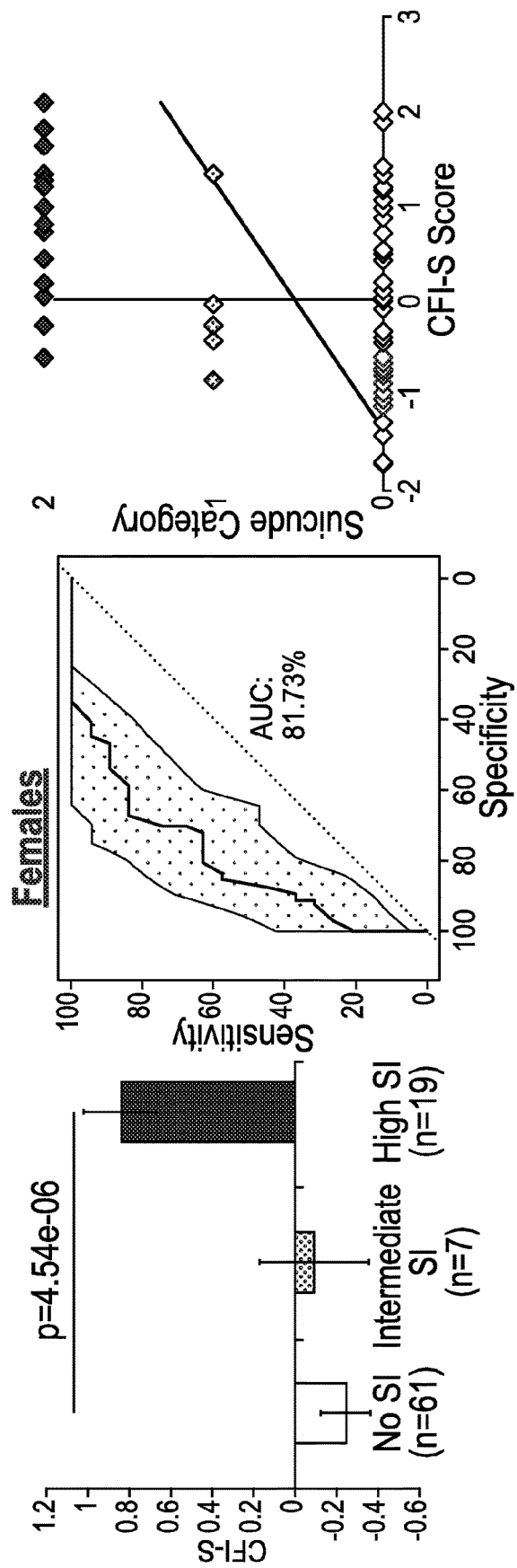
Figure 12C:
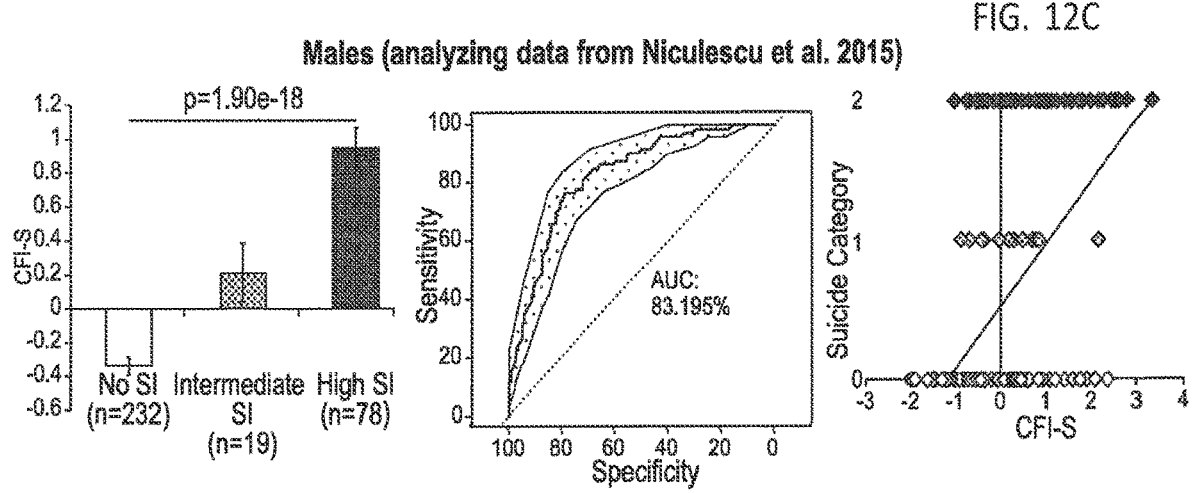

A 22-item scale and app were used for suicide risk, Convergent Functional Information for Suicidality (CFI-S), which scores in a simple binary fashion and integrates information about known life events, mental health, physical health, stress, addictions, and cultural factors that can influence suicide risk. Determining which items of the CFI-S scale were the most significantly different between no and high suicidal ideation live participants was analyzed (FIG. 12A). Seven items were identified that were significantly different: lack of positive relationships/social isolation (p=0.004), substance abuse (p=0.0071), history of impulsive behaviors (p=0.015), lack of religious beliefs (p=0.018), past history of suicidal acts/gestures (p=0.025), rejection (p=0.029), and history of command auditory hallucinations (p=0.045) (FIG. 12B). It is noted that lack of positive relationships/social isolation was the second top item in males as well. Social isolation increases vulnerability to stress, which is independently consistent with the biological marker results.

Testing for Predictive Ability

The best single increased (risk) biomarker predictor for suicidal ideation state was EPB41L5 (ROC AUC 0.68, p-value 0.06; Pearson Correlation 0.22, p-value 0.03), an increased in expression, Bonferroni validated biomarker (FIGS. 16A-16C). This biomarker was also identified co-directionally in Example 1, and has no evidence for involvement in other psychiatric disorders. The best single decreased (protective) biomarker predictor for suicidal ideation is PIK3C3 (ROC AUC 0.65, p-value 0.1; Pearson Correlation −0.21, p-value 0.037), a decreased in expression, Bonferroni validated biomarker (FIGS. 16A-16C). PIK3C3 is also decreased in expression in postmortem brains in depression.

The best single increased (risk) biomarker predictor for future hospitalizations for suicidality was HTRA1 (ROC AUC 0.84, p-value 0.01; Cox Regression Hazard Ratio 4.55, p-value 0.01), an increased in expression, Bonferroni validated biomarker (FIGS. 16A-16C). HTRA1 is also increased in expression in the blood of schizophrenics. The best single decreased (protective) biomarker predictor for future hospitalizations for suicidality was CSNK1A1 (ROC AUC 0.96, p-value 0.0007; Cox Regression Hazard Ratio 620.5, p-value 0.02), a top discovery and prioritization, non-Bonferroni validated biomarker (FIGS. 16A-16C). This biomarker was also identified co-directionally in Example 1. CSNK1A1 (casein kinase 1, alpha 1) is a circadian clock gene, part of the input into the core clock. It decreased in expression in suicidality, and decreased in postmortem brains of alcoholics. It has further been found to be increased in expression by mood stabilizers and by omega-3 fatty acids. PIK3C3 was also found to be a good predictor for future hospitalizations for suicidality (ROC AUC 0.9, p-value 0.011) (FIGS. 16A-16C).

BCL2, the top CFG scoring biomarker from validation, had good accuracy at predicting future hospitalizations for suicidality (ROC AUC 0.89, p-value 0.007; Cox Regression Hazard Ratio 3.08, p-value 0.01) (FIGS. 16A-16C). In the panel of 50 validated biomarkers, BioM-50, had even better accuracy at predicting future hospitalizations for suicidality (ROC AUC 0.94, p-value 0.002; Cox Regression Hazard Ratio 89.46, p-value 0.02) (FIGS. 16A-16C). Overall, in women, blood biomarkers seemed to perform better for predicting future hospitalizations for suicidality (trait) than for predicting suicidal ideation (state). This is different than the trend seen in Example 1, where blood biomarkers were somewhat better predictors of state than of trait.

CFI-S had very good accuracy (ROC AUC 0.84, p-value 0.002; Pearson Correlation 0.39, p-value 0.001) at predicting suicidal ideation in psychiatric participants across diagnostic groups. The other app, SASS, also had very good accuracy (ROC AUC 0.81, p-value 0.003; Pearson Correlation 0.38, p-value 0.0005) at predicting suicidal ideation in women psychiatric participants. The combination of the apps was synergistic (ROC AUC 0.87, p-value 0.0009; Pearson Correlation 0.48, p-value 0.0001). Thus, even without the benefit of potentially more costly and labor intensive blood biomarker testing, clinically useful predictions could be made with the apps.

Figure 13A:
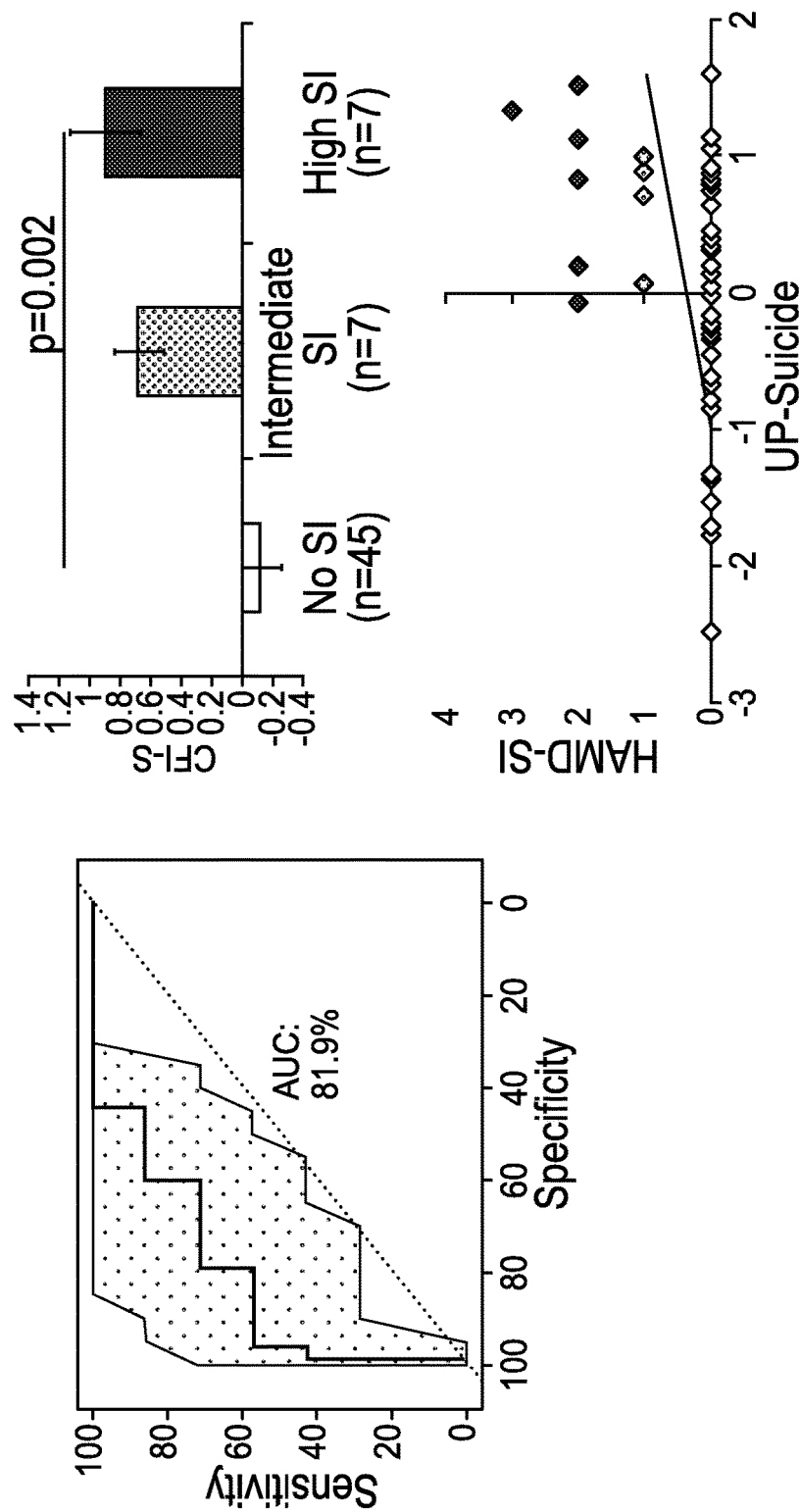
FIGS. 13A & 13B depict UP-Suicide predictions of suicidal ideation in the independent test cohort, and predicting future hospitalizations due to suicidality as analyzed in Example 2.
Figure 13B:
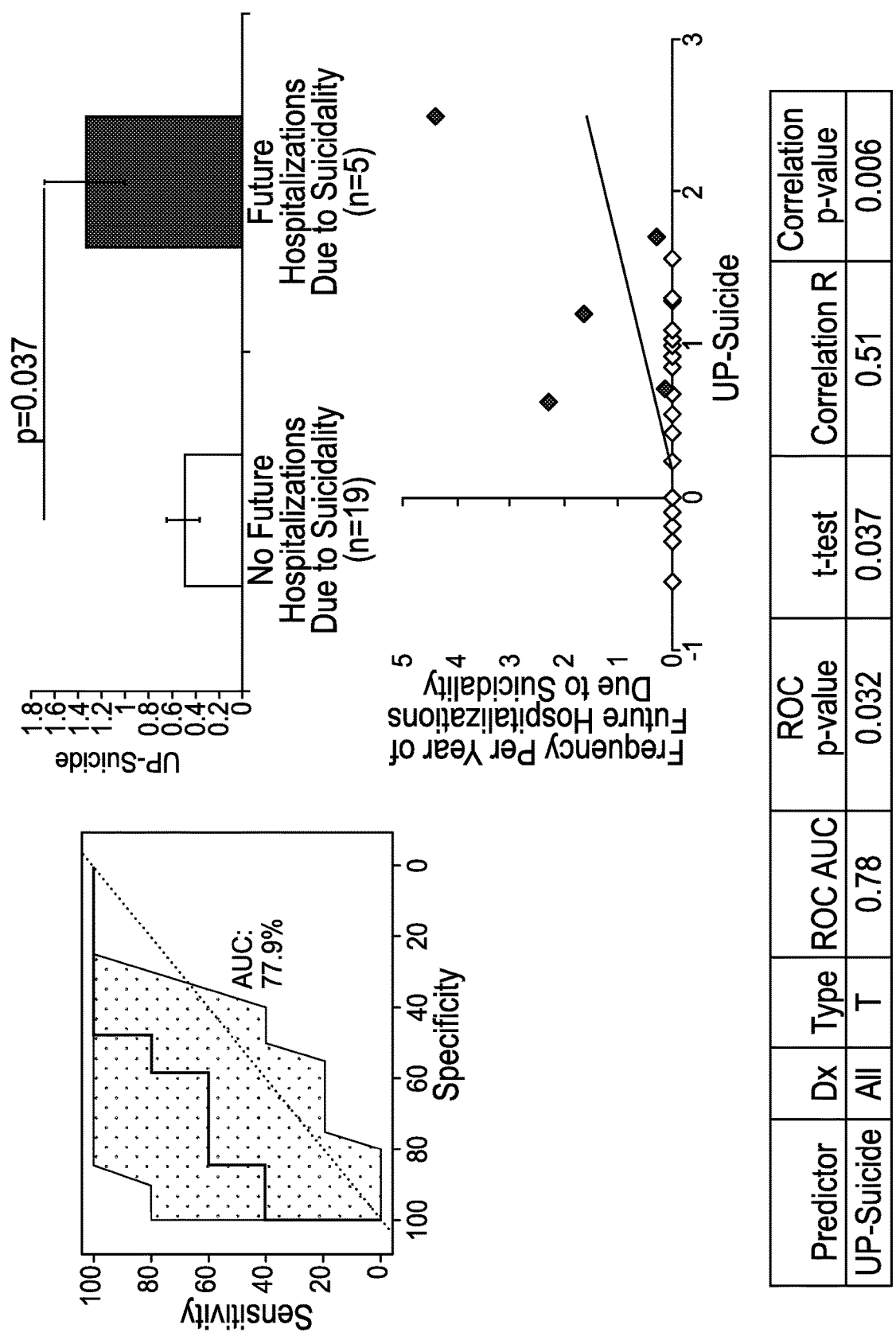

The apriori primary endpoint was a combined universal predictor for suicide (UP-Suicide), composed of CFI-S and SASS, along with the Bonferroni validated biomarkers (n=50) resulting from the sequential discovery for ideation, prioritization with CFG, and validation for behavior in suicide completers steps. UP-Suicide was a good predictor of suicidal ideation (ROC AUC 0.82, p-value 0.003; Pearson Correlation 0.43, p-value 0.0003) (FIGS. 13A, 13B and 16). UP-Suicide also had good predictive ability for future psychiatric hospitalizations for suicidality (ROC AUC 0.78, p-value 0.032; Cox Regression Hazard Ratio 9.61, p-value 0.01).

Discussion

The present Example identified markers involved in suicidal ideation and suicidal behavior, including suicide completion, in females. Markers involved in behavior may be on a continuum with some of the markers involved in ideation, varying in the degree of expression changes from less severe (ideation) to more severe (behavior). One cannot have suicidal behavior without suicidal ideation, but it may be possible to have suicidal ideation without suicidal behavior.

50 biomarkers were found to have survived Bonferroni correction (49 genes; one gene, JUN, had two different probesets that validated). Additionally, 65 other biomarkers that were non Bonferroni, but had maximum internal score of 4 in discovery and a CFG score of 6 and above, meaning that in addition to strong evidence in this Example, they also had prior independent evidence of involvement in suicide from other studies, were also studied. These additional biomarkers are likely involved in suicide, but did not make the Bonferroni validation cutoff due to its stringency or potential technical/postmortem artifact reasons (FIGS. 26 and 30).

Data validating the CFI-S in women in the combined discovery and test cohort of live psychiatric participants was analyzed (FIGS. 12A and 12B) and compared with similar analyses in men (Example 1). The chronic stress of lack of positive relationships/social isolation was identified as the top differential item in women, which is consistent with biological data from the biomarker side of this Example.

In assessing anxiety and mood, it was shown that anxiety measures cluster with suicidal ideation and CFI-S, and mood measures are in the opposite cluster, suggesting that the participants have high suicidal ideation when they have high anxiety and low mood (FIG. 10C).

The rationale for identifying blood biomarkers as opposed to brain biomarkers is a pragmatic one—the brain cannot be readily accessed in live individuals. Other peripheral fluids, such as CSF, require more invasive and painful procedures. Nevertheless, it is likely that many of the peripheral blood transcriptomic changes are not necessarily mirroring what is happening in the brain, and vice-versa. The keys to finding peripheral biomarkers are, first, to have a powerful discovery approach, such as the within-participant design, that closely tracks the phenotype you are trying to measure and reduces noise. Second, cross-validating and prioritizing the results with other lines of evidence, such as brain gene expression and genetic data, are important in order to establish relevance and generalizability of findings. Third, it is important to validate for behavior in an independent cohort with a robust and relevant phenotype, in this case suicide completers. Fourth, testing for predictive ability in independent/prospective cohorts is a must.

Biomarkers that survive such a rigorous step-wise discovery, prioritization, validation and testing process are likely directly relevant to the disorder studied. As such, whether they are involved in other psychiatric disorders or are relatively specific for suicide, and whether they are the modulated by existing drugs in general, and drugs known to treat suicidality in particular were evaluated.

A series of biomarkers have been identified that seem to be changed in opposite direction in suicide vs. in treatments with omega-3 fatty acids, lithium, clozapine. These biomarkers could potentially be used to stratify patients to different treatment approaches, and monitor their response. BCL2, JUN, GHA1, ENTPD1, ITIH5, MBNL1, and SSBP2 were changed in expression by two of these three treatments, suggesting they may be core to the anti-suicidal mechanism of these drugs. BCL2, CAT, and JUN may be useful blood pharmacogenomic markers of response to lithium. CD84, MBNL1, and RAB22A may be useful blood pharmacogenomic markers of response to clozapine. NDRG1, FOXP1, AFF3, ATXN1, CSNK1A1, ENTPD1, ITIH5, PRDX3, and SSBP2 may be useful blood pharmacogenomic markers of response to omega-3 fatty acids. Three existing drugs used for other indications have been identified as targeting the top suicide biomarkers identified, and could potentially be re-purposed for testing in treatment of acute suicidality: anakinra (inhibiting ILR1), enzastaurin (inhibiting AKT3), and tesevatinib (inhibiting EPHB4). Additionally, Connectivity Map (ref) analyses identified compounds that induced gene expression signatures that were the opposite of those present in suicide, and might generate leads and/or be tested for use to treat/prevent suicidality: betulin (an anti-cancer compound from the bark of birch trees), zalcitabine (an anti-HIV drug), and atractyloside (a toxic glycoside). Other common drugs identified by the Connectivity Map analyses were nafcillin, lansoprazole, mifepristone, LY294002, minoxidil, acetysalicilic acid, estradiol, buspirone, dicloxacillin, corticosterone, metformin, diphenhydramine, haloperidol, and fluoxetine.

Of note, a number of biomarkers from the current Example in women reproduced and were co-directional with previous findings in Example 1 (BCL2, ALDH3A2, FAM214A, CLTA, ZMYND8, JUN), whereas others had changes in opposite directions (GSK3B, HSPD1, AK2, CAT), underlying the issue of biological context and differences in suicidality between the two genders.

Disclosed herein are instruments (biomarkers and applications) for predicting suicidality, that do not require asking the person assessed if they have suicidal thoughts, as individuals who are truly suicidal often do not share that information with people close to them or with clinicians. The widespread use of such risk prediction tests as part of routine or targeted healthcare assessments will lead to early disease interception followed by preventive lifestyle modifications or treatment. Biomarkers identified herein for suicidal ideation are enriched for genes involved in neuronal connectivity and schizophrenia. Biomarkers identified herein also validated for suicide behavior are enriched for genes involved in neuronal activity and mood.

Worldwide, one person dies every 40 seconds through suicide, a potentially preventable tragedy. A limiting step in the ability to intervene is the lack of objective, reliable predictors. A powerful within-participant discovery approach is disclosed herein in which genes that change in expression between no suicidal ideation and high suicidal ideation states were identified. The methods disclosed herein do not require asking the person assessed if they have thoughts of suicide, as individuals who are truly suicidal often do not share that information with clinicians. The widespread use of such risk prediction tests as part of routine or targeted healthcare assessments will lead to early disease interception followed by preventive lifestyle modifications and proactive treatment.

In view of the above, it will be seen that the several advantages of the disclosure are achieved and other advantageous results attained. As various changes could be made in the above methods without departing from the scope of the disclosure, it is intended that all matter contained in the above description and shown in the accompanying drawings shall be interpreted as illustrative and not in a limiting sense.

When introducing elements of the present disclosure or the various versions, embodiment(s) or aspects thereof, the articles "a", "an", "the" and "said" are intended to mean that there are one or more of the elements. The terms "comprising", "including" and "having" are intended to be inclusive and mean that there may be additional elements other than the listed elements.

What is claimed is:

1. A method for assessing and mitigating suicidality in a male subject in need thereof, comprising:
determining an expression level of at least a first panel of blood biomarkers or a second panel of blood biomarkers in a sample from the subject, where the first panel of blood biomarkers comprises solute carrier family 4 (sodium bicarbonate cotransporter), member 4 (SLC4A4), cell adhesion molecule 1 CADM1, dystrobrevin, alpha (DTNA), spermidine/spermine N1-acetyl transferase 1 (SAT1), interleukin 6 (interferon, beta 2) (IL6), RAS-like family 11 member B (RASL11B), Glutamate Receptor, Ionotropic, Kainate 2 (GRIK2), histone cluster 1, H2bo (HIST1H2BO), jun protooncogene (JUN), and GRB2-Associated Binding Protein 1 (GAB1), and where the second panel of blood biomarkers comprises spindle and kinetochore associated complex subunit 2 (SKA2), CAP-GLY domain containing linker protein family, member 4 (CLIP4), kinesin family member 2C (KIF2C), kelch domain containing 3 (KLHDC3), chemokine (C-C motif) ligand 28 (CCL28), v-ets avian erythroblastosis virus E26 oncogene homolog (ERG), adenylate kinase 2 (AK2), Myelin Basic Protein (MBP), and fatty acid desaturase 1 (FADS1);

identifying a male subject having suicidality where the expression level of the blood biomarkers in the first panel is increased relative to a reference expression level, or, the expression level of the blood biomarkers in the second panel is decreased relative to a reference expression level; and, administering to the male subject identified as having suicidality a drug to treat the suicidality.

2. The method according to claim 1, where the identifying step further comprises comparing a biomarker panel score of the male subject to a biomarker panel score of a reference.

3. A method for assessing and mitigating suicidality in a female subject in need thereof, comprising:

determining an expression level of at least a first panel of blood biomarkers or a second panel of blood biomarkers in a sample from the subject, where the first panel of blood biomarkers comprises erythrocyte membrane protein band 4.1 like 5 (EPB/41L5), HtRA serine peptidase 1 (HTRA1), deleted in primary ciliary dyskinesia homolog (DPCD), general transcription factor IIIC, polypeptide 3 102 kDa (GTF3C3), period circadian clock 1 (PER1), pyridoxal-dependent decarboxylase domain containing 1 (PDXDC1) kelch-like family member 28 (KLHL28), ubiquitin interaction motif containing 1 (UIMC1), sorting nexin family member 27 (SNX27), Glutamate Receptor, and tonotropic, Kainate 2 (GRIK2), and where the second panel of blood biomarkers comprises phosphatidylinositol 3-kinase, catalytic subunit type 3 (PIK3C3), aldehyde dehydrogenase 3 family, member A2 (ALDH3A2), ARP3 actin-related protein 3 homolog (yeast) (ACTR3), B-cell CLL (BCL2), MOB kinase activator 3B (MOB3B), casein kinase 1, alpha 1 (CSNK1A1), La ribonucleoprotein domain family, member 4 (LARP4), zinc finger protein 548 (ZNF548), prolylcarhoxypeptidase (angiotensinase C) (PRCP), solute carrier family 35 (adenosine 3'-phospho 5'-phosphosulfate transporter), and member B3 (SLC35B3);

identifying a female subject having suicidality Where the expression level of the blood biomarkers in the first panel is increased relative to a reference expression level, or, the expression level of the blood biomarkers in the second panel is decreased relative to a reference, expression level; and, administering to the female subject identified as having suicidality a drug to treat the suicidality.

4. The method according to claim 3, where the identifying step further comprises comparing a biomarker panel score of the female subject to a biomarker panel score of a reference.

5. The method according to claim 1, where the drug is selected from the group consisting of dissociants, mood stabilizers, antipyschotics, antidepressants and omega-3-fatty acids.

6. The method according to claim 3, where the drug is selected from the group consisting of dissociants, mood stabilizers, antipyschotics, antidepressants and omega-3-fatty acids.

7. The method according to claim 1, where the drug is selected from the group consisting of ketamine, lithium, clozapine, chlorpromazine, prochlorperazine, selegeline, fluoxetine, trimipramine, and docosahexaenoic acid.

8. The method according to claim 3, where the drug is selected from the group consisting of ketamine, lithium, clozapine, chlorpromazine, prochlorperazine, selegeline, fluoxetine, trimipramine, and docosahexaenoic acid.

9. The method according to claim 1, where the drug is selected from the group consisting of tocilizumab, tenoxicam, ramifenazone, betulin, dl-alpha tocopherol, hesperidin, calcium folinate, harpagoside, rilmenidine, harman, homatropine, diphenhydramine, pirenperone, asiaticoside, adiphenine, metformin, chlorogenic acid, verapamil, metaraminol, yohimbine, and trimethadione.

10. The method according to claim 3, where the drug is selected from the group consisting of tocilizumab, tenoxicam, ramifenazone, betulin, dl-alpha tocopherol, hesperidin, calcium folinate, harpagoside, rilmenidine, harman, homatropine, diphenhydramine, pirenperone, asiaticoside, adiphenine, metformin, chlorogenic acid, verapamil, metaraminol, yohimbine, and trimethadione.

11. The method according to claim 1, where the drug is selected from the group consisting of: thiamine, homatropine, vitexin, ergocalciferol, tropicamide, (-)-atenolol, haloperidol, and spaglumic acid.

12. The method according to claim 3, where the drug is selected from the group consisting of: mifepristone, lansoprazole, nafcillin, and betulin.

13. The method according to claim 1, wherein the subject has a psychiatric disorder selected from the group consisting of bipolar disorder, major depressive disorder, schizophrenia, schizoaffective disorder, anxiety disorders, and post-traumatic stress disorder.

14. The method according to claim 3, wherein the subject has a psychiatric disorder selected from the group consisting of bipolar disorder, major depressive disorder, schizophrenia, schizoaffective disorder, anxiety disorders, and post-traumatic stress disorder.

* * * * *